(12) United States Patent
Eckhardt et al.

(10) Patent No.: US 8,829,027 B2
(45) Date of Patent: Sep. 9, 2014

(54) UREA DERIVATIVES OF SUBSTITUTED NORTROPANES, MEDICAMENTS CONTAINING SUCH COMPOUNDS AND THEIR USE

(75) Inventors: Matthias Eckhardt, Biberach an der Riss (DE); Bradford S. Hamilton, Biberach an der Riss (DE); Frank Himmelsbach, Mittelbiberach (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 168 days.

(21) Appl. No.: 13/124,259

(22) PCT Filed: Oct. 22, 2009

(86) PCT No.: PCT/EP2009/063913
§ 371 (c)(1),
(2), (4) Date: May 17, 2011

(87) PCT Pub. No.: WO2010/046445
PCT Pub. Date: Apr. 29, 2010

(65) Prior Publication Data
US 2011/0275595 A1 Nov. 10, 2011

(30) Foreign Application Priority Data
Oct. 23, 2008 (EP) .................... 08167440

(51) Int. Cl.
*A61K 31/46* (2006.01)
*C07D 451/02* (2006.01)
*C07D 519/00* (2006.01)

(52) U.S. Cl.
CPC ............ *C07D 451/02* (2013.01); *C07D 519/00* (2013.01)
USPC .......................................... 514/304; 546/127

(58) Field of Classification Search
USPC .......................................... 546/127; 514/304
See application file for complete search history.

(56) References Cited

U.S. PATENT DOCUMENTS

| | | | |
|---|---|---|---|
| 3,341,538 A | 9/1967 | Block et al. | |
| 3,378,587 A | 4/1968 | Reinhardt | |
| 4,043,927 A | 8/1977 | Duling et al. | |
| 4,108,857 A | 8/1978 | Albertson | |
| 7,897,773 B2 * | 3/2011 | Aletru et al. | 546/126 |
| 2006/0089349 A1 | 4/2006 | Gundertofte et al. | |
| 2006/0194780 A1 | 8/2006 | Nargund et al. | |
| 2009/0170894 A1 | 7/2009 | Aletru et al. | |
| 2010/0256363 A1 | 10/2010 | Xu | |
| 2011/0015157 A1 | 1/2011 | Claremon et al. | |
| 2011/0028445 A1 | 2/2011 | Eckhardt et al. | |
| 2011/0112062 A1 | 5/2011 | Claremon et al. | |
| 2011/0136800 A1 | 6/2011 | Eckhardt et al. | |
| 2011/0190262 A1 | 8/2011 | Himmelsbach et al. | |
| 2011/0269736 A1 | 11/2011 | Eckhardt et al. | |
| 2011/0269791 A1 | 11/2011 | Peters et al. | |
| 2011/0275595 A1 | 11/2011 | Eckhardt et al. | |
| 2012/0115853 A1 | 5/2012 | Eckhardt et al. | |
| 2012/0172357 A1 | 7/2012 | Himmelsbach | |

FOREIGN PATENT DOCUMENTS

| | | |
|---|---|---|
| EP | 1864971 A1 | 12/2007 |
| EP | 1935420 A1 | 6/2008 |
| GB | 1077711 A | 8/1967 |
| JP | 2007140188 A | 6/2007 |
| WO | 0155063 A1 | 8/2001 |
| WO | 2004089896 A1 | 10/2004 |
| WO | 2005108361 A1 | 11/2005 |
| WO | 2006024628 A1 | 3/2006 |
| WO | 2006040329 A1 | 4/2006 |
| WO | 2006044174 A2 | 4/2006 |
| WO | 2007051810 A2 | 5/2007 |
| WO | 2007076055 A2 | 7/2007 |
| WO | WO2007076055 * | 7/2007 |
| WO | 2008000951 A2 | 1/2008 |
| WO | 2009017664 A1 | 2/2009 |
| WO | 2009017671 A1 | 2/2009 |
| WO | 2009061498 A1 | 5/2009 |
| WO | 2009063061 A2 | 5/2009 |
| WO | 2009100872 A1 | 8/2009 |
| WO | 2009102428 A2 | 8/2009 |

(Continued)

OTHER PUBLICATIONS

Anantanarayan et al. "Preparation of heteroarylpyrazoles . . . " CA133:4656 (2000).*

(Continued)

*Primary Examiner* — Celia Chang
(74) *Attorney, Agent, or Firm* — Michael P. Morris; David L. Kershner

(57) ABSTRACT

The present invention relates to compounds defined by formula I wherein the groups $R^1$, $Y^1$ to $Y^4$, V, W, and X are defined as in claim 1, possessing valuable pharmacological activity. Particularly the compounds are inhibitors of 11 β-hydroxysteroid dehydrogenase (HSD) 1 and thus are suitable for treatment and prevention of diseases which can be influenced by inhibition of this enzyme, such as metabolic diseases, in particular diabetes type 2, obesity, and dyslipidemia.

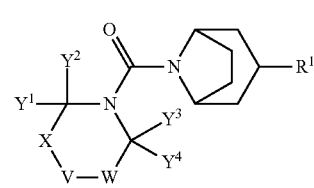

8 Claims, No Drawings

(56) References Cited

FOREIGN PATENT DOCUMENTS

| WO | 2009117109 A1 | 9/2009 |
| WO | 2009138386 A2 | 11/2009 |
| WO | 2010010157 A2 | 1/2010 |
| WO | 2010010174 A1 | 1/2010 |
| WO | 2010023161 A1 | 3/2010 |
| WO | 2010046445 A2 | 4/2010 |
| WO | 2010139673 A1 | 12/2010 |
| WO | 2011057054 A1 | 5/2011 |

OTHER PUBLICATIONS

Helsley et al. "Antispasmodic . . . " CA77:5360 (1972).*
Hembrough et al. "Composition and methods . . . " CA147:134403 (2007).*
Hughes et al. "11-beta-hydroxysteroid . . . " Exp. Opin. Investig. Drugs 17(4)481-496 (2008).*
Olesen "The use of . . . " Current Opin. Drug Dis, Dev. v. 4(4) p. 471-478 (2001).*
Thornber "Isosterism and molecular . . . " Chem. Soc. Rev. v. 8, p. 563-580 (1979).*
Nyenwe et al. "Mnagement of type 2 diabetes . . . " Mtabol. Clin. Exper. v. 60, 1-23 (2011).*
Rammanjireddy et al. "Importance of metformin . . . " Asian J. pharm. Clin. Res. v. 5, suppl 1,p. 1-4 (2012).*
Abstract in English for JP2007140188 publication date 2007.
ChemAbstract—Accession No. 958599-31-0, Chemical Abstracts Service, Columbus, Ohio, Source: Emory MLSC database, Dec. 2007.
ChemAbstract—Accession No. 958625-83-7, Chemical Abstracts Service, Columbus, Ohio, Source: Emory MLSC database, Dec. 2007.
ChemAbstract—Accession No. 958629-14-6, Chemical Abstracts Service, Columbus, Ohio, Source: Emory MLSC database, Dec. 2007.
ChemAbstract—Accession No. 958629-22-6, Chemical Abstracts Service, Columbus, Ohio, Source: Emory MLSC database, Dec. 2007.
ChemAbstract—Accession No. 958629-39-5, Chemical Abstracts Service, Columbus, Ohio, Source: Emory MLSC database, Dec. 2007.
ChemAbstract—Accession No. 958696-32-7, Chemical Abstracts Service, Columbus, Ohio, Source: Emory MLSC database, Dec. 2007.
ChemAbstract—Accession No. 958696-39-4, Chemical Abstracts Service, Columbus, Ohio, Source: Emory MLSC database, Dec. 2007.
ChemAbstract—Accession No. 958700-63-5, Chemical Abstracts Service, Columbus, Ohio, Source: Emory MLSC database, Dec. 2007.
Gutkowska, et al, Acta Poloniae Pharmaceutica, 1982, 39, p. 61-64.
WO09017664 Published Feb. 5, 2009. Applicant: Vitae Pharmaceuticals, Inc. Inventor: D. A. Claremon et al. This foreign patent is over 25KB and will not upload using EFS. Also published as US Publication US2011015157 and US201025636.
International Search Report for PCT/EP2009/063913 mailed May 6, 2010.

* cited by examiner

UREA DERIVATIVES OF SUBSTITUTED NORTROPANES, MEDICAMENTS CONTAINING SUCH COMPOUNDS AND THEIR USE

The present invention relates to compounds derived from the following chemical scaffold which is structurally defined by the formula I

I wherein the groups $R^1$, $Y^1$ to $Y^4$, V, W, and X are as defined hereinafter, including the tautomers, the stereoisomers, the mixtures thereof, and the salts thereof. The invention further relates to pharmaceutical compositions containing a compound of formula I according to the invention as well as the use of a compound according to the invention for preparing a pharmaceutical composition for the treatment of metabolic disorders. In addition, the invention relates to processes for preparing a pharmaceutical composition as well as a compound according to the invention.

In the literature, compounds which have an inhibitory effect on the enzyme 11β-hydroxysteroid dehydrogenase (HSD) 1 are proposed for the treatment of the metabolic syndrome, in particular diabetes type 2, obesity, and dyslipidemia.

In connection with the invention the following documents may be considered:

WO 98/22462 discloses compounds of the general formula P—$R^2$-Q, where each of P and Q is independently a group of formula wherein $R^1$, $R^3$, and J are as defined therein, to combat and control insect pests.

WO 2008/000951 discloses compounds of the general formula wherein $R^3$, $R^4$, $R_{1a}$, $R_{1b}$, $R_{1c}$, $R_{1d}$, $R_{2a}$, $R_{2b}$, p and r are as defined therein, as modulators of the activity of the enzyme 11β-hydroxysteroid dehydrogenase (HSD) 1.

AIM OF THE INVENTION

The aim of the present invention is to find new nortropanes, particularly those which are active with regard to the enzyme 11β-hydroxysteroid dehydrogenase (HSD) 1. A further aim of the present invention is to discover nortropanes which have an inhibitory effect on the enzyme 11β-hydroxysteroid dehydrogenase (HSD) 1 in vitro and/or in vivo and possess suitable pharmacological and pharmacokinetic properties to use them as medicaments.

A further aim of the present invention is to provide new pharmaceutical compositions which are suitable for the prevention and/or treatment of metabolic disorders, particularly diabetes, obesity, and dyslipidemia.

Other aims of the present invention will become apparent to the skilled man directly from the foregoing and following remarks.

OBJECT OF THE INVENTION

In a first aspect the present invention relates to compounds which are structurally defined by the formula I

I wherein
$R^1$ denotes aryl or heteroaryl,
  while by aryl is meant phenyl or naphthyl and
  by heteroaryl is meant pyrrolyl, furanyl, thienyl, pyridinyl, indolyl, benzofuranyl, benzothiophenyl, quinolinyl, isoquinolinyl, or
  pyrrolyl, imidazolyl, furanyl, thienyl, pyridinyl in each of which one or two CH groups are replaced by N, or
  indolyl, benzofuranyl, benzothiophenyl, quinolinyl, or isoquinolinyl, where in each of them 1 to 3 CH are replaced by N,
  while in the above-mentioned N including heteroaryl groups one or two —N=CH— groups are optionally replaced by —NH—CO— and/or —N($C_{1-4}$-alkyl)-CO—, and
  while the above-mentioned polycyclic aryl and heteroaryl groups are optionally partially saturated, though, retaining an aromatic or heteroaromatic substructure that is attached to the carbonyl group in formula I,
    where in the partially saturated rings one or two $CH_2$ groups are optionally replaced independently of each other with O, S, NH, N($C_{1-4}$-alkyl), carbonyl, or sulfonyl,
  wherein the above-mentioned aryl, heteroaryl, partially saturated aryl and heteroaryl groups are optionally substituted with one or more, preferably one to four, substituents $R^2$,
  wherein all heteroaryl groups are attached to the nortropane scaffold in formula I via a carbon atom, $R^N$ independently of each other denotes hydrogen, $C_{1-6}$-alkyl, $C_{3-6}$-alkenyl, $C_{3-6}$-alkynyl, $C_{3-6}$-cycloalkyl, (het)aryl, $C_{1-4}$-alkylcarbonyl, $C_{1-4}$-alkyloxycarbonyl, $C_{1-4}$-alkylsulfonyl, (het)arylcarbonyl, (het)arylsulfonyl,
- wherein each alkyl, alkenyl, and alkynyl group is optionally mono- or polysubstituted with fluorine and optionally monosubstituted with hydroxy, $C_{1-4}$-alkoxy, $C_{1-4}$-alkylsulfanyl, $C_{1-4}$-alkylsulfinyl, $C_{1-4}$-alkylsulfonyl, amino, $C_{1-4}$-alkylamino, di-($C_{1-4}$-alkyl)amino, $C_{1-4}$-alkylcarbonylamino, cyano, carboxy, $C_{1-4}$-alkoxycarbonyl, aminocarbonyl, $C_{1-4}$-alkylaminocarbonyl, di-($C_{1-4}$-alkyl)aminocarbonyl, or (het)aryl, $R^2$ independently of each other denotes halogen, nitro, cyano, hydroxy, $C_{3-6}$-cycloalkyl, $C_{3-6}$-cycloalkyloxy, tetrahydrofuran-3-yloxy, tetrahydropyran-3-yloxy, tetrahydropyran-4-yloxy, tetrahydrofuranyl-$C_{1-3}$-alkyloxy, tetrahydropyranyl-$C_{1-3}$-alkyloxy, (het)aryl, (het)aryloxy,
- $C_{1-6}$-alkyl, $C_{2-6}$-alkenyl, $C_{2-6}$-alkynyl, $C_{1-6}$-alkyloxy, $C_{1-6}$-alkylamino, where in each group one $CH_2$ group is optionally replaced with carbonyl or sulfonyl, and wherein each group is optionally mono or polyfluorinated and optionally additionally substituted with
    - hydroxy, chlorine, $C_{1-3}$-alkyloxy, amino, $C_{1-3}$-alkylamino, di-($C_{1-3}$-alkyl)-amino, pyrrolidin-1-yl, 2-oxo-pyrrolidin-1-yl, piperidin-1-yl, 2-oxo-piperidin-1-yl, morpholin-4-yl, 3-oxo-morpholin-4-yl, piperazin-1-yl, 2-oxo-piperazin-1-yl, 3-oxo-piperazin-1-yl, 4-($C_{1-3}$-alkyl)piperazin-1-yl, 2-oxo-4-($C_{1-3}$-alkyl)-piperazin-1-yl, 3-oxo-4-($C_{1-3}$-alkyl)piperazin-1-yl, carboxy, $C_{1-3}$-alkyloxycarbonyl, cyano, aminocarbonyl, $C_{1-3}$-alkylaminocarbonyl, di-($C_{1-3}$-alkyl)-aminocarbonyl, pyrrolidin-1-ylcarbonyl, piperidin-1-ylcarbonyl, morpholin-4-ylcarbonyl, piperazin-1-ylcarbonyl, 4-($C_{1-3}$-alkyl)piperazin-1-ylcarbonyl, $C_{1-4}$-alkylcarbonylamino, N—($C_{1-3}$-alkyl)-$C_{1-4}$-alkylcarbonylamino, arylcarbonylamino, $C_{1-3}$-alkylsulfanyl, $C_{1-3}$-alkylsulfinyl, $C_{1-3}$-alkylsulfonyl, $C_{3-6}$-cycloalkyl, tetrahydrofuranyl, tetrahydropyranyl, (het)aryl, or (het)aryloxy,
- amino, di-($C_{1-3}$-alkyl)amino, pyrrolidin-1-yl, 2-oxo-pyrrolidin-1-yl, piperidin-1-yl, 2-oxo-piperidin-1-yl, morpholin-4-yl, 3-oxo-morpholin-4-yl, piperazin-1-yl, 2-oxo-piperazin-1-yl, 3-oxo-piperazin-1-yl, 4-($C_{1-3}$-alkyl)piperazin-1-yl, 4-($C_{1-4}$-alkylcarbonyl)-piperazin-1-yl, 4-($C_{3-6}$-cycloalkylcarbonyl)-piperazin-1-yl, 4-($C_{1-4}$-alkyloxycarbonyl)-piperazin-1-yl, 4-($C_{1-4}$-alkylsulfonyl)-piperazin-1-yl, 2-oxo-4-($C_{1-3}$-alkyl)piperazin-1-yl, 3-oxo-4-($C_{1-3}$-alkyl)-piperazin-1-yl,
- (het)arylcarbonylamino, $C_{1-4}$-alkyloxycarbonylamino, aminocarbonylamino, $C_{1-4}$-alkylaminocarbonylamino, (het)arylaminocarbonylamino, di-($C_{1-3}$-alkyl)aminocarbonylamino, pyrrolidin-1-ylcarbonylamino, piperidin-1-ylcarbonylamino, morpholin-4-ylcarbonylamino, piperazin-1-ylcarbonylamino, 4-($C_{1-3}$-alkyl)-piperazin-1-ylcarbonylamino, aminosulfonylamino, $C_{1-3}$-alkylaminosulfonylamino, di-($C_{1-3}$-alkyl)aminosulfonylamino, pyrrolidin-1-ylsulfonylamino, piperidin-1-ylsulfonylamino, morpholin-4-ylsulfonylamino, piperazin-1-ylsulfonylamino, 4-($C_{1-3}$-alkyl)-piperazin-1-ylsulfonylamino, ($C_{1-3}$-alkyloxycarbonylamino)carbonylamino, (het)arylsulfonylamino,
- N—($C_{1-3}$-alkyl)-$C_{1-4}$-alkylcarbonylamino, N—($C_{1-3}$-alkyl)-(het)arylcarbonylamino, N—($C_{1-3}$-alkyl)-(het)aryl-$C_{1-3}$-alkylcarbonylamino, N—($C_{1-3}$-alkyl)-$C_{1-3}$-alkyloxycarbonylamino, N-(aminocarbonyl)-$C_{1-3}$-alkylamino, N—($C_{1-3}$-alkylaminocarbonyl)-$C_{1-3}$-alkylamino, N-[di-($C_{1-3}$-alkyl)aminocarbonyl]-$C_{1-3}$-alkylamino,
- N—($C_{1-3}$-alkyl)-$C_{1-3}$-alkylsulfonylamino, N—($C_{1-3}$-alkyl)-(het)arylsulfonylamino, N—($C_{1-3}$-alkyl)-(het)aryl-$C_{1-3}$-alkylsulfonylamino,
- carboxy, $C_{1-3}$-alkyloxycarbonyl, aminocarbonyl, $C_{1-3}$-alkylaminocarbonyl, di-($C_{1-3}$-alkyl)-aminocarbonyl, azetidin-1-ylcarbonyl, pyrrolidin-1-ylcarbonyl, piperidin-1-ylcarbonyl, morpholin-4-ylcarbonyl, piperazin-1-ylcarbonyl, 4-($C_{1-3}$-alkyl)-piperazin-1-ylcarbonyl, (het)arylaminocarbonyl, N—($C_{1-3}$-alkyl)-(het)arylaminocarbonyl, (het)aryl-$C_{1-3}$-alkylaminocarbonyl, N—($C_{1-3}$-alkyl)-(het)aryl-$C_{1-3}$-alkylaminocarbonyl, (het)arylcarbonyl,
- $C_{1-3}$-alkylsulfanyl, $C_{1-3}$-alkysulfinyl, (het)arylsulfonyl, trifluoromethylsulfanyl, trifluoromethylsulfinyl,
- aminosulfonyl, $C_{1-3}$-alkylaminosulfonyl, di-($C_{1-3}$-alkyl)-aminosulfonyl, pyrrolidin-1-ylsulfonyl, piperidin-1-ylsulfonyl, morpholin-4-ylsulfonyl, piperazin-1-ylsulfonyl, 4-($C_{1-3}$-alkyl)-piperazin-1-ylsulfonyl,
- wherein all the above-mentioned saturated heterocycloalkyl and cycloalkyl rings are optionally substituted with one or two groups independently selected from fluorine, $C_{1-3}$-alkyl, $C_{1-3}$-alkoxy, $C_{1-3}$-alkoxy-$C_{1-3}$-alkyl, and hydroxy, V is $CY^5Y^6$, O, or $NR^N$,
W is absent, $CY^7Y^8$, or $(CY^7Y^8)$—$(CY^9Y^{10})$,
X is absent, $CY^{11}Y^{12}$, or $(CY^{11}Y^{12})$—$(CY^{13}Y^{14})$,
V and W may also be combined to form a $C_{3-6}$-cycloalkyl group that is annelated via two adjacent carbon atoms to the aza-cycle and in which one or two $CH_2$ groups are optionally replaced independently of each other by O, S, $NR^N$, carbonyl, or sulfonyl and which is optionally partially unsaturated and optionally mono- or polysubstituted, preferably mono- to tetrasubstituted, with substituents independently of each other selected from $R^3$,
V and W may also be combined to form an (het)aryl group that is annelated via two adjacent carbon atoms to the aza-cycle,
$R^3$ denotes halogen, $C_{1-4}$-alkyl, cyano, carboxy, $C_{1-4}$-alkyloxycarbonyl, aminocarbonyl, $C_{1-3}$-alkylaminocarbonyl, di-($C_{1-3}$-alkyl)-aminocarbonyl, hydroxy, $C_{1-4}$-alkoxy, amino, $C_{1-3}$-alkylamino, di-($C_{1-3}$-alkyl)-amino, $C_{1-4}$-alkylcarbonylamino, N—$C_{1-3}$-alkyl-$C_{1-4}$-alkylcarbonylamino, and (het)aryl, wherein each alkyl group mentioned above is optionally mono- or polysubstituted with fluorine, and optionally monosubstituted with hydroxy, $C_{1-4}$-alkoxy, $C_{1-4}$-alkylsulfanyl, $C_{1-4}$-alkylsulfinyl, $C_{1-4}$-alkylsulfonyl, amino, $C_{1-4}$-alkylamino, di-($C_{1-4}$-alkyl)amino, $C_{1-4}$-alkylcarbonylamino, cyano, carboxy, $C_{1-4}$-alkoxycarbonyl, aminocarbonyl, $C_{1-4}$-alkylaminocarbonyl, di-($C_{1-4}$-alkyl)-aminocarbonyl, or (het)aryl,
$Y^1$ to $Y^{14}$, which may be identical and/or different, independently of each other denote hydrogen, halogen, nitro, cyano, hydroxy, $C_{3-6}$-cycloalkyl, $C_{3-6}$-cycloalkyloxy, tetrahydrofuran-3-yloxy, tetrahydropyran-3-yloxy, tetrahydropyran-4-yloxy, tetrahydrofuranyl-$C_{1-3}$-alkyloxy, tetrahydropyranyl-$C_{1-3}$-alkyloxy, (het)aryl, (het)aryloxy,
- $C_{1-6}$-alkyl, $C_{2-6}$-alkenyl, $C_{2-6}$-alkynyl, $C_{1-6}$-alkyloxy, $C_{1-6}$-alkylamino, where in each group one $CH_2$ group is optionally replaced by carbonyl or sulfonyl, and wherein each group is optionally mono- or polyfluorinated, and wherein each group is optionally additionally substituted with
    - hydroxy, chlorine, $C_{1-3}$-alkyloxy, amino, $C_{1-3}$-alkylamino, di-($C_{1-3}$-alkyl)-amino, pyrrolidin-1-yl, 2-oxo-pyrrolidin-1-yl, piperidin-1-yl, 2-oxo-piperidin-1-yl, morpholin-4-yl, 3-oxo-morpholin-4-yl, piperazin-1-yl, 2-oxo-piperazin-1-yl, 3-oxo-piperazin-1-yl, 4-($C_{1-3}$-alkyl)piperazin-1-yl, 2-oxo-4-($C_{1-3}$-alkyl)-piperazin-1-yl, 3-oxo-4-($C_{1-3}$-alkyl)piperazin-1-yl, carboxy, $C_{1-3}$-alkyloxy-carbonyl, cyano, aminocarbonyl, $C_{1-3}$-alkylaminocarbonyl, di-($C_{1-3}$-alkyl)-aminocarbonyl, pyrrolidin-1-ylcarbonyl, piperidin-1-ylcarbonyl, morpholin-4-ylcarbonyl, piperazin-1-ylcarbonyl, 4-($C_{1-3}$-alkyl)piperazin-1-ylcarbonyl, $C_{1-3}$-alkylcarbonylamino, (het)arylcarbonylamino, $C_{1-3}$-alkylsulfanyl, $C_{1-3}$-alkylsulfinyl, $C_{1-3}$-alkylsulfonyl, $C_{3-6}$-cycloalkyl, (het)aryl, or (het)aryloxy;

amino, di-($C_{1-3}$-alkyl)amino, pyrrolidin-1-yl, 2-oxo-pyrrolidin-1-yl, piperidin-1-yl, 2-oxo-piperidin-1-yl, morpholin-4-yl, 3-oxo-morpholin-4-yl, piperazin-1-yl, 2-oxo-piperazin-1-yl, 3-oxo-piperazin-1-yl, 4-($C_{1-3}$-alkyl)piperazin-1-yl, 4-($C_{1-4}$-alkylcarbonyl)-piperazin-1-yl, 4-($C_{3-6}$-cycloalkylcarbonyl)-piperazin-1-yl, 4-($C_{1-4}$-alkyloxycarbonyl)-piperazin-1-yl, 4-($C_{1-4}$-alkylsulfonyl)-piperazin-1-yl, 2-oxo-4-($C_{1-3}$-alkyl)piperazin-1-yl, 3-oxo-4-($C_{1-3}$-alkyl)-piperazin-1-yl, (het)arylcarbonylamino, $C_{1-4}$-alkyloxycarbonylamino, aminocarbonylamino, $C_{1-4}$-alkylaminocarbonylamino, (het)arylaminocarbonylamino, di-($C_{1-3}$-alkyl)aminocarbonylamino, pyrrolidin-1-ylcarbonylamino, piperidin-1-ylcarbonylamino, morpholin-4-ylcarbonylamino, piperazin-1-ylcarbonylamino, 4-($C_{1-3}$-alkyl)-piperazin-1-ylcarbonylamino, aminosulfonylamino, $C_{1-3}$-alkylaminosulfonylamino, di-($C_{1-3}$-alkyl)aminosulfonylamino, pyrrolidin-1-ylsulfonylamino, piperidin-1-ylsulfonylamino, morpholin-4-ylsulfonylamino, piperazin-1-ylsulfonylamino, 4-($C_{1-3}$-alkyl)-piperazin-1-ylsulfonylamino, ($C_{1-3}$-alkyloxycarbonylamino)carbonylamino, (het)arylsulfonylamino, N—($C_{1-3}$-alkyl)-$C_{1-3}$-alkylcarbonylamino, N—($C_{1-3}$-alkyl)-(het)arylcarbonylamino, N—($C_{1-3}$-alkyl)-(het)aryl-$C_{1-3}$-alkylcarbonylamino, N—($C_{1-3}$-alkyl)-$C_{1-3}$-alkyloxycarbonylamino, N-(aminocarbonyl)-$C_{1-3}$-alkylamino, N—($C_{1-3}$-alkyl-aminocarbonyl)-$C_{1-3}$-alkylamino, N-[di($C_{1-3}$-alkyl)aminocarbonyl]-$C_{1-3}$-alkylamino, N—($C_{1-3}$-alkyl)-$C_{1-3}$-alkylsulfonylamino, N—($C_{1-3}$-alkyl)-(het)arylsulfonylamino, N—($C_{1-3}$-alkyl)-(het)aryl-$C_{1-3}$-alkylsulfonylamino, carboxy, $C_{1-3}$-alkyloxycarbonyl, aminocarbonyl, $C_{1-3}$-alkylaminocarbonyl, di-($C_{1-3}$-alkyl)-aminocarbonyl, azetidin-1-ylcarbonyl, pyrrolidin-1-ylcarbonyl, piperidin-1-ylcarbonyl, morpholin-4-ylcarbonyl, piperazin-1-ylcarbonyl, 4-($C_{1-3}$-alkyl)-piperazin-1-ylcarbonyl, (het)arylaminocarbonyl, N—($C_{1-3}$-alkyl)-(het)arylaminocarbonyl, (het)aryl-$C_{1-3}$-alkylaminocarbonyl, N—($C_{1-3}$-alkyl)-(het)aryl-$C_{1-3}$-alkylaminocarbonyl, (het)arylcarbonyl, $C_{1-3}$-alkylsulfanyl, $C_{1-3}$-alkysulfinyl, (het)arylsulfonyl, trifluoromethylsulfanyl, trifluoromethylsulfinyl, aminosulfonyl, $C_{1-3}$-alkylaminosulfonyl, di-($C_{1-3}$-alkyl)-aminosulfonyl, pyrrolidin-1-ylsulfonyl, piperidin-1-ylsulfonyl, morpholin-4-ylsulfonyl, piperazin-1-ylsulfonyl, 4-($C_{1-3}$-alkyl)-piperazin-1-ylsulfonyl, wherein the above-mentioned saturated heterocycloalkyl and cycloalkyl rings are optionally substituted with one or two groups independently selected from fluorine, $C_{1-3}$-alkyl, $C_{1-3}$-alkoxy, $C_{1-3}$-alkoxy-$C_{1-3}$-alkyl, or hydroxy, and two groups Y, that are attached to the same carbon atom, such as $Y^1/Y^2$, $Y^3/Y^4$, $Y^5/Y^6$, $Y^7/Y^8$, $Y^9/Y^{10}$, $Y^{11}/Y^{12}$, $Y^{13}/Y^{14}$, may form combined with the carbon atom they are attached to a carbonyl group or a $C_{3-6}$-cycloalkyl group in which one or two $CH_2$ groups are optionally replaced independently of each other by O, S, $NR^N$, carbonyl, or sulfonyl and which is optionally partially unsaturated and optionally mono- or polysubstituted, preferably mono- to tetrasubstituted, with substituents independently of each other selected from $R^3$, and/or one of the pairs $Y^1$ and $Y^3$, $Y^1$ and $Y^5$, $Y^3$ and $Y^5$, $Y^1$ and $Y^7$, or $Y^7$ and $Y^{11}$ may be combined to form a $C_{1-3}$-alkylene bridge in which one or two $CH_2$ groups are optionally replaced independently of each other by O, S, $NR^N$, carbonyl, or sulfonyl and which is optionally partially unsaturated and optionally mono- or polysubstituted, preferably mono- to tetrasubstituted, with substituents independently of each other selected from $R^3$, and/or the residues $Y^1$, $Y^3$ and $Y^5$ are optionally linked to form a $C_{3-6}$-alkylene bridge in which one $CH_2$ group is optionally replaced by O, S, $NR^N$, carbonyl, or sulfonyl and one CH group optionally by N and which is optionally mono- or polysubstituted, preferably mono- to tetrasubstituted, with substituents independently of each other selected from $R^3$, $R^{10}$ independently of each other denotes halogen, $C_{1-3}$-alkyl, difluoromethyl, trifluoromethyl, cyano, nitro, amino, $C_{1-3}$-alkylamino, di-($C_{1-3}$-alkyl)amino, acetylamino, methylsulfonylamino, carboxy, $C_{1-4}$-alkyloxycarbonyl, aminocarbonyl, $C_{1-3}$-alkylaminocarbonyl, di-($C_{1-3}$-alkyl)aminocarbonyl, aminosulfonyl, methylsulfanyl, methylsulfinyl, methylsulfonyl, hydroxy, $C_{1-3}$-alkyloxy, difluoromethoxy, trifluoromethoxy, or phenyl optionally substituted with 1 or 2 substituents independently of each other selected from fluorine, methyl, methoxy, cyano, or hydroxy, while the above-mentioned (het)aryl is phenyl, naphthyl, pyrrolyl, furanyl, thienyl, pyridyl, indolyl, benzofuranyl, benzothiophenyl, quinolinyl, isoquinolinyl, or pyrrolyl, furanyl, thienyl, pyridyl in which 1 or 2 CH are replaced by N, or indolyl, benzofuranyl, benzothiophenyl, quinolinyl, isoquinolinyl in which 1 to 3 CH are replaced by N, or 1,2-dihydro-2-oxo-pyridinyl, 1,4-dihydro-4-oxo-pyridinyl, 2,3-dihydro-3-oxo-pyridazinyl, 1,2,3,6-tetrahydro-3,6-dioxo-pyridazinyl, 1,2-dihydro-2-oxo-pyrimidinyl, 3,4-dihydro-4-oxo-pyrimidinyl, 1,2,3,4-tetrahydro-2,4-dioxo-pyrimidinyl, 1,2-dihydro-2-oxo-pyrazinyl, 1,2,3,4-tetrahydro-2,3-dioxo-pyrazinyl, 2,3-dihydro-2-oxo-indolyl, 2,3-dihydrobenzofuranyl, 2,3-dihydro-2-oxo-1H-benzimidazolyl, 2,3-dihydro-2-oxo-benzoxazolyl, 1,2-dihydro-2-oxo-quinolinyl, 1,4-dihydro-4-oxo-quinolinyl, 1,2-dihydro-1-oxo-isoquinolinyl, 1,4-dihydro-4-oxo-cinnolinyl, 1,2-dihydro-2-oxo-quinazolinyl, 1,4-dihydro-4-oxo-quinazolinyl, 1,2,3,4-tetrahydro-2,4-dioxo-quinazolinyl, 1,2-dihydro-2-oxoquinoxalinyl, 1,2,3,4-tetrahydro-3-oxo-quinoxalinyl, 1,2,3,4-tetrahydro-2,3-dioxo-quinoxalinyl, 1,2-dihydro-1-oxo-phthalazinyl, 1,2,3,4-tetrahydro-1,4-dioxo-phthalazinyl, chromanyl, coumarinyl, 2,3-dihydro-benzo[1,4]dioxinyl, 3,4-dihydro-3-oxo-2H-benzo[1,4]oxazinyl, and wherein the above-mentioned (het)aryl groups are optionally substituted with one to three $R^{10}$ which may be identical or different, whilst the above-mentioned alkyl or alkylene moieties may be branched or unbranched, the tautomers thereof, the stereoisomers thereof, the mixtures thereof, and the salts thereof.

The compounds of general formula I according to the invention and the physiologically acceptable salts thereof have valuable pharmacological properties, particularly an inhibitory effect on the enzyme 11β-hydroxysteroid dehydrogenase (HSD) 1.

A further aspect of the invention also relates to the physiologically acceptable salts of the compounds of general formula I according to this invention with inorganic or organic acids.

A further aspect of the invention also relates to the physiologically acceptable salts of the compounds of general formula I according to this invention with inorganic or organic bases.

In a further aspect this invention relates to pharmaceutical compositions, containing at least one compound of general formula I or a physiologically acceptable salt according to the invention, optionally together with one or more inert carriers and/or diluents.

In a further aspect this invention relates to the compounds according to general formula I or the physiologically acceptable salts thereof for treatment or prevention of diseases or conditions which can be influenced by inhibiting the enzyme 11β-hydroxysteroid dehydrogenase (HSD) 1, such as metabolic disorders.

In a further aspect this invention relates to the use of at least one compound according to general formula I or one of the physiologically acceptable salts thereof for preparing a pharmaceutical composition which is suitable for the treatment or prevention of diseases or conditions which can be influenced by inhibiting the enzyme 11β-hydroxysteroid dehydrogenase (HSD) 1, such as metabolic disorders.

In a further aspect the present invention relates to a process for preparing the compounds of general formula I, characterized in that
an amine of general formula III

wherein the group $R^1$ is defined as hereinbefore and hereinafter,
or an amine of general formula IV

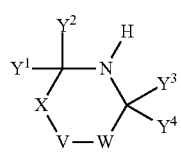

wherein the groups $Y^1$ to $Y^4$, V, W, and X are defined as hereinbefore and hereinafter,
is reacted with a carbonic acid derivative of the general formula Y—CO—Y, yielding a compound either of general formula V or VI as intermediate

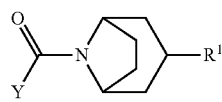

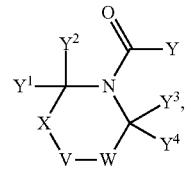

wherein the groups $R^1$, $Y^1$ to $Y^4$, V, W, and X are defined as hereinbefore and hereinafter and
wherein Y is a leaving group and in particular denotes fluorine, chlorine, bromine, cyano, $C_{1-9}$-alkoxy, $C_{2-6}$-alkenyloxy, $C_{2-6}$-alkynyloxy, aryloxy, heteroaryloxy, $C_{1-8}$-alkylsulfanyl, heteroar-N-yl, arylotriazol-1-yloxy, heteroarylotriazol-1-yloxy, 3-methyl-imidazol-1-yl, succinyl-N-oxy, di-($C_{1-4}$-alkyl)aminocarbonyloxy, pyrrol-1-ylcarbonyloxy, piperidin-1-ylcarbonyloxy, morpholin-4-ylcarbonyloxy, arylsulfanyl, or heteroarylsulfanyl,
while the alkyl, alkenyl, and alkynyl groups mentioned in the definition of the above group are optionally substituted with one or more substituents, preferably with one to five substituents, independently of each other selected from fluorine, chlorine, $C_{1-3}$-alkyl, or $C_{1-3}$-alkoxy,
while the aryl groups mentioned in the definition of the above group denote phenyl or naphthyl and the heteroaryl groups mentioned in the definition of the above group denote pyridinyl, pyrimidinyl, triazinyl, imidazolyl, pyrazolyl, triazolyl, tetrazolyl, whilst both the aryl and heteroaryl groups are optionally substituted with one or more substituents, preferably with one to five, independently of each other selected from fluorine, chlorine, bromine, $C_{1-3}$-alkyl, $C_{1-3}$-alkyloxy, nitro, cyano, or di-($C_{1-3}$-alkyl)amino,
while the two Y in Y—CO—Y may be identical or different,
while the second Y to be replaced may also be transformed into a more reactive Y after the first Y is replaced with one of the two amines,
while the intermediates of general formula V and VI are optionally isolated and optionally purified, before being subsequently reacted with the other amine of the general formula III or IV to yield a compound of the general formula I;
the reactions are conducted optionally in the presence of an organic base such as an amine, e.g. ethyldiisopropylamine, triethylamine, imidazole, or pyridine, or an inorganic base, e.g. potassium carbonate or calcium oxide, and/or an additive, such as 4-dimethylaminopyridine or 1-hydroxybenzotriazol, preferably between −10 and 120° C. in solvents preferably selected from tetrahydrofuran, 1,2-dimethoxyethane, ether, 1,4-dioxane, N,N-dimethylformamide, N,N-dimethylacetamide, N-methylpyrrolidinone, acetonitrile, ethyl acetate, dichloromethane, 1,2-dichloroethane, toluene, benzene, and hexanes, but also aqueous and alcoholic solutions may be usable for some of the combinations listed above;
and, if necessary any protective group used in the reactions described above is cleaved concurrently or subsequently;
if desired a compound of general formula I thus obtained is resolved into its stereoisomers;
if desired a compound of general formula I thus obtained is converted into the salts thereof, particularly for pharmaceutical use into the physiologically acceptable salts thereof.

DETAILED DESCRIPTION OF THE INVENTION

Unless otherwise stated, the groups, residues, and substituents, particularly $R^1$ to $R^3$, $R^{10}$, $R^N$, $Y^1$ to $Y^{14}$, V, W, and X are defined as above and hereinafter. If residues, substituents, or groups occur several times in a compound they may have the same or different meanings. Some preferred meanings of groups and substituents of the compounds according to the invention will be given hereinafter.

Preferred embodiments of the invention are characterized by the following definitions:

a) Definitions ($a^i$) for $R^1$ in the order of preference, ascending from preferably ($a^1$) to more preferably ($a^2$) up to most preferably ($a^4$):

($a^1$): Preferably, $R^1$ denotes phenyl, naphthyl, pyrrolyl, furanyl, thienyl, pyridinyl, indolyl,
benzofuranyl, benzothiophenyl, quinolinyl, isoquinolinyl, or
pyrrolyl, furanyl, thienyl, pyridinyl wherein 1 or 2 CH are replaced by N, or
indolyl, benzofuranyl, benzothiophenyl, quinolinyl, isoquinolinyl, wherein 1 or 2 CH are replaced by N, or
indolinyl, 2-oxo-2,3-dihydro-indolyl, 1-oxo-2,3-dihydro-isoindolyl, 2-oxo-2,3-dihydrobenzoimidazolyl, pyrazolo[1,5-a]pyrimidinyl, 7-oxo-4,7-dihydro-pyrazolo[1,5-a]pyrimidinyl, [1,2,4]triazolo[1,5-a]pyrimidinyl, 4-oxo-3,4-dihydro-quinazolinyl, tetrahydroquinolinyl,
wherein the above-mentioned aryl and heteroaryl groups are optionally substituted with one to four different and/or identical substituents $R^2$, and
wherein all heteroaryl groups are attached to the nortropane scaffold via a carbon atom.

($a^2$): More preferably, $R^1$ denotes phenyl, naphthyl, pyridinyl, pyridazinyl, pyrazinyl, pyrimidinyl, furanyl, thienyl, oxazolyl, isoxazolyl, thiazolyl, isothiazolyl, all of which are optionally substituted with one to four substituents independently of each other selected from $R^2$.

($a^3$): Even more preferably, $R^1$ denotes phenyl, naphthyl, furanyl, pyridinyl, isoxazolyl, pyrimidinyl, all of which are optionally substituted with one or two substituents independently of each other selected from $R^2$.

($a^4$): Most preferably, $R^1$ denotes phenyl, which is optionally substituted with one substituent selected from $R^2$.

b) Definitions ($b^i$) for $R^N$ in the order of preference, ascending from preferably ($b^1$) to more preferably ($b^2$) up to most preferably ($b^4$):

($b^1$): Preferably, $R^N$ denotes hydrogen, $C_{1-6}$-alkyl, $C_{3-6}$-alkenyl, $C_{3-6}$-cycloalkyl, phenyl-$C_{1-3}$-alkyl, $C_{1-4}$-alkylcarbonyl, phenylcarbonyl, $C_{1-4}$-alkyloxycarbonyl, phenyl, $C_{1-4}$-alkylsulfonyl, phenylsulfonyl, wherein each alkyl group is optionally mono- or polysubstituted with fluorine and optionally monosubstituted with hydroxy, $C_{1-4}$-alkoxy, $C_{1-4}$-alkylcarbonylamino, cyano, carboxy, $C_{1-4}$-alkoxycarbonyl, aminocarbonyl, $C_{1-3}$-alkylaminocarbonyl, di-($C_{1-3}$-alkyl)aminocarbonyl or phenyl, and wherein each phenyl group is optionally monosubstituted with $R^{10}$.

($b^2$): More preferably, $R^N$ denotes hydrogen, $C_{1-6}$-alkyl, $C_{3-6}$-cycloalkyl, phenyl-$C_{1-2}$-alkyl, $C_{1-3}$-alkylcarbonyl, phenylcarbonyl, $C_{1-3}$-alkyloxycarbonyl, phenyl, $C_{1-3}$-alkylsulfonyl, phenylsulfonyl, wherein each alkyl group is optionally mono- or polysubstituted with fluorine and optionally monosubstituted with hydroxy, $C_{1-3}$-alkoxy, cyano, or phenyl, and wherein each phenyl group is optionally monosubstituted with $R^{10}$.

($b^3$): Even more preferably, $R^N$ denotes hydrogen, $C_{1-4}$-alkyl, $C_{5-6}$-cycloalkyl, phenylmethyl, $C_{1-3}$-alkylcarbonyl, $C_{1-3}$-alkyloxycarbonyl, phenyl, $C_{1-3}$-alkylsulfonyl, wherein each alkyl group is optionally mono- or polysubstituted with fluorine and optionally monosubstituted with hydroxy, $C_{1-3}$-alkoxy, cyano, or phenyl, and wherein each phenyl group is optionally monosubstituted with $R^{10}$.

($b^4$): Most preferably, $R^N$ denotes hydrogen, methyl, phenylmethyl, acetyl, and methylsulfonyl.

c) Definitions ($c^i$) for $R^2$ in the order of preference, ascending from preferably ($c^1$) to more preferably ($c^2$) up to most preferably ($c^4$):

($c^1$): Preferably, $R^2$ denotes fluorine, chlorine, cyano, hydroxy, $C_{1-4}$-alkyloxy, difluoromethyl, trifluoromethyl, difluoromethoxy, trifluoromethoxy, $C_{3-6}$-cycloalkyl, $C_{3-6}$-cycloalkyloxy, $C_{3-6}$-cycloalkyl-$C_{1-3}$-alkyl, $C_{3-6}$-cycloalkyl-$C_{1-3}$-alkyloxy, tetrahydrofuran-3-yloxy, tetrahydropyran-3-yloxy, tetrahydropyran-4-yloxy, tetrahydrofuranyl-$C_{1-3}$-alkyloxy, tetrahydropyranyl-$C_{1-3}$-alkyloxy, (het)aryl, (het)aryloxy, (het)aryl-$C_{1-3}$-alkyl, (het)aryl-$C_{1-3}$-alkyloxy, (het)aryloxy-$C_{1-3}$-alkyl, $C_{1-3}$-alkylcarbonyl, (het)aryl-carbonyl,
amino, $C_{1-3}$-alkylamino, di-($C_{1-3}$-alkyl)amino, pyrrolidin-1-yl, 2-oxo-pyrrolidin-1-yl, piperidin-1-yl, 2-oxo-piperidin-1-yl, morpholin-4-yl, 3-oxo-morpholin-4-yl, 3-oxo-piperazin-1-yl, 4-($C_{1-4}$-alkylcarbonyl)-piperazin-1-yl,
$C_{1-3}$-alkylcarbonylamino, (het)aryl-carbonylamino, $C_{1-3}$-alkyloxycarbonylamino, $C_{1-3}$-alkylaminocarbonylamino, di-($C_{1-3}$-alkyl)aminocarbonylamino, pyrrolidin-1-ylcarbonylamino, piperidin-1-ylcarbonylamino, morpholin-4-ylcarbonylamino, $C_{1-3}$-alkylsulfonylamino, $C_{1-3}$-alkylamino-sulfonylamino, di-($C_{1-3}$-alkyl)amino-sulfonylamino, pyrrolidin-1-ylsulfonylamino, piperidin-1-ylsulfonylamino, morpholin-4-ylsulfonylamino, (het)arylsulfonylamino,
N—($C_{1-3}$-alkyl)-$C_{1-3}$-alkylcarbonylamino, N—($C_{1-3}$-alkyl)-(het)arylcarbonylamino, N—($C_{1-3}$-alkyl)-$C_{1-3}$-alkyloxycarbonylamino, N—($C_{1-3}$-alkyl-aminocarbonyl)-$C_{1-3}$-alkylamino, N-[di($C_{1-3}$-alkyl)aminocarbonyl]-$C_{1-3}$-alkylamino,
N—($C_{1-3}$-alkyl)-$C_{1-3}$-alkylsulfonylamino, N—($C_{1-3}$-alkyl)-(het)arylsulfonylamino,
carboxy, $C_{1-3}$-alkyloxycarbonyl, aminocarbonyl, $C_{1-3}$-alkylaminocarbonyl, di-($C_{1-3}$-alkyl)-aminocarbonyl, pyrrolidin-1-ylcarbonyl, piperidin-1-ylcarbonyl, morpholin-4-ylcarbonyl,
carboxy-$C_{1-3}$-alkyl, $C_{1-3}$-alkyloxycarbonyl-$C_{1-3}$-alkyl, cyano-$C_{1-3}$-alkyl, aminocarbonyl$C_{1-3}$-alkyl, $C_{1-3}$-alkylaminocarbonyl-$C_{1-3}$-alkyl, di-($C_{1-3}$-alkyl)-aminocarbonyl-$C_{1-3}$-alkyl, pyrrolidin-1-ylcarbonyl-$C_{1-3}$-alkyl, piperidin-1-ylcarbonyl-$C_{1-3}$-alkyl, morpholin-4-ylcarbonyl-$C_{1-3}$-alkyl,
carboxy-$C_{1-3}$-alkyloxy, $C_{1-3}$-alkyloxycarbonyl-$C_{1-3}$-alkyloxy, cyano-$C_{1-3}$-alkyloxy, aminocarbonyl-$C_{1-3}$-alkyloxy, $C_{1-3}$-alkylaminocarbonyl-$C_{1-3}$-alkyloxy, di-($C_{1-3}$-alkyl)aminocarbonyl-$C_{1-3}$-alkyloxy, pyrrolidin-1-ylcarbonyl-$C_{1-3}$-alkyloxy, piperidin-1-ylcarbonyl-$C_{1-3}$-alkyloxy, morpholin-4-ylcarbonyl-$C_{1-3}$-alkyloxy,
hydroxy-$C_{1-3}$-alkyl, $C_{1-3}$-alkyloxy-$C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, pyrrolidin-1-yl-$C_{1-3}$-alkyl, 2-oxo-pyrrolidin-1-yl-$C_{1-3}$-alkyl, $C_{1-3}$-alkylcarbonylamino-$C_{1-3}$-alkyl, N—($C_{1-3}$-alkyl)-$C_{1-4}$-alkylcarbonylamino-$C_{1-3}$-alkyl, 2-oxo-piperidin-1-yl-$C_{1-3}$-alkyl, 3-oxo-morpholin-4-yl-$C_{1-3}$-alkyl,
hydroxy-$C_{2-3}$-alkyloxy, $C_{1-3}$-alkyloxy-$C_{2-3}$-alkyloxy, $C_{1-3}$-alkylsulfinyl-$C_{1-3}$-alkyloxy, $C_{1-3}$-alkylsulfonyl-$C_{1-3}$-alkyloxy, di-($C_{1-3}$-alkyl)amino-$C_{1-3}$-alkyloxy, 2-oxo-pyrrolidin-1-yl-$C_{2-3}$-alkyloxy, 2-oxo-piperidin-1-yl-$C_{2-3}$-alkyloxy, morpholin-4-yl-$C_{2-3}$-alkyloxy, 3-oxo-morpholin-4-yl-$C_{2-3}$-alkyloxy, aminosulfonyl, $C_{1-3}$-alkylaminosulfonyl, di-($C_{1-3}$-alkyl)aminosulfonyl, pyrrolidin-1-ylsulfonyl, piperidin-1-ylsulfonyl, morpholin-4-ylsulfonyl, wherein the above-mentioned (het)aryl is defined as described hereinbefore and hereinafter.

($c^2$): More preferably, $R^2$ denotes fluorine, chlorine, cyano, $C_{1-4}$-alkyl, hydroxy, $C_{1-4}$-alkyloxy, trifluoromethyl, difluoromethoxy, trifluoromethoxy, $C_{3-6}$-cycloalkyloxy, tetrahydrofuran-3-yloxy, tetrahydropyran-3-yloxy, tetrahydropyran-4-yloxy, tetrahydrofuranyl-$C_{1-3}$-alkyloxy, tetrahydropyranyl-$C_{1-3}$-alkyloxy, (het)aryl, (het)aryloxy, (het)aryl-$C_{1-3}$-alkyloxy, $C_{1-3}$-alkyl-carbonyl, amino, $C_{1-3}$-alkylamino, 2-oxo-pyrrolidin-1-yl, 2-oxo-piperidin-1-yl, morpholin-4-yl, 3-oxo-morpholin-4-yl, $C_{1-3}$-alkylcarbonylamino, (het)aryl-carbonylamino, $C_{1-3}$-alkylsulfonylamino, N—($C_{1-3}$-alkyl)-$C_{1-3}$-alkyl-carbonylamino, N—($C_{1-3}$-alkyl)-(het)arylcarbonylamino, N—($C_{1-3}$-alkyl)-$C_{1-3}$-alkylsulfonylamino, N—($C_{1-3}$-alkyl)-(het)arylsulfonylamino, carboxy, $C_{1-3}$-alkyloxycarbonyl, aminocarbonyl, $C_{1-3}$-alkylaminocarbonyl, di-($C_{1-3}$-alkyl)aminocarbonyl, pyrrolidin-1-yl-carbonyl, piperidin-1-ylcarbonyl, morpholin-4-ylcarbonyl, carboxy-$C_{1-3}$-alkyl, $C_{1-3}$-alkyloxycarbonyl-$C_{1-3}$-alkyl, cyano-$C_{1-3}$-alkyl, aminocarbonyl$C_{1-3}$-alkyl, $C_{1-3}$-alkylaminocarbonyl-$C_{1-3}$-alkyl, di-($C_{1-3}$-alkyl)-aminocarbonyl-$C_{1-3}$-alkyl, pyrrolidin-1-ylcarbonyl-$C_{1-3}$-alkyl, piperidin-1-ylcarbonyl-$C_{1-3}$-alkyl, morpholin-4-ylcarbonyl-$C_{1-3}$-alkyl, cyano-$C_{1-3}$-alkyloxy, aminocarbonyl-$C_{1-3}$-alkyloxy, $C_{1-3}$-alkylaminocarbonyl-$C_{1-3}$-alkyloxy, di-($C_{1-3}$-alkyl)aminocarbonyl-$C_{1-3}$-alkyloxy, pyrrolidin-1-ylcarbonyl-$C_{1-3}$-alkyloxy, piperidin-1-ylcarbonyl-$C_{1-3}$-alkyloxy, morpholin-4-ylcarbonyl-$C_{1-3}$-alkyloxy, hydroxy-$C_{1-3}$-alkyl, $C_{1-3}$-alkyloxy-$C_{1-3}$-alkyl, $C_{1-3}$-alkyl-carbonylamino-$C_{1-3}$-alkyl, N—($C_{1-3}$-alkyl)-$C_{1-3}$-alkyl-carbonylamino-$C_{1-3}$-alkyl, 2-oxo-pyrrolidin-1-yl-$C_{1-3}$-alkyl, 2-oxo-piperidin-1-yl-$C_{1-3}$-alkyl, 3-oxo-morpholin-4-yl-$C_{1-3}$-alkyl, hydroxy-$C_{2-3}$-alkyloxy, $C_{1-3}$-alkyloxy-$C_{2-3}$-alkyloxy, aminosulfonyl, $C_{1-3}$-alkylaminosulfonyl, di-($C_{1-3}$-alkyl)aminosulfonyl, wherein the above-mentioned (het)aryl groups are selected from the group consisting of phenyl, furanyl, thienyl, oxazolyl, thiazolyl, isoxazolyl, imidazolyl, pyrazolyl, oxadiazolyl, triazolyl, tetrazolyl, pyridinyl, pyrimidinyl, pyrazinyl, pyridazinyl, and triazinyl, wherein each (het)aryl group is optionally mono- or disubstituted with identical or different $R^{10}$.

($c^3$): Even more preferably, $R^2$ denotes fluorine, chlorine, $C_{1-3}$-alkyl, hydroxy, $C_{1-3}$-alkyloxy, methylcarbonylamino, methylsulfonylamino, cyano, carboxy, $C_{1-3}$-alkyloxycarbonyl, aminocarbonyl, methylaminocarbonyl, dimethylaminocarbonyl, hydroxy-$C_{1-3}$-alkyl, methoxy$C_{1-3}$-alkyl, methylcarbonylamino-$C_{1-3}$-alkyl, hydroxy-$C_{2-3}$-alkyloxy, methoxy-$C_{2-3}$-alkyloxy, trifluoromethyl, difluoromethoxy, trifluoromethoxy, aminosulfonyl, methylaminosulfonyl, dimethylaminosulfonyl, phenoxy or phenyl, wherein each phenyl group is optionally monosubstituted with $R^{10}$.

($c^4$): Most preferably, $R^2$ denotes fluorine, methyl, isopropyl, methoxy, trifluoromethoxy, phenoxy, methoxycarbonyl, methoxymethyl.

d) Definitions (d) for V, W, and X in the order of preference, ascending from preferably ($d^1$) to more preferably ($d^2$) up to most preferably ($d^3$):

($d^1$): Preferably, V is $CY^5Y^6$, O, or $NR^N$, W is absent or $CY^7Y^8$, and X is absent or $CY^{11}Y^{12}$, or X is absent or $CY^{11}Y^{12}$ and V and W are combined to form a $C_{5-6}$-cycloalkyl group that is annelated via two adjacent carbon atoms to the aza-cycle and in which one or two $CH_2$ groups are optionally replaced independently of each other by O, $NR^3$, carbonyl, and/or sulfonyl and which is optionally mono-, di- or trisubstituted independently of each other with substituents selected from $R^3$, or X is absent or $CY^{11}Y^{12}$ and V and W are combined to form a benzo, pyrido, pyrimido, pyrazino, pyridazino, pyrrolo, furo, thieno, oxazolo, isoxazolo, imidazo, pyrazolo, thiazolo, or isothiazolo ring that is annelated via two adjacent carbon atoms to the aza-cycle and which is optionally additionally substituted with one, two, or three substituents independently selected from $R^{10}$.

($d^2$): More preferably, V is $CY^5Y^6$, O, or $NR^N$, W is absent or $CY^7Y^8$, and X is absent or $CY^{11}Y^{12}$, or X is absent or $CY^{11}Y^{12}$ and V and W are combined to form a $C_{5-6}$-cycloalkyl group that is annelated via two adjacent carbon atoms to the aza-cycle and in which one or two $CH_2$ groups are optionally replaced independently of each other by O, $NR^3$, and/or carbonyl, and which is optionally mono- or disubstituted independently of each other with substituents selected from $R^3$, or X is absent or $CY^{11}Y^{12}$ and V and W are combined to form a benzo, pyrido, furo, thieno, oxazolo, isoxazolo, imidazo, pyrazolo, thiazolo, or isothiazolo ring that is annelated via two adjacent carbon atoms to the aza-cycle and which is optionally additionally substituted with one or two substituents independently selected from $R^{10}$.

($d^3$): Most preferably, V is $CY^5Y^6$ or O, W is $CY^7Y^8$, and X is absent or $CY^{11}Y^{12}$, or X is $CY^{11}Y^{12}$ and V and W are combined to form a thieno or imidazo ring that is annelated via two adjacent carbon atoms to the aza-cycle and which is optionally additionally substituted with one substituent selected from $R^{10}$.

e) Definitions ($e^i$) for $R^3$ in the order of preference, ascending from preferably ($e^1$) to more preferably ($e^2$) up to most preferably ($e^4$):

($e^1$): Preferably, $R^3$ denotes fluorine, chlorine, $C_{1-4}$-alkyl, trifluoromethyl, cyano, carboxy, $C_{1-4}$-alkyloxycarbonyl, aminocarbonyl, $C_{1-3}$-alkylaminocarbonyl, di-($C_{1-3}$-alkyl)-aminocarbonyl, hydroxy, $C_{1-4}$-alkoxy, trifluoromethoxy, $C_{1-3}$-alkylcarbonylamino, and (het)aryl, wherein each alkyl group mentioned above is optionally monosubstituted with hydroxy, $C_{1-4}$-alkoxy, $C_{1-4}$-alkylcarbonylamino, cyano, $C_{1-4}$-alkoxycarbonyl, aminocarbonyl, $C_{1-4}$-alkylamino-carbonyl, di($C_{1-4}$-alkyl)aminocarbonyl, or (het)aryl, ($e^2$): More preferably, $R^3$ denotes fluorine, chlorine, $C_{1-4}$-alkyl, trifluoromethyl, cyano, carboxy, $C_{1-4}$-alkyloxycarbonyl, aminocarbonyl, $C_{1-3}$-alkylaminocarbonyl, di-($C_{1-3}$-alkyl)-aminocarbonyl, hydroxy, $C_{1-4}$-alkoxy, trifluoromethoxy, $C_{1-3}$-alkylcarbonylamino, cyano-$C_{1-3}$-alkoxy, $C_{1-4}$-alkoxycarbonyl-$C_{1-3}$-alkoxy, hydroxy-$C_{1-3}$-alkyl, hydroxy-$C_{2-3}$-alkoxy, $C_{1-3}$-alkoxy-$C_{2-3}$-alkoxy, phenyl, phenylmethyl, wherein each phenyl group is optionally monosubstituted with $R^{10}$.

($e^3$): Even more preferably, $R^3$ denotes fluorine, $C_{1-3}$-alkyl, trifluoromethyl, cyano, carboxy, $C_{1-3}$-alkyloxycarbonyl, aminocarbonyl, $C_{1-3}$-alkylaminocarbonyl, di-($C_{1-3}$-alkyl)-aminocarbonyl, hydroxy, $C_{1-3}$-alkoxy, trifluoromethoxy, $C_{1-3}$-alkylcarbonylamino, hydroxy-$C_{1-3}$-alkyl, phenyl, phenylmethyl, wherein each phenyl group is optionally monosubstituted with $R^{10}$.

($e^4$): Most preferably, $R^3$ denotes fluorine, methyl, cyano, hydroxy, methoxy, acetylamino.

f) Definitions (f') for $Y^1$ to $Y^{14}$, which are identical or different, in the order of preference, ascending from preferably (f$^1$) to more preferably (f$^2$) up to most preferably (f$^4$):

(f$^1$) Preferably, $Y^1$ to $Y^{14}$ independently of each other denote hydrogen, fluorine, chlorine, cyano, hydroxy, $C_{1-6}$-alkyl, $C_{1-4}$-alkyloxy, difluoromethyl, trifluoromethyl, difluoromethoxy, trifluoromethoxy, $C_{3-6}$-cycloalkyl, $C_{3-6}$-cycloalkyloxy, $C_{3-6}$-cycloalkyl-$C_{1-3}$-alkyl, $C_{3-6}$-cycloalkyl-$C_{1-3}$-alkyloxy, (het)aryl, (het)aryloxy, (het)aryl-$C_{1-3}$-alkyl, amino, $C_{1-3}$-alkylamino, (het)aryl-$C_{1-3}$-alkylamino, di-($C_{1-3}$-alkyl)amino, pyrrolidin-1-yl, 2-oxo-pyrrolidin-1-yl, piperidin-1-yl, 2-oxo-piperidin-1-yl, morpholin-4-yl, 3-oxo-morpholin-4-yl, piperazin-1-yl, 2-oxo-piperazin-1-yl, 3-oxo-piperazin-1-yl, 4-($C_{1-3}$-alkyl)-piperazin-1-yl, 4-($C_{1-4}$-alkylcarbonyl)-piperazin-1-yl, 4-($C_{3-6}$-cycloalkylcarbonyl)piperazin-1-yl, 4-($C_{1-4}$-alkyloxycarbonyl)-piperazin-1-yl, 4-($C_{1-4}$-alkylsulfonyl)piperazin-1-yl, 2-oxo-4-($C_{1-3}$-alkyl)piperazin-1-yl, 3-oxo-4-($C_{1-3}$-alkyl)piperazin-1-yl, $C_{1-3}$-alkylcarbonylamino, (het)arylcarbonylamino, (het)aryl-$C_{1-3}$-alkylcarbonylamino, $C_{1-4}$-alkyloxycarbonylamino, aminocarbonylamino, $C_{1-4}$-alkylaminocarbonylamino, (het)aryl-aminocarbonylamino, di-($C_{1-3}$-alkyl)aminocarbonylamino, pyrrolidin-1-ylcarbonylamino, piperidin-1-ylcarbonylamino, morpholin-4-ylcarbonylamino, piperazin-1-ylcarbonylamino, 4-($C_{1-3}$-alkyl)piperazin-1-ylcarbonylamino, $C_{1-3}$-alkylsulfonylamino, aminosulfonylamino, $C_{1-3}$-alkylaminosulfonylamino, alkyl)aminosulfonylamino, pyrrolidin-1-ylsulfonylamino, piperidin-1-ylsulfonylamino, morpholin-4-ylsulfonylamino, piperazin-1-ylsulfonylamino, 4-($C_{1-3}$-alkyl)-piperazin-1-ylsulfonylamino, ($C_{1-3}$-alkyloxy-carbonylamino)carbonylamino, (het)arylsulfonylamino, (het)aryl-$C_{1-3}$-alkylsulfonylamino, N—($C_{1-3}$-alkyl)-$C_{1-3}$-alkylcarbonylamino, N—($C_{1-3}$-alkyl)-(het)arylcarbonylamino, N—($C_{1-3}$-alkyl)-(het)aryl-$C_{1-3}$-alkylcarbonylamino, N—($C_{1-3}$-alkyl)-$C_{1-3}$-alkyloxycarbonylamino, N-(aminocarbonyl)-$C_{1-3}$-alkylamino, N—($C_{1-3}$-alkyl-aminocarbonyl)-$C_{1-3}$-alkylamino, N-[di($C_{1-3}$-alkyl)aminocarbonyl]-$C_{1-3}$-alkylamino, N—($C_{1-3}$-alkyl)-$C_{1-3}$-alkylsulfonylamino, N—($C_{1-3}$-alkyl)-(het)arylsulfonylamino, N—($C_{1-3}$-alkyl)-(het)aryl-$C_{1-3}$-alkylsulfonylamino, carboxy, $C_{1-3}$-alkyloxycarbonyl, aminocarbonyl, $C_{1-3}$-alkylaminocarbonyl, di-($C_{1-3}$-alkyl)-aminocarbonyl, azetidin-1-ylcarbonyl, pyrrolidin-1-ylcarbonyl, piperidin-1-ylcarbonyl, morpholin-4-ylcarbonyl, piperazin-1-ylcarbonyl, 4-($C_{1-3}$-alkyl)-piperazin-1-ylcarbonyl, (het)arylaminocarbonyl, N—($C_{1-3}$-alkyl)-(het)arylaminocarbonyl, (het)aryl-$C_{1-3}$-alkylaminocarbonyl, N—($C_{1-3}$-alkyl)-(het)aryl-$C_{1-3}$-alkylaminocarbonyl, carboxy-$C_{1-3}$-alkyl, $C_{1-3}$-alkyloxycarbonyl-$C_{1-3}$-alkyl, cyano-$C_{1-3}$-alkyl, aminocarbonyl$C_{1-3}$-alkyl, $C_{1-3}$-alkylaminocarbonyl-$C_{1-3}$-alkyl, di-($C_{1-3}$-alkyl)-aminocarbonyl-$C_{1-3}$-alkyl, pyrrolidin-1-yl-carbonyl-$C_{1-3}$-alkyl, piperidin-1-ylcarbonyl-$C_{1-3}$-alkyl, morpholin-4-ylcarbonyl-$C_{1-3}$-alkyl, piperazin-1-ylcarbonyl-$C_{1-3}$-alkyl, 4-($C_{1-3}$-alkyl)-piperazin-1-ylcarbonyl-$C_{1-3}$-alkyl, carboxy-$C_{1-3}$-alkyloxy, $C_{1-3}$-alkyloxycarbonyl-$C_{1-3}$-alkyloxy, cyano-$C_{1-3}$-alkyloxy, aminocarbonyl-$C_{1-3}$-alkyloxy, $C_{1-3}$-alkylaminocarbonyl-$C_{1-3}$-alkyloxy, di-($C_{1-3}$-alkyl)aminocarbonyl-$C_{1-3}$-alkyloxy, pyrrolidin-1-ylcarbonyl-$C_{1-3}$-alkyloxy, piperidin-1-ylcarbonyl-$C_{1-3}$-alkyloxy, morpholin-4-ylcarbonyl-$C_{1-3}$-alkyloxy, piperazin-1-ylcarbonyl-$C_{1-3}$-alkyloxy, 4-($C_{1-3}$-alkyl)piperazin-1-ylcarbonyl-$C_{1-3}$-alkyloxy, hydroxy-$C_{1-3}$-alkyl, $C_{1-3}$-alkyloxy-$C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, pyrrolidin-1-yl-$C_{1-3}$-alkyl, 2-oxo-pyrrolidin-1-yl-$C_{1-3}$-alkyl, piperidin-1-yl-$C_{1-3}$-alkyl, 2-oxo-piperidin-1-yl-$C_{1-3}$-alkyl, morpholin-4-yl-$C_{1-3}$-alkyl, 3-oxo-morpholin-4-yl-$C_{1-3}$-alkyl, piperazin-1-yl-$C_{1-3}$-alkyl, 2-oxo-piperazin-1-yl-$C_{1-3}$-alkyl, 3-oxo-piperazin-1-yl-$C_{1-3}$-alkyl, 4-($C_{1-3}$-alkyl)piperazin-1-yl-$C_{1-3}$-alkyl, 2-oxo-4-($C_{1-3}$-alkyl)-piperazin-1-yl-$C_{1-3}$-alkyl, 3-oxo-4-($C_{1-3}$-alkyl)piperazin-1-yl-$C_{1-3}$-alkyl, $C_{1-3}$-alkylcarbonylamino-$C_{1-3}$-alkyl, (het)arylcarbonylamino-$C_{1-3}$-alkyl, hydroxy-$C_{2-3}$-alkyloxy, $C_{1-3}$-alkyloxy-$C_{1-3}$-alkyloxy, $C_{1-3}$-alkylsulfanyl-$C_{1-3}$-alkyloxy, $C_{1-3}$-alkylsulfinyl-$C_{1-3}$-alkyloxy, $C_{1-3}$-alkylsulfonyl-$C_{1-3}$-alkyloxy, amino-$C_{1-3}$-alkyloxy, $C_{1-3}$-alkylamino-$C_{1-3}$-alkyloxy, di-($C_{1-3}$-alkyl)amino-$C_{1-3}$-alkyloxy, pyrrolidin-1-yl-$C_{1-3}$-alkyloxy, 2-oxo-pyrrolidin-1-yl-$C_{1-3}$-alkyloxy, piperidin-1-yl-$C_{1-3}$-alkyloxy, 2-oxo-piperidin-1-yl-$C_{1-3}$-alkyloxy, morpholin-4-yl-$C_{1-3}$-alkyloxy, 3-oxo-morpholin-4-yl-$C_{1-3}$-alkyloxy, piperazin-1-yl-$C_{1-3}$-alkyloxy, 2-oxo-piperazin-1-yl-$C_{1-3}$-alkyloxy, 3-oxo-piperazin-1-yl-$C_{1-3}$-alkyloxy, 4-($C_{1-3}$-alkyl)piperazin-1-yl-$C_{1-3}$-alkyloxy, 2-oxo-4-($C_{1-3}$-alkyl)-piperazin-1-yl-$C_{1-3}$-alkyloxy, 3-oxo-4-($C_{1-3}$-alkyl)piperazin-1-yl-$C_{1-3}$-alkyloxy, $C_{1-3}$-alkylsulfanyl, $C_{1-3}$-alkylsulfinyl, $C_{1-3}$-alkylsulfonyl, (het)arylsulfonyl, wherein the above-mentioned saturated heterocycloalkyl and cycloalkyl rings are optionally substituted with one or two groups independently of each other selected from fluorine, $C_{1-3}$-alkyl, $C_{1-3}$-alkoxy, $C_{1-3}$-alkoxy-$C_{1-3}$-alkyl, or hydroxy, and wherein the above-mentioned (het)aryl is phenyl, naphthyl, pyrrolyl, furanyl, thienyl, pyridyl, indolyl, benzofuranyl, benzothiophenyl, quinolinyl, isoquinolinyl, or pyrrolyl, furanyl, thienyl, pyridyl in which 1 or 2 CH are replaced by N, or indolyl, benzofuranyl, benzothiophenyl, quinolinyl, isoquinolinyl in which 1 to 3 CH are each replaced by N, and wherein the above-mentioned (het)aryl groups are optionally substituted with one or two substituents selected from $R^{10}$ which may be identical or different, and/or two groups Y, that are attached to the same carbon atom, such as $Y^1/Y^2$, $Y^3/Y^4$, $Y^5/Y^6$, $Y^7/Y^8$, $Y^9/Y^{10}$, $Y^{11}/Y^{12}$, $Y^{13}/Y^{14}$, form combined with the carbon atom they are attached to a carbonyl group or a $C_{5-6}$-cycloalkyl group in which one or two $CH_2$ groups are optionally replaced independently of each other by O, S, $NR^N$, carbonyl, or sulfonyl and which is optionally partially unsaturated and optionally mono-, di-, or trisubstituted with substituents independently of each other selected from $R^3$, and/or one of the pairs $Y^1$ and $Y^3$, $Y^1$ and $Y^5$, $Y^3$ and $Y^5$, $Y^1$ and $Y^7$, or $Y^7$ and $Y^{11}$ is combined to form a $C_{2-3}$-alkylene bridge in which one or two $CH_2$ groups are optionally replaced independently of each other by O, S, $NR^N$, carbonyl, or sulfonyl and which is optionally partially unsaturated and optionally mono-, di-, or trisubstituted with substituents independently of each other selected from $R^3$, and/or the residues $Y^1$, $Y^3$ and $Y^5$ are linked to form a $C_{4-6}$-alkylene bridge in which one $CH_2$ group is optionally replaced by O, S, $NR^N$, carbonyl, or sulfonyl and one CH group by N and which is optionally mono-, di-, or trisubstituted with substituents independently of each other selected from $R^3$.

(f²) More preferably, $Y^1$ to $Y^{14}$ independently of each other denote hydrogen, fluorine, chlorine, cyano, hydroxy, $C_{1-4}$-alkyl, $C_{1-4}$-alkyloxy, trifluoromethyl, trifluoromethoxy, (het)aryl, (het)aryloxy, (het)aryl-$C_{1-3}$-alkyl,
  2-oxo-pyrrolidin-1-yl, 2-oxo-piperidin-1-yl, morpholin-4-yl, 3-oxo-morpholin-4-yl, piperazin-1-yl, 2-oxo-piperazin-1-yl, 3-oxo-piperazin-1-yl, 4-($C_{1-3}$-alkyl)piperazin-1-yl, 4-($C_{1-3}$-alkylcarbonyl)-piperazin-1-yl, 4-($C_{1-4}$-alkyloxycarbonyl)-piperazin-1-yl, 4-($C_{1-3}$-alkylsulfonyl)-piperazin-1-yl, 2-oxo-4-($C_{1-3}$-alkyl)piperazin-1-yl, 3-oxo-4-($C_{1-3}$-alkyl)piperazin-1-yl,
  $C_{1-3}$-alkylcarbonylamino, (het)arylcarbonylamino, $C_{1-3}$-alkylsulfonylamino,
  N—($C_{1-3}$-alkyl)-$C_{1-3}$-alkyl-carbonylamino, N—($C_{1-3}$-alkyl)-(het)arylcarbonylamino, N—($C_{1-3}$-alkyl)-$C_{1-3}$-alkyl-sulfonylamino, N—($C_{1-3}$-alkyl)-(het)arylsulfonylamino,
  carboxy, $C_{1-3}$-alkyloxycarbonyl, aminocarbonyl, $C_{1-3}$-alkyl-aminocarbonyl, di-($C_{1-3}$-alkyl)-aminocarbonyl, azetidin-1-ylcarbonyl, pyrrolidin-1-ylcarbonyl, piperidin-1-ylcarbonyl, morpholin-4-ylcarbonyl, piperazin-1-ylcarbonyl, 4-($C_{1-3}$-alkyl)-piperazin-1-ylcarbonyl, (het)arylaminocarbonyl, N—($C_{1-3}$-alkyl)-(het)arylaminocarbonyl, (het)aryl-$C_{1-3}$-alkylaminocarbonyl, N—($C_{1-3}$-alkyl)-(het)aryl-$C_{1-3}$-alkylaminocarbonyl,
  carboxy-$C_{1-3}$-alkyl, $C_{1-3}$-alkyloxycarbonyl-$C_{1-3}$-alkyl, cyano-$C_{1-3}$-alkyl, aminocarbonyl$C_{1-3}$-alkyl, $C_{1-3}$-alkylaminocarbonyl-$C_{1-3}$-alkyl, di-($C_{1-3}$-alkyl)-aminocarbonyl-$C_{1-3}$-alkyl,
  carboxy-$C_{1-3}$-alkyloxy, $C_{1-3}$-alkyloxycarbonyl-$C_{1-3}$-alkyloxy, cyano-$C_{1-3}$-alkyloxy, aminocarbonyl-$C_{1-3}$-alkyloxy, $C_{1-3}$-alkylaminocarbonyl-$C_{1-3}$-alkyloxy, di-($C_{1-3}$-alkyl)aminocarbonyl-$C_{1-3}$-alkyloxy,
  hydroxy-$C_{1-3}$-alkyl, $C_{1-3}$-alkyloxy-$C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl,
  $C_{1-3}$-alkylcarbonylamino-$C_{1-3}$-alkyl, (het)arylcarbonylamino-$C_{1-3}$-alkyl,
  hydroxy-$C_{2-3}$-alkyloxy, $C_{1-3}$-alkyloxy-$C_{1-3}$-alkyloxy,
  $C_{1-3}$-alkylsulfanyl, $C_{1-3}$-alkylsulfinyl, $C_{1-3}$-alkylsulfonyl, (het)arylsulfonyl,
  wherein the above-mentioned saturated heterocycloalkyl and cycloalkyl rings are optionally substituted with one or two groups independently of each other selected from fluorine, $C_{1-3}$-alkyl, $C_{1-3}$-alkoxy, $C_{1-3}$-alkoxy-$C_{1-3}$-alkyl, or hydroxy, and
  wherein the above-mentioned (het)aryl is phenyl, naphthyl, pyrrolyl, furanyl, thienyl, pyridyl, indolyl, benzofuranyl, benzothiophenyl, quinolinyl, or isoquinolinyl, or pyrrolyl, furanyl, thienyl, pyridyl in which 1 or 2 CH are replaced by N, or indolyl, benzofuranyl, benzothiophenyl, quinolinyl, isoquinolinyl in which 1 to 3 CH are each replaced by N, and
  wherein the above-mentioned (het)aryl groups are optionally substituted with one or two $R^{10}$ which may be identical or different, and/or
  two groups Y, that are attached to the same carbon atom, such as $Y^1/Y^2$, $Y^3/Y^4$, $Y^5/Y^6$, $Y^7/Y^8$, $Y^9/Y^{10}$, $Y^{11}/Y^{12}$, $Y^{13}/Y^{14}$, form combined with the carbon atom they are attached to a carbonyl group or a $C_{5-6}$-cycloalkyl group in which one or two $CH_2$ groups are optionally replaced independently of each other by O, $NR^N$, carbonyl, or sulfonyl and which is optionally mono- or disubstituted with substituents independently of each other selected from $R^3$, and/or
  one of the pairs $Y^1$ and $Y^3$, $Y^1$ and $Y^5$, $Y^3$ and $Y^5$, $Y^1$ and $Y^7$, or $Y^7$ and $Y^{11}$ is combined to form a $C_{2-3}$-alkylene bridge in which one or two $CH_2$ groups are optionally replaced independently of each other by O, $NR^N$, carbonyl, or sulfonyl and which is optionally mono- or disubstituted with substituents independently of each other selected from $R^3$, and/or
  the residues $Y^1$, $Y^3$ and $Y^5$ are linked to form a $C_4$-alkylene bridge in which one $CH_2$ group is optionally replaced by O or $NR^N$ and which is optionally mono- or disubstituted with substituents independently of each other selected from $R^3$.

(f³) Even more preferably, $Y^1$ to $Y^{14}$ independently of each other denote hydrogen, fluorine, cyano, trifluoromethyl, hydroxy, $C_{1-3}$-alkyloxy, $C_{1-3}$-alkylcarbonylamino, carboxy, $C_{1-3}$-alkyloxy-carbonyl, aminocarbonyl, $C_{1-3}$-alkylaminocarbonyl, di-($C_{1-3}$-alkyl)-aminocarbonyl, hydroxy-$C_{1-3}$-alkyl, $C_{1-3}$-alkyloxy-$C_{2-3}$-alkyl, phenyl, phenoxy, wherein the mentioned phenyl groups are optionally substituted with one substituent $R^{10}$, and/or
  two groups Y, that are attached to the same carbon atom, such as $Y^1/Y^2$, $Y^3/Y^4$, $Y^5/Y^6$, $Y^7/Y^8$, $Y^9/Y^{10}$, $Y^{11}/Y^{12}$, $Y^{13}/Y^{14}$, form combined with the carbon atom they are attached to a carbonyl group, and/or
  the pair $Y^1$ and $Y^3$ is combined to form a $C_{2-3}$-alkylene bridge in which one or two $CH_2$ groups are optionally replaced independently of each other by O, $NR^N$, or carbonyl and which is optionally mono- or disubstituted with substituents independently of each other selected from $R^3$, or
  the residues $Y^1$, $Y^3$ and $Y^5$ are linked to form a $C_4$-alkylene bridge which is optionally mono- or disubstituted with substituents independently of each other selected from $R^3$.

(f⁴) Most preferably, $Y^1$ to $Y^{14}$ independently of each other denote hydrogen, methyl, trifluoromethyl, hydroxymethyl, 2-hydroxyprop-2-yl, hydroxy, methoxy, cyano, methoxycarbonyl, ethoxycarbonyl, aminocarbonyl, and/or the pair $Y^1$ and $Y^3$ is combined to form an ethylene bridge.

g) Definitions ($g^i$) for $R^{10}$ in the order of preference, ascending from preferably ($g^1$) to more preferably ($g^2$) up to most preferably ($g^3$):

($g^1$) Preferably, $R^{10}$ independently of each other denote fluorine, chlorine, bromine, $C_{1-3}$-alkyl, difluoromethyl, trifluoromethyl, cyano, nitro, amino, acetylamino, methylsulfonylamino, carboxy, $C_{1-4}$-alkyloxycarbonyl, aminocarbonyl, $C_{1-3}$-alkylaminocarbonyl, di-($C_{1-3}$-alkyl)-aminocarbonyl, aminosulfonyl, methylsulfanyl, methylsulfinyl, methylsulfonyl, phenyl, hydroxy, $C_{1-3}$-alkyloxy, difluoromethoxy, or trifluoromethoxy.

($g^2$) More preferably, $R^{10}$ denotes fluorine, chlorine, methyl, difluoromethyl, trifluoromethyl, cyano, hydroxy, methoxy, difluoromethoxy, or trifluoromethoxy.

($g^3$) Most preferably, $R^{10}$ denotes fluorine, methoxy, or methyl.

Each $a^i$, $b^i$, $c^i$, $d^i$, $e^i$, $f^i$, $g^i$ represents a characterized, individual embodiment for the corresponding substituent as described above. So given the above definitions, preferred individual embodiments of the first aspect of the invention are fully characterized by the term ($a^i b^i c^i d^i e^i f^i g^i$) if for each letter i in this term an individual figure is given. Indices i vary independently from each other. All individual embodiments described by the term in parentheses with full permutation of the indices i, referring to the above definitions, shall be comprised by the present invention.

The following Table 1 shows, exemplarily and in the order of increasing preference from the first line to the last line, such embodiments E-1 to E-18 of the invention that are considered preferred. This means that embodiment E-18, represented by the entries in the last row of Table 1 is the most preferred embodiment.

TABLE 1

Preferred embodiments E-1 to E-18 of the invention

| | $R^1$ | $R^N$ | $R^2$ | V/W/X | $R^3$ | $Y^1$ to $Y^{14}$ | $R^{10}$ |
|---|---|---|---|---|---|---|---|
| E-1  | $a^1$ | $b^1$ | $c^1$ | $d^1$ | $e^1$ | $f^1$ | $g^1$ |
| E-2  | $a^1$ | $b^2$ | $c^1$ | $d^2$ | $e^2$ | $f^2$ | $g^2$ |
| E-3  | $a^2$ | $b^3$ | $c^1$ | $d^2$ | $e^3$ | $f^2$ | $g^3$ |
| E-4  | $a^1$ | $b^3$ | $c^2$ | $d^2$ | $e^3$ | $f^2$ | $g^3$ |
| E-5  | $a^2$ | $b^4$ | $c^2$ | $d^2$ | $e^4$ | $f^2$ | $g^3$ |
| E-6  | $a^2$ | $b^4$ | $c^2$ | $d^3$ | $e^4$ | $f^2$ | $g^3$ |
| E-7  | $a^3$ | $b^4$ | $c^2$ | $d^3$ | $e^4$ | $f^2$ | $g^3$ |
| E-8  | $a^2$ | $b^4$ | $c^3$ | $d^2$ | $e^4$ | $f^2$ | $g^3$ |
| E-9  | $a^3$ | $b^4$ | $c^3$ | $d^2$ | $e^4$ | $f^2$ | $g^3$ |
| E-10 | $a^2$ | $b^4$ | $c^2$ | $d^2$ | $e^4$ | $f^3$ | $g^3$ |
| E-11 | $a^3$ | $b^4$ | $c^2$ | $d^2$ | $e^4$ | $f^3$ | $g^3$ |
| E-12 | $a^2$ | $b^4$ | $c^3$ | $d^2$ | $e^4$ | $f^3$ | $g^3$ |
| E-13 | $a^3$ | $b^4$ | $c^3$ | $d^2$ | $e^4$ | $f^3$ | $g^3$ |
| E-14 | $a^3$ | $b^4$ | $c^3$ | $d^2$ | $e^4$ | $f^4$ | $g^3$ |
| E-15 | $a^3$ | —* | $c^3$ | $d^3$ | —* | $f^4$ | $g^3$ |
| E-16 | $a^3$ | —* | $c^4$ | $d^3$ | —* | $f^4$ | $g^3$ |
| E-17 | $a^4$ | —* | $c^3$ | $d^3$ | —* | $f^4$ | $g^3$ |
| E-18 | $a^4$ | —* | $c^4$ | $d^3$ | —* | $f^4$ | $g^3$ |

—*means that the respective substituent does not exist in the corresponding embodiment including the tautomers, the stereoisomers, the mixtures, and the salts thereof.

Another preferred embodiment of this invention is described by the formula I.1

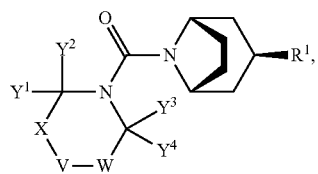

I.1 wherein the ethylene bridge and the residue $R^1$ are situated on the same face (cis→endo compound) of the piperidine ring and wherein the groups $R^1$, $Y^1$ to $Y^4$, V, W, and X are defined as hereinbefore and hereinafter, their tautomers, their stereoisomers, mixtures thereof, and the salts thereof.

Regarding the definitions of heteroaryl and (het)aryl in cases where they contain an N within their framework and the carbon atom adjacent to the nitrogen is substituted with a hydroxy group, then a tautomeric amide substructure may be formed and is part of the invention. Examples of such substructures of heteroaryl and (het)aryl groups wherein a tautomeric amide may be formed are depicted in the following compilation:

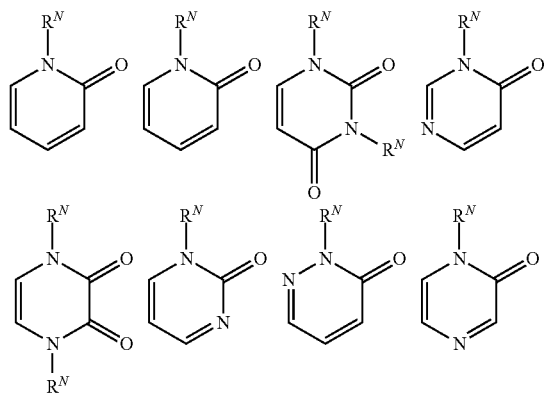

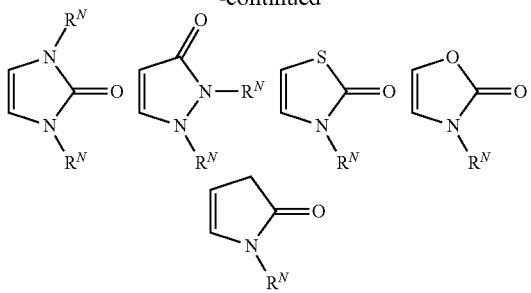

These tautomeric structures may be annelated to heteroaryl or (het)aryl groups of the meanings as described above.

Some terms used above and hereinafter to describe the compounds according to the invention will now be defined more closely.

The term "substituted" as used herein, means that any one or more hydrogens on the designated atom is replaced with a selection from the indicated group, provided that the designated atom's normal valence is not exceeded, and that the substitution results in a stable compound.

The term "partially unsaturated" as used herein, means that in the designated group or moiety 1, 2 or more, preferably 1 or 2, double bonds are present. Preferably as used herein, the term "partially unsaturated" does not cover fully unsaturated groups or moieties.

The term halogen denotes an atom selected from the group consisting of F, Cl, Br, and I.

The term $C_{1-n}$-alkyl, wherein n may have a value of 1 to 18, denotes a saturated, branched or unbranched hydrocarbon group with 1 to n C atoms. Examples of such groups include methyl, ethyl, n-propyl, iso-propyl, butyl, iso-butyl, sec-butyl, tert-butyl, n-pentyl, iso-pentyl, neo-pentyl, tert-pentyl, n-hexyl, iso-hexyl, etc.

The term $C_{2-n}$-alkenyl, wherein n has a value of 3 to 6, denotes a branched or unbranched hydrocarbon group with 2 to n C atoms and a C=C double bond. Examples of such groups include ethenyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl etc.

The term $C_{2-n}$-alkynyl, wherein n has a value of 3 to 6, denotes a branched or unbranched hydrocarbon group with 2 to n C atoms and a CC triple bond. Examples of such groups include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl etc. Unless otherwise stated alkynyl groups are connected to the remainder of the molecule via the C atom in position 1. Therefore terms such as 1-propynyl, 2-propynyl, 1-butynyl, etc. are equivalent to the terms 1-propyn-1-yl, 2-propyn-1-yl, 1-butyn-1-yl, etc. This also applies analogously to $C_{2-n}$-alkenyl groups.

The term $C_{1-n}$-alkoxy denotes a $C_{1-n}$-alkyl-0 group, wherein $C_{1-n}$-alkyl is as hereinbefore defined. Examples of such groups include methoxy, ethoxy, n-propoxy, iso-propoxy, nbutoxy, iso-butoxy, sec-butoxy, tert-butoxy, n-pentoxy, iso-pentoxy, neo-pentoxy, tertpentoxy, n-hexoxy, iso-hexoxy etc.

The term $C_{1-n}$-alkylcarbonyl denotes a $C_{1-n}$-alkyl-C(=O) group, wherein $C_{1-n}$-alkyl is as hereinbefore defined. Examples of such groups include methylcarbonyl, ethylcarbonyl, npropylcarbonyl, iso-propylcarbonyl, n-butylcarbonyl, iso-butylcarbonyl, sec-butylcarbonyl, tert-butylcarbonyl, n-pentylcarbonyl, iso-pentylcarbonyl, neo-pentylcarbonyl, tert-pentylcarbonyl, n-hexylcarbonyl, iso-hexylcarbonyl, etc.

The term $C_{3-n}$-cycloalkyl denotes a saturated mono-, bi-, tri- or spirocarbocyclic group with 3 to n C atoms. Examples of such groups include cyclopropyl, cyclobutyl, cyclopentyl, cyclohexyl, cycloheptyl, cyclooctyl, cyclononyl, cyclododecyl, bicyclo[3.2.1]octyl, spiro[4.5]decyl, norpinyl, norbonyl, norcaryl, adamantyl, etc. Preferably the term $C_{3-7}$-cycloalkyl denotes saturated monocyclic groups.

The term $C_{5-n}$-cycloalkenyl denotes a $C_{5-n}$-cycloalkyl group which is as hereinbefore defined and additionally has at least one unsaturated C=C double bond.

The term $C_{3-n}$-cycloalkylcarbonyl denotes a $C_{3-n}$-cycloalkyl-C(=O) group wherein $C_{3-n}$-cycloalkyl is as hereinbefore defined.

The term $C_{3-n}$-heterocycloalkyl denotes a saturated mono-, bi-, tri- or spirocarbocyclic group, which is as hereinbefore defined, with 3-m to n-m C atoms, wherein m carbon atoms are replaced with m heteroatoms independently selected from N, O, and S. Examples of such groups include aziridinyl, oxiranyl, azetidinyl, oxetanyl, pyrrolidinyl, tetrahydrofuranyl, tetrahydrothiophenyl, piperidinyl, tetrahydropyranyl, tetrahydrothiopyranyl, piperazinyl, morpholinyl, 1,3-dioxanyl, 1,4-dioxanyl, thiomorpholinyl, azepanyl, oxepanyl, thiepanyl, 1-aza-bicyclo[2.2.2]octane, 1,4-diaza-bicyclo[2.2.2] octane, etc. Preferably the term heterocycloalkyl denotes saturated monocyclic $C_{5-6}$-cycloalkyl groups wherein one or two carbon atoms are replaced with N and/or O.

The term tri-($C_{1-4}$-alkyl)silyl comprises silyl groups which have identical or two or three different alkyl groups.

The term di-($C_{1-3}$-alkyl)amino comprises amino groups which have identical or two different alkyl groups.

If groups or residues are optionally substituted, this applies to any form of the group or residue. For instance, if an alkyl group is optionally mono- or polyfluorinated this comprises also alkyl residues which are part of larger groups, e.g. alkyloxy, alkylcarbonyl, alkoxyalkyl, etc., or if a (het)aryl group is optionally mono- or polysubstituted with a certain substituent or a set of substituents this also includes (het)aryl groups which are part of larger groups, e.g. (het)aryl-$C_{1-n}$-alkyl, (het) aryloxy, (het)aryloxy-$C_{1-n}$-alkyl, (het)aryl-$C_{1-n}$-alkyloxy, etc. Accordingly, in cases where $Y^1$ to $Y^{14}$, $R^2$, $R^3$, or $R^N$ have e.g. the meaning (het)aryloxy, while (het)aryl residues are optionally mono- or polyfluorinated and (het)aryl denotes inter alia phenyl, the meanings mono-, di-, tri-, tetra-, and pentafluorophenoxy are also comprised. The same applies to groups or residues in which a part of the group or residue is replaced as e.g. a $CH_2$ group is optionally replaced with O, S, NR, CO, or $SO_2$. For instance, a residue having inter alia the meaning hydroxy-$C_{1-3}$-alkyl, in which a $CH_2$ group is optionally replaced by CO, this also comprises carboxy, carboxymethyl, hydroxymethylcarbonyl, carboxyethyl, hydroxylmethylcarbonylmethyl, and hydroxyethylcarbonyl.

All atoms/elements, including atoms that are part of a group, described herein comprise all stable isotopic forms of the respective element. For instance, whenever hydrogen is mentioned, either explicitly or as part of a group such as methyl, this includes hydrogen and deuterium as stable isotopic forms of the element hydrogen.

The compounds according to the invention may be obtained using methods of synthesis known in principle. Preferably the compounds are obtained by the following methods according to the invention which are described in more detail hereinafter.

Scheme 1 summarizes different approaches to prepare the nortropane skeleton from butan-1,4-dione or a cyclic congener thereof and 1,3-acetonedicarboxylic acid, acetoacetic acid ester, or derivatives thereof. Reactions 1.) and 3.) represent an example of combining succinaldehyde, 1,3-acetonedicarboxylic acid diester, or acetoacetic acid ester and an amine, e.g. a protected ammonia equivalent such as benzylamine or methylamine, to obtain 3-oxo-8-aza-bicyclo [3.2.1]octane-2,4-dicarboxylic acid diesters as intermediates. Reaction 1.) is preferably carried out in an alcohol, such as methanol, ethanol or benzylalcohol, or an aqueous solvent. Preferred co-solvents are N,N-dimethylformamide, N,N-dimethylacetamide, N-methylpyrrolidinone, dimethylsulfoxide, tetrahydrofuran, 1,4-dioxane, or 1,2-dimethoxyethane (see e.g. *J. Chem. Soc.* 1917, 111, 766; *Tetrahedron Asymmetry* 2002, 21, 2351-2358; U.S. Pat. No. 2,845,427 (1955) and U.S. Pat. No. 2,836,598 (1954); DE 352981 and DE 354950; and references quoted therein). The reactions may also be carried out without an additional solvent or in one of the co-solvents mentioned. The transformation may be conducted without an additive but often the presence of a base, such as sodium hydroxide, methoxide, or tert-butoxide, or an acid, such as hydrochloric acid, is advantageous or even essential. Using a base or an acid as additive may result in the direct formation of the N-substituted nortropanone depending on the alkyl ester used. The reactions are carried out at −30 to 160° C., preferably between −10 and 120° C. The carboxy groups may be removed after basic or acidic hydrolysis of the ester groups at temperatures between 10 and 140° C. Since the same solvents may be applied as for the preceding step, the reaction may be carried out in the same reaction vessel. Reaction 3.) may be conducted as described for 1.), preferably in the presence of an alkali metal hydroxide in an aqueous or alcoholic solution (see e.g. DE 345759). Equation 2.) shows an example using a dialkoxytetrahydrofuran as a succinaldehyde surrogate to prepare the nortropanone framework (see e.g. *J. Am. Chem. Soc.* 1952, 74, 3825-3828; *Helv. Chim. Acta* 1986, 69, 887-897; *J. Heterocycl. Chem.* 1992, 29, 1541-1544; *Helv. Chim. Acta* 2003, 86, 812-826; and citations quoted therein). These reactions are preferably carried out with 1,3-acetonedicarboxylic acid and an amine, such as e.g. benzylamine, methylamine, or 4-methoxyaniline, in water that may be combined with alcohols, e.g. methanol or ethanol, N,N-dimethylformamide, N,N-dimethylacetamide, N-methylpyrrolidinone, dimethylsulfoxide, tetrahydrofuran, 1,4-dioxane, or 1,2-dimethoxyethane. The overall transformation consists of three reaction steps, liberation of succinaldehyde from the precursor, reaction of succinaldehyde with the amine followed by the reaction with 1,3-acetonedicarboxylic acid (Mannich reaction) and eventually decarboxylation of the carboxyl groups. Accordingly, the reaction conditions, primarily the pH value of the solution, have to be adjusted over the course of the sequence. Liberation of succinaldehyde from the precursor is preferably achieved by the treatment with acid, e.g. hydrochloric acid, sulfuric acid, or phosphoric acid, at temperatures of −10 to 60° C. Then, the amine and 1,3-acetonedicarboxylic acid are added and the pH value of the solution is raised by the addition of additives, e.g. alkali metal acetate, citrate, phosphate, or hydrogenphosphate; this step is preferably conducted between −10 and 60° C. The eventual decarboxylation is achieved by increasing the temperature, preferably to 30 to 140° C.; lowering the pH value, using e.g. hydrochloric acid, may be advantageous. Nortropanone may also be prepared from N-protected 2,5-dialkoxypyrrolidine and a diene or an silylenol ether as exemplified in equations 4.) and 5.) (see e.g. *Chem. Commun.* 2002, 2626-2627; *Synlett* 2004, 143-145; and references quoted therein). These reactions are carried out under anhydrous conditions in an inert solvent such as dichloromethane, 1,2-dichloroethane, fluorinated hydrocarbons, ether, 1,4-dioxane, benzene, toluene, or hexane. The presence of a Lewis acid, such as e.g. trimethylsilyl triflate, boron trifluoride etherate, or a lanthanide triflate, is essential to promote the reactions. Preferably, the reactions are performed at temperatures between −78 and 100° C.

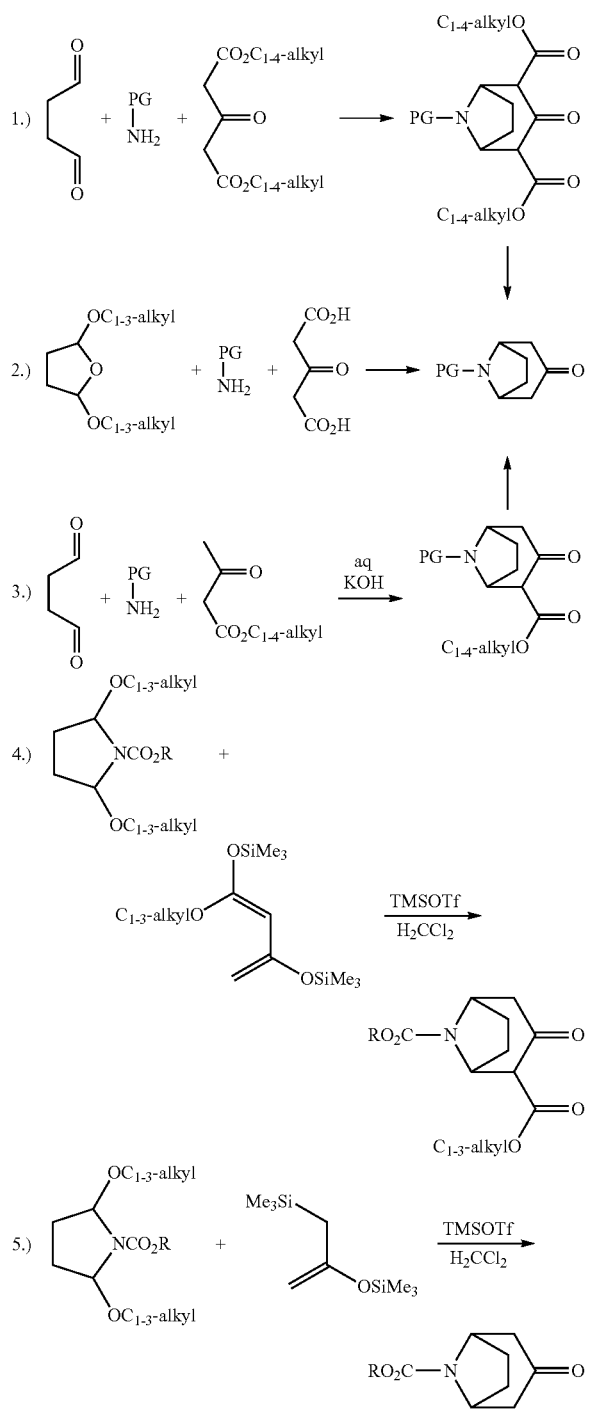

Another viable synthetic route to the nortropanone scaffold is delineated in Scheme 2. Key reaction is the addition of an amine, e.g. benzylamine, methylamine, 4-methoxyaniline, or hydroxylamine, to cycloheptadienone (see e.g. *J. Am. Chem. Soc.* 1989, 111, 4433-4440; *J. Am. Chem. Soc.* 2002, 124, 2245-2258; and references cited therein). This reaction is preferably carried out in an alcohol, e.g. methanol or ethanol, that may be combined with solvents such as water, dimethylsulfoxide, N,N-dimethylformamide, N,N-dimethylacetamide, N-methylpyrrolidinone, acetonitril, tetrahydrofuran, 1,4-dioxane, ether, or 1,2-dimethoxyethane, at temperatures ranging from 0 to 120° C. Beneficial additives may be bases such as e.g. potassium carbonate, calcium oxide, triethylamine, ethyldiisopropylamine, 1,8-diaza-bicyclo[5.4.0]undec-7-ene, or alkali metal alkoxides. Cyclohepta-2,6-dienone may be obtained from cycloheptanone as described (see e.g. *J. Am. Chem. Soc.* 2002, 124, 2245-2258 and references cited therein).

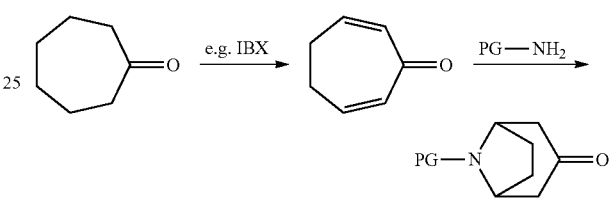

PG = protective group

Residue $R^1$ or a precursor of it may be introduced as described in Scheme 3. Addition of a magnesium halide or lithium derivative of $R^1$ to an optionally N-protected nortropanone delivers the corresponding nortropanol. This transformation is preferably conducted in tetrahydrofuran, ether, 1,4-dioxane, 1,2-dimethoxyethane, benzene, toluene, hexane, N-methylpyrrolidinone, or mixtures thereof at temperatures between −80 and 60° C., preferably between −50 and 40° C. The subsequent dehydration reaction to acquire the nortropene derivative may be performed using an acid, e.g. hydrochloric acid, hydrobromic acid, sulfuric acid, or phosphoric acid, a dehydrating reagent such as Burgess' reagent or Martin's sulfurane, or a sulfonyl chloride or anhydride in combination with a base such as methylsulfonyl chloride and triethylamine, thionyl chloride and pyridine, or triflic anhydride and pyridine. The reaction using an acid are preferably conducted in aqueous or alcoholic solutions that may contain co-solvents, e.g. tetrahydrofuran, N,N-dimethylformamide, dimethylsulfoxide, 1,4-dioxane, 1,2-dimethoxyethane, acetonitrile, or N-methylpyrrolidinone, at temperatures between 10 and 140° C. The conversion employing an dehydrating reagent are preferably conducted in an inert solvent such as dichloromethane, 1,2-dichloroethane, benzene, toluene, hexane, tetrahydrofuran, 1,4-dioxane, or 1,2-dimethoxyethane, at −30 to 140° C., preferably at −10 to 120° C. The C=C double bond is subsequently hydrogenated to give the derivatized nortropane. Competent catalyst for the hydrogenation using hydrogen may be e.g. platinum oxide, palladium on carbon, palladium hydroxide, Raney nickel, rhodium, ruthenium, and $ClRh(PPh_3)_3$. The hydrogenations are preferably carried out at temperatures between 0 and 180° C., preferably between 10 and 120° C., and at hydrogen pressures between 1 and 10 bar, preferably between 1 and 6 bar. Suited solvents may be water, alcohols, e.g. methanol or ethanol, acetic acid, N-methylpyrrolidinone, N,N-dimethylacetamide, N,N-dimethylformamide, ethyl acetate, acetonitrile, tetrahydrofuran, 1,4-dioxane, 1,2-dimethoxyethane, hexanes, dichloromethane, toluene, benzene, or mixtures thereof. Beneficial additives may be acids such as hydrochloric acid, sulfuric acid, methanesulfonic acid, trifluoroacetic acid, or acetic acid. The one-step conversion of the nortropanol derivative to the nortropane may also be feasible. This transformation may be carried out using hydrogen in the presence of a transition metal as described above, preferably in the presence of an acid. Alternatively, the reduction may be performed with a hydride source such as silane, e.g. triethylsilane, borohydride, e.g. sodium borohydride, triacetoxyborohydride, or cyanoborohydride, or alanate, e.g. lithium aluminum hydride, in the presence of a Lewis acid such as e.g. boron trifluoride, trimethylsilyl triflate, aluminum chloride, alkylaluminum dichloride, dialkylaluminum chloride, lanthanide triflates, scandium triflate, trifluoroacetic acid, or triflic acid. Preferred solvents for the latter process are dichloromethane, 1,2-dichloroethane, hexanes, 1,4-dioxane, 1,2-dimethoxyethane, toluene, benzene, chlorobenzene, and acetonitrile that are preferably used at temperatures between −30 and 180° C., more preferably between 0 and 140° C. The latter conditions are suited for electron-rich aromatic residues $R^1$.

The reduction from nortropanol or nortropene to nortropane may give mixtures of isomers (endo and exo) depending on the protective group used on the nitrogen and the reaction conditions. Mixture of isomers can be separated into the pure isomers by chromatography, distillation, or crystallization as described above. The entire sequence sketched in Scheme 3 is concluded by the removal of the protective group that may be accomplished as described hereinbefore.

such as 4-dimethylaminopyridine, pyridine, lithium chloride, 1,3-dimethyl-3,4,5,6-tetrahydro-2(1H)-pyrimidinone (DMPU), or hexamethylphosphoramide (HMPA) may be beneficial. Attachment of the residue $R^1$ may be accomplished by treatment of the enol triflate with an appropriate $R^1$ derivative in the presence of a transition metal catalyst. Appropriate $R^1$ derivatives are derived from e.g. lithium ($R^1Li$), magnesium, e.g. $R^1MgCl/Br$, zinc, e.g. $R^1ZnCl/Br/I$, boronic acids [$R^1B(OH)_2$], boronic esters, e.g. $R^1B(OMe)_2$ or $R^1B(OCMe_2CMe_2O)$, trifluoroborates, e.g. $R^1BF_3K$, silanes, e.g. $R^1SiF_3$, or stannanes, e.g. $R^1SnBu_3$ or $R^1SnMe_3$. Suited transition metal catalysts may be derived from palladium, copper, iron, and nickel which may be used as e.g. salts, complexes, or elemental modifications. Complexes can be formed in situ or prior to the addition of the transition metal to the reaction mixture. The ligands in the complexes of the transition metal may be e.g. phosphines, e.g. triphenylphosphine, tritolylphosphine, trifurylphosphine, substituted (2-phenyl-phenyl)-dicycloalkyl-phosphines, substituted (2-phenyl-phenyl)-di-tert-butyl-phosphines, tri-tert-butylphosphine, tricyclohexylphosphine, 1,1'-bis(diphenylphosphino)-ferrocene, phosphites, 1,3-disubstituted dihydroimidazolium carbenes, 1,3-disubstituted imidazolium carbenes, nitriles, e.g. acetonitrile or benzonitrile, and alkenes, e.g. benzylideneacetone or allyl. Elemental forms of the transition metals may be e.g. metal on charcoal or nanoparticles of the transition metal. Suitable salts may comprise e.g. halides, triflates, acetates, or trifluoroacetates. Depending on the $R^1$ precursor species used suited solvents vary. Suitable solvents may be e.g. tetrahydrofuran, 1,4-dioxane, 1,2-dimethoxyethane, hexane, toluene, benzene, N,N-dimethylformamide, N,N-dimethylacetamide, N-methylpyrrolidi-

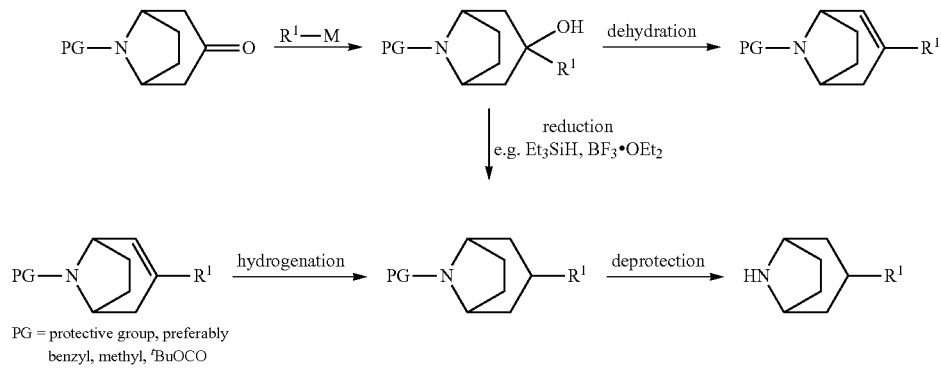

Scheme 3. Elaboration of Nortropanones I

PG = protective group, preferably benzyl, methyl, $^tBuOCO$

Scheme 4 depicts another synthetic route to the respectively derivatized nortropanes. Starting with the N-protected nortropanone the corresponding enol triflate may be accessed by treatment of the ketone with a base such as e.g. alkali metal hexamethyldisilylamide, alkali metal diisopropylamide, lithium 2,2,6,6-tetramethylpiperidide, ethyldiisopropylamine, triethylamine, 1,8-diazabicyclo[5.4.0]undec-7-ene, tert-butyllithium, or trityllithium and trapping the enolate with a trifluoromethylsulfonyl electrophile such as $F_3CSO_2OSO_2CF_3$, $F_3CSO_2Cl$, or $ArN(SO_2CF_3)_2$ (Ar=e.g. phenyl, pyridyl, or chloropyridyl). The reaction may be conducted in solvents such as e.g. tetrahydrofuran, 1,4-dioxane, 1,2-dimethoxyethane, ether, dichloromethane, benzene, toluene, hexanes, or mixtures thereof at temperatures between −80 and 80° C., preferably between −70 and 40° C. Additives none, acetone, acetonitrile, ethyl acetate, water, methanol, ethanol, propanol, isopropanol, ethylene glycol, and polyethylene glycol, though, not all of them can be employed with all $R^1$ precursors described above. The coupling reactions are preferably carried out between −80 and 180° C., more preferably at −20 to 120° C. Beneficial additives may be alkali metal salts, e.g. lithium chloride, tetraalkylammonium salts, e.g. tetrabutylammonium fluoride or hydroxide, silver salts, e.g. silver triflate, copper salts, e.g. copper iodide or copper thiophene-2-carboxylate, or bases, e.g. alkali metal hydroxides, potassium carbonate, alkali metal alcoxides, or alkali metal fluorides. The presented coupling approach to introduce $R^1$ is not restricted to enol triflates derived from nortropanones but may also be conducted using the corresponding alkenyl mesylates, toslylates, chlorides, bromides, or iodides. The concluding steps in Scheme 4 have been described above.

Scheme 4. Elaboration of Nortropanones II

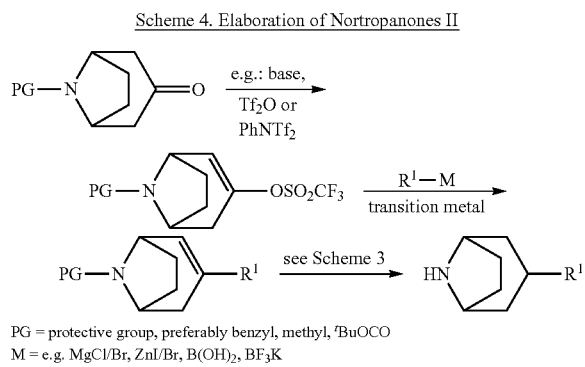

PG = protective group, preferably benzyl, methyl, ᵗBuOCO
M = e.g. MgCl/Br, ZnI/Br, B(OH)₂, BF₃K The synthetic routes presented may rely on the use of protecting groups. Suitable protecting groups for the respective functionalities and their removal have been described hereinbefore and may analogously be employed (see also: *Protecting Groups*, Philip J. Kocienski, 3rd edition, Georg Thieme Verlag, Stuttgart, 2004 and references quoted therein).

In the following a few feasible drivatizations of nortropanes of general formula I or precursors thereof, obtained as described above, bearing certain functional groups to assemble other compounds of general formula I or precursors thereof are vicariously summarized. This compilation is by no means meant to be complete but is only supposed to give some possibilities by way of example.

If in the process of manufacture according to the invention a compound of general formula I is obtained which contains an amino, alkylamino or imino group, this may be converted by acylation or sulfonylation into a corresponding acyl or sulfonyl compound of general formula I.

If a compound of general formula I is obtained which contains a hydroxy group, this may be converted by acylation or sulfonylation into a corresponding acyl or sulfonyl compound of general formula I.

If a compound of general formula I is obtained which contains a hydroxy group, this may be converted by alkylation into a corresponding ether of general formula I.

If a compound of general formula I is obtained which contains an amino, alkylamino, or imino group, this may be converted by alkylation or reductive alkylation into a corresponding alkyl compound of general formula I.

If a compound of general formula I is obtained which contains a nitro group, this may be converted by reduction into a corresponding amino compound.

If a compound of general formula I is obtained which contains an imino group, this may be converted by nitrosation and subsequent reduction into a corresponding N-amino-imino compound.

If a compound of general formula I is obtained which contains a $C_{1-4}$-alkyloxycarbonyl group, this may be converted by cleavage of the ester into the corresponding carboxy compound.

If a compound of general formula I is obtained which contains a carboxy group, this may be converted by esterification into a corresponding ester of general formula I.

If a compound of general formula I is obtained which contains a carboxy or ester group, this may be converted by reaction with an amine into a corresponding amide of general formula I.

If a compound of general formula I is obtained which contains an aromatic substructure, this may be derivatized with a chlorine, bromine, or iodine atom or a nitro, sulfonic acid, chlorosulfonyl, or acyl group to a corresponding compound of general formula I by an electrophilic substitution reaction.

If a compound of general formula I is obtained which contains an aromatic amino group, this may be transformed into a corresponding cyano, fluoro, chloro, bromo, iodo, hydroxy, mercapto, or azido compound of general formula I by diazotization and subsequent replacement of the diazo group with cyanide, fluoride, chloride, bromide, iodide, hydroxide, alkyl or hydrogen sulfide, or azide, respectively.

If a compound of general formula I is obtained which contains an aromatic amino group, this may be converted into a corresponding aryl derivatized aromatic compound of general formula I by diazotization of the amino group and subsequent replacement of the resulting diazo group with an appropriate aryl nucleophile mediated by a suited transition metal species.

If a compound of general formula I is obtained which contains an aromatic chloro, bromo, or iodo atom, or a trifluoromethylsulfonyloxy, mesyloxy, or tosyloxy group, this may be converted into a corresponding aryl, alkenyl, alkynyl, or alkyl derivatized compound of general formula I by replacement of the respective group by aryl, alkenyl, alkynyl, or alkyl using a transition metal species mediated process.

If a compound of general formula I is obtained which contains an aromatic chloro, bromo, or iodo atom, or a trifluoromethylsulfonyloxy, mesyloxy, or tosyloxy group, this may be replaced with hydrogen to give a corresponding aromatic compound of general formula I.

If a compound of general formula I is obtained which contains two heteroatoms at adjacent carbon atoms that are amino and hydroxy, amino, or mercapto, these heteroatoms may be linked via a carboxy carbon atom to form a cyclic amidine, imino ester, or imino thioester substructure that may be part of an aromatic ring.

If a compound of general formula I is obtained which contains a cyano group, this may be converted into an aminoalkyl derivatized compound of general formula I by reduction.

If a compound of general formula I is obtained which contains a cyano group, this may be converted into a N-hydroxycarbamimidoyl group by the treatment with hydroxylamine.

If a compound of general formula I is obtained which contains an N-hydroxycarbamimidoyl group, this may be converted to an oxadiazole derivatized compound of general formula I by the treatment with a carboxylic or related group.

If a compound of general formula I is obtained which contains an aminocarbonyl group, this may be converted by dehydration into a corresponding cyano compound of general formula I.

If a compound of general formula I is obtained which contains a keto or aldehydic group, this may be converted by reduction into a corresponding hydroxy compound of general formula I.

If a compound of general formula I is obtained which contains a carboxylic acid or aminocarbonyl group, this may be converted by a rearrangement reaction into a corresponding amino derivatized compound of general formula I.

If a compound of general formula I is obtained which contains a keto or aldehyde group, this may be converted into an alkenyl derivatized compound of general formula I.

If a compound of general formula I is obtained which contains an olefinic C═C double or a C≡C triple bond, this may be reduced to give the corresponding saturated compound of general formula I.

The subsequent esterification is optionally carried out in a solvent or mixture of solvents such as methylene chloride, N,N-dimethylformamide, benzene, toluene, chlorobenzene, tetrahydrofuran, benzene/tetrahydrofuran, or 1,4-dioxane or particularly advantageously in the corresponding alcohol optionally in the presence of an acid such as hydrochloric acid or in the presence of a dehydrating agent. Isobutyl chloroformate, thionyl chloride, trimethylchlorosilane, sulfuric acid, methanesulfonic acid, p-toluenesulfonic acid, phosphorus trichloride, phosphorus pentoxide, N,N'-carbonyldiimidazole, N,N'-dicyclohexylcarbodiimide, triphenylphosphine combined with carbon tetrachloride, or combinations thereof optionally in the presence of 4-dimethylaminopyridine and/or 1-hydroxybenzotriazole are among the routinely used reagents to accomplish this transformation. The reactions are conducted between 0 and 150° C., preferably between 0 and 80° C.

The subsequent ester formation may also be carried out by reacting a compound which contains a carboxy group with a corresponding alkyl halide in the presence of a base.

The subsequent acylation or sulfonylation is optionally carried out in a solvent or mixture of solvents such as methylene chloride, N,N-dimethylformamide, benzene, toluene, chlorobenzene, tetrahydrofuran, benzene/tetrahydrofuran, or 1,4-dioxane with a corresponding acyl or sulfonyl derivative, optionally in the presence of a tertiary organic base, an inorganic base, or a dehydrating agent. Routinely used agents are e.g. isobutyl chloroformate, thionyl chloride, trimethylchlorosilane, sulfuric acid, methanesulfonic acid, p-toluenesulfonic acid, phosphorus trichloride, phosphorus pentoxide, N,N'-dicyclohexylcarbodiimide, N,N'-carbonyldiimidazole, triphenylphosphine combined with carbon tetrachloride, or combinations thereof that may be employed in the presence of 4-dimethylaminopyridine and/or 1-hydroxybenzotriazole at temperatures between 0 and 150° C., preferably between 0 and 80° C.

The subsequent alkylation is optionally carried out in a solvent or mixture of solvents such as methylene chloride, N,N-dimethylformamide, benzene, toluene, chlorobenzene, tetrahydrofuran, benzene/tetrahydrofuran, or 1,4-dioxane with an alkylating agent such as a corresponding halide or sulfonic acid ester, e.g. methyl iodide, ethyl bromide, dimethyl sulfate, or benzyl chloride, optionally in the presence of a tertiary organic base or an inorganic base at temperatures between 0 and 150° C., preferably between 0 and 100° C.

The subsequent reductive alkylation is carried out with a corresponding carbonyl compound such as e.g. formaldehyde, acetaldehyde, propionaldehyde, acetone, or butyraldehyde in the presence of a complex metal hydride, such as e.g. sodium borohydride, lithium borohydride, sodium triacetoxyborohydride, or sodium cyanoborohydride, conveniently at a pH of 6-7 and at ambient temperature, or using hydrogen in the presence of a transition metal catalyst, e.g. palladium/charcoal, at a hydrogen pressure of 1 to 5 bar. Methylation may also be carried out in the presence of formic acid as reducing agent at elevated temperature, e.g. between 60 and 120° C.

The subsequent reduction of a nitro group is carried out, for example, with hydrogen and a catalyst such as palladium on carbon, platinum dioxide, or Raney nickel, or using other reducing agents such as iron or zinc in the presence of an acid such as acetic acid.

The subsequent nitrosation of an imino group followed by reduction to obtain an N-amino-imino compound is carried out, for example, with an alkyl nitrite such as isoamyl nitrite to form the N-nitroso-imino compound that is then reduced to the N-amino-imino compound using, for example, zinc in the presence of an acid such as acetic acid.

The subsequent cleaving of a $C_{1-4}$-alkyloxycarbonyl group to obtain the carboxy group is carried out, for example, by hydrolysis with an acid such as hydrochloric acid or sulfuric acid or an alkali metal hydroxide such as lithium hydroxide, sodium hydroxide, or potassium hydroxide.

The subsequent amide formation is carried out by reacting a corresponding reactive carboxylic acid derivative with a corresponding amine optionally in a solvent or mixture of solvents such as methylene chloride, N,N-dimethylformamide, benzene, toluene, chlorobenzene, tetrahydrofuran, benzene/tetrahydrofuran, or 1,4-dioxane, while the amine used may also serve as solvent, optionally in the presence of a tertiary organic base, an inorganic base, 4-dimethylaminopyridine and/or 1-hydroxy-benzotriazole, at temperatures between 0 and 150° C., preferably between 0 and 80° C. Using the carboxylic acid may lead to the desired amide by in situ activation of the carboxy function with e.g. isobutyl chloroformate, thionyl chloride, oxalyl chloride, trimethylchlorosilane, phosphorus trichloride, phosphorus pentoxide, N,N'-carbonyldiimidazole, triphenylphosphine/carbon tetrachloride, 2-(1H-benzotriazol-1-yl)-1,1,3,3-tetramethyluronium tetrafluoroborate, N,N'-dicyclohexylcarbodiimide, or combinations thereof.

The subsequent introduction of a chlorine, bromine, or iodine atom into an aromatic substructure may be carried out by reacting the aromatic compound with an appropriate electrophile of the respective halogen atom. Suited chlorine and bromine electrophiles may be e.g. N-halosuccinimide, HOCl, HOBr, tert-BuOCl, tert-BuOBr, chlorine, bromine, dibromoisocyanuric acid, pyridinium dichlorobromate, pyridinium tribromide, or sulfuryl chloride, that may be used alone or in combination with an acid, e.g. hydrochloric acid, hydrobromic acid, tetrafluoroboric acid, triflic acid, sulfuric acid, or acetic acid, or a Lewis acid, e.g. iron(III) halide, boron trifluoride hydrate, boron trifluoride etherate, or aluminum halide. Further useful combinations may be LiBr and ceric ammonium nitrate, KCl or KBr with Oxone®, or KBr and sodium perborate. Suited iodine electrophiles may be generated from iodine and an oxidizing agent such as nitric acid, sulfur trioxide, manganese dioxide, $HIO_3$, hydrogen peroxide, sodium periodate, peroxydisulfates, and Oxone®. Further suited iodine electrophiles may be e.g. iodine chloride, dichloroiodates, and N-iodosuccinimide. These iodine electrophiles may be used without an additive or in the presence of an acid such as e.g. acetic acid, trifluoroacetic acid, or sulfuric acid, or a Lewis acid such as boron trifluoride hydrate, or copper salts. If a nitro group is to be introduced appropriate nitro electrophiles may be generated from, for example, nitric acid, acetyl nitrate, ceric ammonium nitrate, sodium nitrate, $N_2O_5$, alkyl nitrate, and nitronium tetrafluoroborate. Some of these reagents may be used without an additive, though, several of them are better used in combination with an acid, e.g. sulfuric acid or triflic acid, acetic anhydride, trifluoroacetic anhydride, Lewis acid, e.g. ytterbium triflate or iron acetate, $P_2O_5$, or a base. The $SO_3H$ group may be introduced by reacting the aromatic compound with, for example, concentrated sulfuric acid, $SO_3$, $ClSO_3H$, or $ClSO_2NMe_2$ combined with indium triflate. Reacting the aromatic compound with $ClSO_3H$ gives the corresponding chlorosulfonylated derivative that may be hydrolyzed to the sulfonic acid. Acylating the aromatic part is conducted using an acyl electrophile that may be generated from the respective acyl halide, e.g. chloride, or acyl anhydride and a Lewis acid such as e.g. aluminum halide, diethylaluminum halide, indium halide, iron(III) halide, tin(IV) halide, boron trifluoride, titanium(IV) halide, or a Brønsted acid, e.g. sulfuric acid or triflic acid. The formyl group is best introduced using the so-called Vilsmeier or Vilsmeier-Haack conditions: dialkylformamide combined with phosgene, thionyl chloride, $POCl_3$, or oxalyl chloride. Preferred solvents for the electrophilic substitutions described may differ depending on the electrophile employed; in the following some more generally applicable are mentioned: methylene chloride, 1,2-dichloroethane, chlorobenzene, dichlorobenzene, ether, fluorinated hydrocarbons, hexanes, quinoline, and acetonitrile. The temperatures preferably applied range from 0 to 180° C.

The subsequent replacement of an aromatic amino group is initiated by diazotization of the amino group using a nitrous acid or nitrosonium source or equivalent such as a nitrite salt combined with an acid, e.g. sodium nitrite and hydrochloric acid, nitrosonium tetrafluoroborate, or an alkylnitrite, e.g. tert-butyl nitrite or iso-amyl nitrite. The diazotization is optionally carried out in methylene chloride, 1,2-dichloroethane, N,N-dimethylformamide, N-methylpyrrolidinone, benzene, toluene, chlorobenzene, tetrahydrofuran, water, ethyl acetate, alcohol, ether, 1,2-dimethoxyethane, 1,4-dioxane, or mixtures thereof at temperatures between −10 and 100° C. (diazotization of amino groups is detailed in, for example, *Angew. Chem. Int. Ed.* 1976, 15, 251). The subsequent displacement of the diazo group with a cyano group, chlorine, or bromine atom using copper cyanide, chloride, or bromide, respectively, is known as the Sandmeyer reaction (see e.g. March's Advanced Organic Chemistry, Michael B. Smith and Jerry March, John Wiley & Sons Inc., 6. Ed., New Jersey, 2007 and references quoted therein); the reaction is optionally conducted between −10 and 120° C. in one of the solvents or mixtures mentioned above. The replacement of the diazo group with a fluorine atom may be achieved with a tetrafluoroborate salt or tetrafluoroboric acid and heating to 20 to 160° C.; the reaction is known as the Schiemann reaction. Iodine may be introduced by treatment of the diazo compound with an iodide salt, e.g. sodium iodide, preferably using water or an aqueous solvent mixture at temperatures between 0 and 120° C. The diazo group is replaced with hydroxy using water or an aqueous solvent mixture at temperatures between 0 and 180° C. The reaction usually works without further additives but the addition of copper oxide or strong acid may be advantageous. Mercapto or alkylmercapto may be introduced via their corresponding disulfide salts or dialkyldisulfides at temperatures between 0 and 120° C.; depending on the sulfur species used an inert solvent or aqueous solvent system may be preferred (see e.g. *Synth. Commun.* 2001, 31, 1857 and references quoted therein).

The subsequent replacement of an aromatic amino group by an aryl group may be carried out via the corresponding diazo compound obtainable as described above. The reaction with an aryl nucleophile, preferably an aryl boronic acid, boronic ester, trifluoroborate, zinc halide, or stannane, is conducted in the presence of a transition metal species derived from palladium, nickel, rhodium, copper, or iron, preferably palladium. The active catalyst may be a complex of the transition metal with ligands such as e.g. phosphines, phosphites, imdiazole carbenes, imidazolidine carbenes, dibenzylideneacetone, allyl, or nitriles, an elemental form of the transition metal such as palladium on carbon or nanoparticles, or salts such as chloride, bromide, acetate, or trifluoroacetate. In these reactions the diazo compound is preferably employed as its tetrafluoroborate salt optionally in water, N-methylpyrrolidinone, N,N-dimethylformamide, methylene chloride, benzene, toluene, tetrahydrofuran, ethyl acetate, alcohol, ether, 1,2-dimethoxyethane, 1,4-dioxane, or mixtures thereof at temperatures between 10 and 180° C., preferably between 20 and 140° C.

The subsequent replacement of an aromatic chloro, bromo, or iodo atom or an aromatic trifluoromethylsulfonyloxy, mesyloxy, or tosyloxy group with an aryl, alkenyl, alkynyl, or alkyl residue is preferably mediated by a transition metal species derived from palladium, nickel, rhodium, copper, or iron. The active catalyst may be a complex of the transition metal with ligands such as e.g. phosphines [e.g. tri-tert-butylphosphine, tricyclohexylphosphine, substituted (2-phenyl-phenyl)-dicyclohexyl-phosphines, substituted (2-phenyl-phenyl)-di-tertbutylphosphines, 1,1'-bis(diphenylphosphino)ferrocene, trifurylphosphine, tritolylphosphine, triphenylphosphine, phosphites, 1,3-disubstituted imdiazole carbenes, 1,3-disubstituted imidazolidine carbenes, dibenzylideneacetone, allyl, or nitriles, an elemental form of the transition metal such as palladium on carbon or nanoparticles of iron or palladium, or a salt such as e.g. fluoride, chloride, bromide, acetate, triflate, or trifluoroacetate. The replacement reaction is preferably conducted with a trifluoroborate, boronic acid, or boronic ester (Suzuki or Suzuki-type reaction), zinc halide (Negishi or Negishi-type reaction), stannane (Stille or Stille-type reaction), silane (Hiyama or Hiyama-type reaction), magnesium halide (Kumada or Kumada-type reaction) of the aryl, alkenyl, or alkyl residue to be introduced. The terminal alkyne is preferably used as it is or as its zinc acetylide derivative. Depending on the nature of the electrophilic and nucleophilic reaction partners additives such as halide salts, e.g. lithium chloride, potassium fluoride, tetrabutylammonium fluoride, hydroxide sources such as potassium hydroxide or potassium carbonate, silver salts such as silver oxide or triflate, copper salts such as copper chloride or copper thiophene-2-carboxylate may be advantageous or even essential. Copper iodide is a preferred additive in the coupling with terminal alkynes (Sonogashira reaction). The coupling reactions are optionally conducted in benzene, toluene, methylene chloride, ether, tetrahydrofuran, 1,2-dimethoxyethane, 1,4-dioxane, ethyl acetate, N,N-dimethylformamide, N-methylpyrrolidinone, dimethylsulfoxide, alcohol, water, or mixtures thereof, though, depending on the nucleophile some of them are less or not suited at all. Preferred temperatures are in the range from −10 to 180° C.

The subsequent replacement of an aromatic chlorine, bromine, or iodine atom or an aromatic trifluoromethylsulfonyloxy, mesyloxy, or tosyloxy group with a hydrogen atom is preferably mediated by a transition metal species derived from palladium, nickel, platinum, or rhodium. The active catalyst may be a complex of the transition metal with ligands, an elemental form, or a salt of the transition metal as mentioned above. Raney nickel or palladium on carbon are among the preferred catalyst species. Suited hydrogen sources may be hydrogen, preferably at pressures of 1 to 5 bar, silanes, e.g. trialkoxysilane or polymethylhydrosiloxane, boranes, hydrides, e.g. alkali metal borohydride, formic acid, or formates, e.g. ammonium formate. The reactions are preferably carried out in methylene chloride, N,N-dimethylformamide, N,N-dimethylacetamide, N-methylpyrrolidinone, benzene, toluene, tetrahydrofuran, water, ethyl acetate, alcohol, ether, 1,2-dimethoxyethane, 1,4-dioxane, or mixtures thereof at −10 to 180° C., more preferably at 20 to 140° C.

The subsequent cyclization starting from a compound bearing two heteroatoms at adjacent carbon atoms is optionally conducted with a carboxy equivalent such as nitrile, carboxylic chloride or fluoride, carboxylic acid, ketene, carboxylic ester, or carboxylic thioester. The overall transformation consists of two reaction steps: attachment of the carboxy equivalent to one of the two heteroatoms followed by cyclization with the other heteroatom. The first step is an amide formation with the amino functionality that may be carried out as described hereinbefore. The ensuing reaction step, cyclization with the second heteroatom, may be accomplished by heating in the presence of an acid, e.g. acetic acid, trifluoroacetic acid, sulfuric acid, or hydrochloric acid, or a base, e.g. sodium hydroxide, sodium ethoxide, or sodium tert-butoxide. The use of dehydrating reagents such as anhydrides, e.g. acetic anhydride, orthoesters, e.g. trimethyl orthoformate, thionyl chloride, phosgene, diphosgene, triphosgene, phosphorous oxychloride, phosphorous pentachloride, dialkylcarbodiimides, combinations with phosphines, e.g. triphenylphosphine or trialkylphosphine with dialkyl azodicarboxylates, bromine, iodine, or 1,2-dihaloethanes, e.g. 1,2-dibromotetrafluoroethane, may be advantageous. The reactions are preferably carried out in inert solvents or mixtures such as methylene chloride, 1,2-dichloroethane, benzene, toluene, tetrahydrofuran, ether, or combinations thereof, though, cyclization in the presence of an acid or a base may also be conducted in water or an alcohol, e.g. methanol, ethanol, iso-propanol, or tert-butanol, or combinations with these solvents. The reactions are carried out at temperatures between 0 and 200° C., preferably between 20 and 140° C.

The subsequent reduction of a cyano group to obtain an aminomethyl group is optionally conducted with hydrogen in the presence of a transition metal species or with a hydride. Suited transition metals may be derived from palladium, nickel, platinum, rhodium, or ruthenium such as, for example, palladium on charcoal, palladium hydroxide, platinum oxide, or Raney nickel, that may be used in solvents such as ethyl acetate, alcohols, e.g. methanol or ethanol, dichloromethane, tetrahydrofuran, ether, benzene, toluene, N,N-dimethylformamide, or N-methylpyrrolidinone at hydrogen pressures between 1 and 10 bar, preferably between 1 and 5 bar, and at temperatures between 0 and 180° C., preferably between 20 and 120° C. Additives such as acids, e.g. hydrochloric acid, methanesulfonic acid, sulfuric acid, or acetic acid, may be beneficial for the hydrogenation. Appropriate hydride sources may be selected from e.g. borohydrides, e.g. sodium borohydride, potassium tri-sec-butylborohydride, borane, or lithium triethylborohydride, or alanates, e.g. lithium aluminum hydride or diisobutylaluminum hydride. Some of these reagents are best used in combination with nickel chloride or cobalt chloride as sodium borohydride. These reagents may be used in e.g. tetrahydrofuran, ether, 1,4-dioxane, 1,2-dimethoxyethane, dichloromethane, 1,2-dichloroethane, benzene, or toluene; some are also compatible with alcoholic solutions. Preferred reaction temperatures range from −80 to 160° C., more preferred from −40 to 80° C.

The subsequent formation of a N-hydroxycarbamimidoyl group from a cyano group may be carried out by the treatment of the cyano compound with hydroxylamine. The reaction is preferably conducted in aqueous or alcoholic solvents at temperatures between 0 and 140° C.

The subsequent formation of an oxadiazole from an N-hydroxycarbamimidoyl is optionally conducted with a carboxy equivalent such as nitrile, carboxylic chloride or fluoride, carboxylic acid, ketene, carboxylic ester, or carboxylic thioester. The transformation is related to the formation of a ring starting from two adjacent heteroatoms described above and may be carried out analogously.

The subsequent formation of a cyano group from an aminocarbonyl group is optionally conducted by using a dehydrating reagent such as e.g. anhydride, e.g. acetic anhydride, trifluoroacetic anhydride, or triflic anhydride, phosgene, thionyl chloride, oxalyl chloride, $POCl_3$, $PCl_5$, $P_4O_{10}$, triphenylphosphite, or triphenyl- or trialkylphosphine combined with tetrachloromethane, 1,2-dibromotetrafluoroethane, or bromine. The reactions are preferably carried out in dichloromethane, 1,2-dichloroethane, hexanes, ether, 1,4-dioxane, benzene, toluene, acetonitrile, mixtures thereof, or without a solvent at temperatures between 0 and 140° C. Additives such as amines, e.g. pyridine or triethylamine, or N,N-dimethylformamide may be beneficial.

The subsequent reduction of a keto or an aldehydic group to obtain a secondary or primary alcohol may be carried out with a complex metal hydride such as sodium borohydride, lithium borohydride, lithium triethylborohydride, diisobutylaluminum hydride, or lithium aluminum hydride. The reductions may be conducted in e.g. dichloromethane, 1,2-dichloroethane, hexanes, ether, 1,4-dioxane, tetrahydrofuran, N,N-dimethylformamide, N-methylpyrrolidinone, benzene, toluene, alcohols, e.g. methanol, water, or mixtures thereof, though, not all reducing agents are compatible with all of these solvents. Preferred temperatures range from −80 to 140° C. depending on the reducing power of the reagent. Alternatively, hydrogen in the presence of a transition metal catalyst may be used for the reduction.

The subsequent conversion of a carboxy group into an amino group by rearrangement may be accomplished by heating an acyl azide resulting in the formation of an isocyanate (Curtius rearrangement). The isocyanate may be hydrolyzed to produce the free amine or converted into a urea or carbamate derivative by treatment with an amine or an alcohol, respectively. The acyl azide may be obtained by treating an appropriate acyl electrophile, e.g. acyl chloride, carboxylic anhydride, or carboxylic ester, with an azide source, such as e.g. sodium azide or trimethylsilyl azide, in a solvent such as 1,4-dioxane, 1,2-dimethoxyethane, acetonitrile, tetrahydrofuran, dichloromethane, 1,2-dichloroethane, N-methylpyrrolidinone, N,N-dimethylformamide, toluene, benzene, hexanes, or mixtures thereof; water or alcohols may be usable in certain cases as well. The reactions are routinely carried out between −10 and 120° C. Alternatively, the acyl electrophile may be generated from the acid in situ and then converted into the acyl azide: diphenylphosphoryl azide in the presence of a base, e.g. triethylamine or ethyldiisopropylamine, in a solvent such as acetonitrile, benzene, toluene, or an alcohol, at elevated temperature has proven to be an effective reagent for this direct conversion. The direct conversion may also be achieved with hydrazoic acid and an acid catalyst such as sulfuric acid in e.g. chloroform at elevated temperatures (Schmidt reaction).

Another method to accomplish this overall transformation is the Lossen rearrangement: starting from an acyl elctrophile, such as acyl chloride, the corresponding suited hydroxamic acid derivative is formed that in turn rearranges to give the isocyanate and amine, respectively, by the treatment with a base, e.g. sodium hydroxide (see e.g. *J. Org. Chem.* 1997, 62, 3858 and *Synthesis* 1990, 1143 and references quoted therein).

An unsubstituted carboxylic amide may be converted into an amine by the so-called Hoffmann rearrangement. Among the suited reagents for this transformation are NaOBr, bromine combined with sodium methoxide, N-bromosuccinimide and sodium methoxide, $PhI(OCOCF_3)_2$, and $PhI(OH)$OTs.

The subsequent conversion of an aldehydic or keto functionality into an olefin may be accomplished by, for example, the so-called Wittig reaction and modifications thereof, Peterson olefination, Julia reaction and modifications thereof. These reactions have large precedence in organic syntheses and are detailed in e.g. March's Advanced Organic Chemistry, Michael B. Smith and Jerry March, John Wiley & Sons Inc., 6. Ed., New Jersey, 2007 and references quoted therein.

The subsequent reduction of a C=C double or C≡C triple bond is preferably conducted with hydrogen in the presence of a transition metal species derived from palladium, nickel, platinum, ruthenium, or rhodium, preferably, Raney nickel, palladium on charcoal, platinum oxide, and RhCl(PPh)$_3$. The reactions are preferably carried out in methylene chloride, N,N-dimethylformamide, N,N-dimethylacetamide, N-methylpyrrolidinone, benzene, toluene, tetrahydrofuran, water, ethyl acetate, alcohol, ether, 1,2-dimethoxyethane, 1,4-dioxane, or mixtures thereof at 0 to 180° C., more preferably at 20 to 140° C., and hydrogen pressures of 1 to 10 bar, preferably 1 to 5 bar.

In the reactions described hereinbefore, any reactive group present such as hydroxy, carbonyl, carboxy, amino, alkylamino, or imino may be protected during the reaction by conventional protecting groups which are cleaved again after the reaction.

For example, a protecting group for a hydroxy group may be a trimethylsilyl, tertbutyldimethylsilyl, triisopropylsilyl, acetyl, pivaloyl, benzoyl, methyl, tert-butyl, allyl, trityl, benzyl, 4-methoxybenzyl, tetrahydropyranyl, methoxymethyl, ethoxymethyl, or 2-trimethylsilylethoxymethyl group, protecting groups for a carboxy group may be trimethylsilyl, methyl, ethyl, tert-butyl, allyl, benzyl, or tetrahydropyranyl, protecting groups for a ketone or aldehyde may be a ketal or acetal, respectively, e.g. derived from methanol, glycol, propane-1,3-diol or propane-1,3-dithiol,
protecting groups for an amino, alkylamino, or imino group may be methyl, formyl, acetyl, trifluoroacetyl, ethoxycarbonyl, tert-butoxycarbonyl, benzyloxycarbonyl, benzyl, 4-methoxybenzyl, or 2,4-dimethoxybenzyl and for the amino group additionally phthalyl and tetrachlorophthalyl, and protecting groups for a terminal alkyne may be trimethylsilyl, triisopropylsilyl, tertbutyldimethylsilyl, or 2-hydroxy-prop-2-yl.

Any acyl protecting group may be cleaved, for example, hydrolytically in an aqueous solvent, e.g. in water, isopropanol/water, acetic acid/water, tetrahydrofuran/water, or 1,4-dioxane/water, in the presence of an acid such as trifluoroacetic acid, hydrochloric acid, or sulfuric acid or in the presence of an alkali metal base such as lithium hydroxide, sodium hydroxide, or potassium hydroxide or aprotically, e.g. in the presence of iodotrimethylsilane, at temperatures between 0 and 120° C., preferably between 10 and 100° C. A trifluoroacetyl group is preferably cleaved by treating with an acid such as hydrochloric acid, optionally in a solvent such as acetic acid, at temperatures between 50 and 120° C. or by treating with aqueous sodium hydroxide solution, optionally in an additional solvent such as tetrahydrofuran or methanol, at temperatures between 0 and 80° C.

Any acetal or ketal protecting group used may be cleaved, for example, hydrolytically in an aqueous solvent, e.g. in water, isopropanol/water, acetic acid/water, tetrahydrofuran/water, or 1,4-dioxane/water, in the presence of an acid such as acetic acid, trifluoroacetic acid, hydrochloric acid, or sulfuric acid or aprotically, e.g. in the presence of iodotrimethylsilane, at temperatures between 0 and 120° C., preferably between 10 and 100° C.

A trimethylsilyl group is cleaved, for example, in water, an aqueous solvent mixture or an alcohol, such as methanol or ethanol, in the presence of a base such as lithium hydroxide, sodium hydroxide, potassium carbonate, or sodium methoxide. Acids such as e.g. hydrochloric acid, trifluoroacetic acid, or acetic acid may also be suitable. The cleavage usually takes place at comparatively low temperatures, e.g. between −60 and 60° C. Silyl groups other than trimethylsilyl are preferentially cleaved in the presence of an acid, e.g. trifluoroacetic acid, hydrochloric acid, or sulfuric acid, at temperatures between 0 and 100° C. A particularly suited cleaving method for silyl groups is based on the use of fluoride salts, e.g. tetrabutylammonium fluoride, hydrogen fluoride, or potassium fluoride, in organic solvents, such as for example diethyl ether, tetrahydrofuran, 1,4-dioxane, 1,2-dimethoxyethane, toluene, benzene, 1,2-dichloroethane, or dichloromethane at temperatures between −20 and 100° C.

A benzyl, methoxybenzyl, or benzyloxycarbonyl group is advantageously cleaved hydrogenolytically, e.g. with hydrogen in the presence of a catalyst such as palladium on carbon, palladium hydroxide, or platinum oxide, in a solvent such as methanol, ethanol, ethyl acetate, or acetic acid, optionally in the presence of an acid, such as hydrochloric acid, at temperatures between 0 and 100° C., preferably between 20 and 60° C., and at hydrogen pressures of 1 to 7 bar, preferably 3 to 5 bar. Trimethylsilyl iodide, boron trichloride, or boron trifluoride in the presence of a scavenger such as anisol, thioanisol, or pentamethylbenzene may also be used with benzylether derivatives. An electron-rich benzyl residue, such as methoxybenzyl, may also be cleaved oxidatively with e.g. 2,3-dichloro-5,6-dicyano-1,4-benzoquinone (DDQ) or ceric ammonium nitrate (CAN) preferably in an alcoholic or aqueous solvent at temperatures between 10 and 120° C. A 2,4-dimethoxybenzyl group is preferably cleaved in trifluoroacetic acid in the presence of a scavenger such as anisole.

A tert-butyl or tert-butyloxycarbonyl group is preferably cleaved by treating with an acid such as trifluoroacetic acid, sulfuric acid, or hydrochloric acid or by treating with iodotrimethylsilane optionally using a solvent such as methylene chloride, 1,4-dioxane, methanol, isopropanol, water, or diethylether.

A methyl group at an tertiary amine may be cleaved by the treatment with 1-chloroethyl chloroformate. Hydrobromic acid and borontribromide are particularly suited for the cleavage of methylethers.

The compounds of general formula I may be resolved into their enantiomers and/or diastereomers, as mentioned before. Thus, for example, cis/trans mixtures may be resolved into their cis and trans isomers, and racemic compounds may be separated into their enantiomers.

The cis/trans mixtures may be resolved, for example, by chromatography into the cis and trans isomers thereof. The compounds of general formula I which occur as racemates may be separated by methods known per se (cf. Allinger N. L. and Eliel E. L. in "Topics in Stereochemistry", Vol. 6, Wiley Interscience, 1971) into their optical antipodes and diastereomeric mixtures of compounds of general formula I may be resolved into their diastereomers by taking advantage of their different physico-chemical properties using methods known per se, e.g. chromatography and/or fractional crystallization; if the compounds obtained thereafter are racemates, they may be resolved into the enantiomers as mentioned above.

The racemates are preferably resolved by column chromatography on chiral phases or by crystallisation from an optically active solvent or by reacting with an optically active substance which forms salts or derivatives, such as e.g. esters or amides, with the racemic compound. Salts may be formed with enantiopure acids for basic compounds and with enantiopure bases for acidic compounds. Diastereomeric derivatives are formed with enantiopure auxiliary compounds such as e.g. acids, their activated derivatives, or alcohols. Separation of the diastereomeric mixture of salts or derivatives thus obtained may be achieved by taking advantage of their different physico-chemical properties, e.g. differences in solubility; the free antipodes may be released from the pure diastereomeric salts or derivatives by the action of suitable agents. Optically active acids in common use for such a purpose are e.g. the D- and L-forms of tartaric acid, dibenzoyltartaric acid, di-o-tolyltartaric acid, malic acid, mandelic acid, camphorsulfonic acid, glutamic acid, aspartic acid, or quinic acid. Optically active alcohols applicable as auxiliary residues may be, for example, (+) or (−)-menthol and optically active acyl groups in amides may be, for example, (+)- or (−)-menthyloxycarbonyl.

As mentioned above, the compounds of formula I may be converted into salts, particularly for pharmaceutical use into the physiologically acceptable salts, with inorganic or organic acids, provided that compound I bears a basic residue. Acids which may be used for this purpose include for example hydrochloric acid, hydrobromic acid, sulfuric acid, methanesulfonic acid, phosphoric acid, fumaric acid, succinic acid, lactic acid, citric acid, tartaric acid, or maleic acid.

If the compounds of formula I contain an acidic residue like, for example, a carboxy group, they may be converted into the salts thereof with inorganic or organic bases, particularly for pharmaceutical use into the physiologically acceptable salts thereof. Suitable bases for this purpose include, for example, sodium hydroxide, potassium hydroxide, calcium hydroxide, calcium isopropoxide, magnesium hydroxide, magnesium ethoxide, ammonium hydroxide, cyclohexylamine, ethanolamine, diethanolamine, triethanolamine, N-methyl-D-glucamine, Llysine, L-arginine, and piperazine.

The compounds according to the invention are advantageously also obtainable using the methods described in the examples that follow, which may also be combined for this purpose with methods known to the skilled man from the literature.

As already mentioned, the compounds of general formula I according to the invention and the physiologically acceptable salts thereof have valuable pharmacological properties, particularly an inhibitory effect on the enzyme 11β-hydroxysteroid dehydrogenase (HSD) 1.

The biological properties of the new compounds may be investigated as follows:

In vitro inhibition of 11β-HSD1 by test compounds is determined with HTRF (Homogeneous Time-Resolved Fluorescence) technology (cisbio international, France) detecting cortisol generated from cortisterone by human liver microsomes. Briefly, compounds are incubated for 1 hour at 37° C. in Tris buffer (20 mM tris, 5 mM EDTA, pH 6.0) containing NADPH (200 μM) and cortisone (80 nM). Cortisol generated in the reaction is then detected with a competitive immunoassay, involving two HTRF conjugates: cortisol linked to XL665 and anti-cortisol antibody labeled with Europium cryptate. The incubation period for detection reaction is typically 2 hours. The amount of cortisol is determined by reading the time-resolved fluorescence of the wells (Ex 320/75 nm; Em 615/8.5 nm and 665/7.5 nm). The ratio of the two emission signals is then calculated (Em665*10000/Em615). Each assay contains incubations with vehicle controls instead of compound as controls for non-inhibited cortisol generation (100% CTL; 'high values') and incubations with carbenoxolone as controls for fully inhibited enzyme and cortisol background (0% CTL; 'low values'). Each assay also contains a calibration curve with cortisol to transform the fluorescent data into cortisol concentrations. Percent inhibition (% CTL) of each compound is determined relative to the carbenoxolone signal and $IC_{50}$ curves are generated.

The compounds of general formula I according to the invention for example have $IC_{50}$ values below 10000 nM, particularly below 1000 nM, most preferably below 200 nM.

The % CTL values of some example compounds at a concentration of 1 μM are provided in the following Table 2 wherein 100% indicates no inhibition and a value of zero or below zero indicates complete inhibition. The measurement of % CTL is described hereinbefore.

TABLE 2

Inhibitory activity on 11-β HSD 1 of the compounds listed in Table 3

| Example No. | 11β-HSD 1 inhibition % CTL at 1 μM |
| --- | --- |
| 1 | −49 |
| 2 | −3 |
| 3 | −29 |
| 4 | 46 |
| 5 | −46 |
| 6 | 65 |
| 7 | −57 |
| 8 | −59 |
| 9 | −49 |
| 11 | 4 |
| 12 | −27 |
| 13 | −25 |
| 14 | −30 |
| 15 | 20 |
| 16 | −23 |
| 17 | −11 |
| 18 | 62 |
| 19 | 34 |
| 20 | −17 |
| 21 | −20 |
| 22 | −18 |

In view of their ability to inhibit the enzyme 11β-hydroxysteroid dehydrogenase (HSD) 1, the compounds of general formula I according to the invention and the corresponding pharmaceutically acceptable salts thereof are theoretically suitable for the treatment and/or preventative treatment of all those conditions or diseases which may be affected by the inhibition of the 11β-hydroxysteroid dehydrogenase (HSD) 1 activity. Therefore, compounds according to the invention are particularly suitable for the prevention or treatment of diseases, particularly metabolic disorders, or conditions such as type 1 and type 2 diabetes mellitus, complications of diabetes (such as e.g. retinopathy, nephropathy or neuropathies, diabetic foot, ulcers, macroangiopathies, slow or poor wound healing), metabolic acidosis or ketosis, reactive hypoglycaemia, hyperinsulinaemia, glucose metabolic disorder, insulin resistance, metabolic syndrome, dyslipidaemias of different origins, atherosclerosis and related diseases, obesity, high blood pressure, chronic heart failure, edema and hyperuricaemia. These substances may also be suitable for preventing beta-cell degeneration such as e.g. apoptosis or necrosis of pancreatic beta-cells. The substances may also be suitable for improving or restoring the functionality of pancreatic cells, and also of increasing the number and size of pancreatic beta-cells. The compounds according to the invention may also be used as diuretics or antihypertensives and are suitable for the prevention and treatment of acute renal failure.

Additionally, inhibition of 11β-hydroxysteroid dehydrogenase (HSD) 1 has been shown to lower intraocular pressure in subjects with ocular hypertension, therefore the compounds could be used to treat glaucoma.

In view of the role of 11β-hydroxysteroid dehydrogenase (HSD) 1 in modulating cortisol levels for interaction with the glucocorticoid receptor, and the known role of excess glucocorticoids in bone loss, the compounds may have beneficial effects against osteoporosis.

Stress and/or glucocorticoids have been shown to influence cognitive function, and excess cortisol has been associated with brain neuronal loss or dysfunction. Treatment with an 11β-hydroxysteroid dehydrogenase (HSD) 1 inhibitor may result in amelioration or prevention of cognitive impairment. Such compounds may also be useful in treating anxiety or depression.

The dynamic interaction between the immune system and the HPA (hypothalamopituitaryadrenal) axis is known, and glucocorticoids help balance between cell-mediated responses and humoral responses. The immune reaction is typically biased towards a humoral response in certain disease states, such as tuberculosis, leprosy, and psoriasis. More appropriate would be a cell-based response. An 11β-hydroxysteroid dehydrogenase (HSD) 1 inhibitor would bolster a temporal immune response in association with immunization to ensure that a cell based response would be obtained, and as such could be useful in immunomodulation.

In particular, the compounds according to the invention, including the physiologically acceptable salts thereof, are suitable for the prevention or treatment of diabetes, particularly type 1 and type 2 diabetes mellitus, and/or diabetic complications.

The dosage required to achieve the corresponding activity for treatment or prevention usually depends on the compound which is to be administered, the patient, the nature and gravity of the illness or condition and the method and frequency of administration and is for the patient's doctor to decide. Expediently, the dosage may be from 1 to 100 mg, preferably 1 to 30 mg, by intravenous route, and 1 to 1000 mg, preferably 1 to 100 mg, by oral route, in each case administered 1 to 4 times a day. For this purpose, the compounds of formula I prepared according to the invention may be formulated, optionally together with other active substances, together with one or more inert conventional carriers and/or diluents, e.g. with corn starch, lactose, glucose, microcrystalline cellulose, magnesium stearate, citric acid, tartaric acid, water, polyvinylpyrrolidone, water/ethanol, water/glycerol, water/sorbitol, water/polyethylene glycol, propylene glycol, cetylstearyl alcohol, carboxymethylcellulose or fatty substances such as hard fat or suitable mixtures thereof, to produce conventional galenic preparations such as plain or coated tablets, capsules, powders, suspensions or suppositories.

The compounds according to the invention may also be used in conjunction with other active substances, particularly for the treatment and/or prevention of the diseases and conditions mentioned above. Other active substances which are suitable for such combinations include, for example, those which potentiate the therapeutic effect of an 11β-hydroxysteroid dehydrogenase (HSD) 1 antagonist according to the invention with respect to one of the indications mentioned and/or which allow the dosage of an 11β-hydroxysteroid dehydrogenase (HSD) 1 antagonist according to the invention to be reduced. Therapeutic agents which are suitable for such a combination include, for example, antidiabetic agents such as metformin, sulfonylureas (e.g. glibenclamide, tolbutamide, glimepiride), nateglinide, repaglinide, thiazolidinediones (e.g. rosiglitazone, pioglitazone), SGLT 2 inhibitors (e.g. dapagliflozin, remogliflozin etabonate, sergliflozin, canagliflozin), PPAR-gamma-agonists (e.g. GI 262570) and antagonists, PPAR-gamma/alpha modulators (e.g. KRP 297), alphaglucosidase inhibitors (e.g. acarbose, voglibose), DPPIV inhibitors (e.g. Sitagliptin, Vildagliptin, Saxagliptin, Alogliptin, Linagliptin), alpha2-antagonists, insulin and insulin analogues, GLP-1 and GLP-1 analogues (e.g. exendin-4) or amylin. The list also includes inhibitors of protein tyrosinephosphatase 1, substances that affect deregulated glucose production in the liver, such as e.g. inhibitors of glucose-6-phosphatase, or fructose-1,6-bisphosphatase, glycogen phosphorylase, glucagon receptor antagonists and inhibitors of phosphoenol pyruvate carboxykinase, glycogen synthase kinase or pyruvate dehydrokinase and glucokinase activators, lipid lowering agents such as for example HMG-CoA-reductase inhibitors (e.g. simvastatin, atorvastatin), fibrates (e.g. bezafibrate, fenofibrate), nicotinic acid and the derivatives thereof, PPAR-alpha agonists, PPAR-delta agonists, ACAT inhibitors (e.g. avasimibe) or cholesterol absorption inhibitors such as, for example, ezetimibe, bile acid-binding substances such as, for example, cholestyramine, inhibitors of ileac bile acid transport, HDL-raising compounds such as CETP inhibitors or ABC1 regulators or active substances for treating obesity, such as sibutramine or tetrahydrolipostatin, SDRIs, axokine, leptin, leptin mimetics, antagonists of the cannabinoid) receptor, MCH-1 receptor antagonists, MC4 receptor agonists, NPY5 or NPY2 antagonists or β3-agonists such as SB-418790 or AD-9677 and agonists of the 5HT2c receptor.

Moreover, combinations with drugs for influencing high blood pressure, chronic heart failure or atherosclerosis such as e.g. A-II antagonists or ACE inhibitors, ECE inhibitors, diuretics, β-blockers, Ca-antagonists, centrally acting antihypertensives, antagonists of the alpha-2-adrenergic receptor, inhibitors of neutral endopeptidase, thrombocyte aggregation inhibitors and others or combinations thereof are suitable. Examples of angiotensin II receptor antagonists are candesartan cilexetil, potassium losartan, eprosartan mesylate, valsartan, telmisartan, irbesartan, EXP-3174, L-158809, EXP-3312, olmesartan, medoxomil, tasosartan, KT-3-671, GA-0113, RU-64276, EMD-90423, BR-9701, etc. Angiotensin II receptor antagonists are preferably used for the treatment or prevention of high blood pressure and complications of diabetes, often combined with a diuretic such as hydrochlorothiazide.

A combination with uric acid synthesis inhibitors or uricosurics is suitable for the treatment or prevention of gout.

A combination with GABA-receptor antagonists, Na-channel blockers, topiramat, proteinkinase C inhibitors, advanced glycation end product inhibitors or aldose reductase inhibitors may be used for the treatment or prevention of complications of diabetes.

The dosage for the combination partners mentioned above is usefully ⅕ of the lowest dose normally recommended up to 1/1 of the normally recommended dose.

Therefore, in another aspect, this invention relates to the use of a compound according to the invention or a physiologically acceptable salt of such a compound combined with at least one of the active substances described above as a combination partner, for preparing a pharmaceutical composition which is suitable for the treatment or prevention of diseases or conditions which can be affected by inhibiting the enzyme 11β-hydroxysteroid dehydrogenase (HSD) 1. These are preferably metabolic diseases, particularly one of the diseases or conditions listed above, most particularly diabetes or diabetic complications.

The use of the compound according to the invention, or a physiologically acceptable salt thereof, in combination with another active substance may take place simultaneously or at staggered times, but particularly within a short space of time. If they are administered simultaneously, the two active substances are given to the patient together; while if they are used at staggered times the two active substances are given to the patient within a period of less than or equal to 12 hours, but particularly less than or equal to 6 hours.

Consequently, in another aspect, this invention relates to a pharmaceutical composition which comprises a compound according to the invention or a physiologically acceptable salt of such a compound and at least one of the active substances described above as combination partners, optionally together with one or more inert carriers and/or diluents.

Thus, for example, a pharmaceutical composition according to the invention comprises a combination of a compound of formula I according to the invention or a physiologically acceptable salt of such a compound and at least one angiotensin II receptor antagonist optionally together with one or more inert carriers and/or diluents.

The compound according to the invention, or a physiologically acceptable salt thereof, and the additional active substance to be combined therewith may both be present together in one formulation, for example a tablet or capsule, or separately in two identical or different formulations, for example as a so-called kit-of-parts.

The Examples that follow are intended to illustrate the present invention without restricting it:
LC Method 1:

| Column | Merck Cromolith Speed ROD, RP18e, 50 × 4.6 mm | | |
|---|---|---|---|
| Mobile Phase | A: water + 0.1% HCO$_2$H | | |
| | B: acetonitrile + 0.1% HCO$_2$H | | |
| | TIME (min) | A % | B % |
| | 0.00 | 90 | 10 |
| | 4.50 | 10 | 90 |
| | 5.00 | 10 | 90 |
| | 5.50 | 90 | 10 |
| Flow Rate | 1.5 mL/min | | |
| Wavelength | UV 220, 230, or 254 nm | | |

Preparation of the Starting Compounds

EXAMPLE I

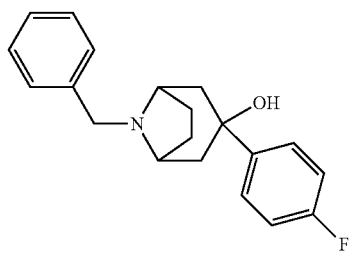 [SMILES: OC1(c2ccc(F)cc2)CC2CCC(C1)N2Cc1ccccc1]

8-Benzyl-3-(4-fluoro-phenyl)-8-aza-bicyclo[3.2.1]
oct-3-ol

1-Bromo-4-fluoro-benzene (22.7 g) dissolved in diethylether (100 mL) is added to a solution of n-butyllithium (1.7 mol/L in pentane, 86.8 mL) in diethylether (200 mL) cooled to −35° C. The combined solutions are stirred at −35 to −40° C. for 1 h, before 8-benzyl-8-aza-bicyclo[3.2.1]octan-3-one (22.5 g) dissolved in diethylether (150 mL) is added quickly. The solution is warmed to −10° C. within 1 h and then the reaction is quenched by the addition of aqueous NH$_4$Cl solution. The resulting mixture is extracted with ethyl acetate, the combined extracts are washed with brine, and 4 M hydrochloric acid is added to the organic phase. The organic phase is separated from the aqueous phase and an oily precipitation formed after the addition. The oily and aqueous phase are combined and basified with 4 M aqueous NaOH solution and the resulting mixture is extracted with ethyl acetate. The organic extracts are dried (Na$_2$SO$_4$) and the solvent is evaporated to give the title compound.

Yield: 21.0 g (75% of theory)

Mass spectrum (ESI$^+$): m/z=312 [M+H]$^+$

EXAMPLE II

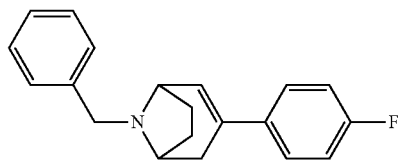 [SMILES: Fc1ccc(C2=CC3CCC(C2)N3Cc2ccccc2)cc1]

8-Benzyl-3-(4-fluoro-phenyl)-8-aza-bicyclo[3.2.1]
oct-2-ene

A solution of 8-benzyl-3-(4-fluoro-phenyl)-8-aza-bicyclo [3.2.1]octan-3-ol (21.0 g) in concentrated aqueous hydrochloric acid (80 mL) is stirred at reflux temperature for 1 h. After cooling to ambient temperature, the solution is basified by the addition of 4 M aqueous NaOH solution. The resulting mixture is extracted with ethyl acetate and the combined extracts are dried (Na$_2$SO$_4$). The solvent is evaporated and the residue is dissolved in diethyl ether. Methanesulfonic acid (4.3 mL) is added and the solvent is removed under reduced pressure to give the methanesulfonic acid salt of the title compound.

Yield: 19.1 g (73% of theory)

EXAMPLE III

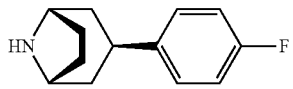

endo-3-(4-Fluoro-phenyl)-8-aza-bicyclo[3.2.1]octane

A mixture of the methanesulfonic acid salt of 8-benzyl-3-(4-fluoro-phenyl)-8-aza-bicyclo[3.2.1]oct-2-ene (from Example II, 19.1 g) and 5% palladium on carbon (2 g) in methanol (170 mL) is shaken under hydrogen atmosphere (5 bar) at 55° C. overnight. Then, the catalyst is separated by filtration and the filtrate is concentrated. The residue is taken up in ethyl acetate and washed with saturated aqueous K$_2$CO$_3$ solution. The organic phase is concentrated and the residue is purified by chromatography on silica gel (dichloromethane/methanol 99:1→9:1).

Yield: 3.5 g (35% of theory)

LC (method 1): t$_R$=1.82 min; Mass spectrum (ESI$^+$): m/z=206 [M+H]$^+$

EXAMPLE IV

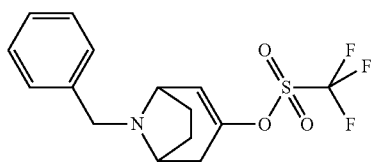 [SMILES: O=S(=O)(OC1=CC2CCC(C1)N2Cc1ccccc1)C(F)(F)F]

Trifluoro-methanesulfonic acid
8-benzyl-8-aza-bicyclo[3.2.1]oct-2-en-3-yl ester

Lithium bis(trimethylsilyl)amide (1 mol/L in tetrahydrofuran, 51.5 mL) is added to a solution of 8-benzyl-8-aza-bicyclo[3.2.1]octan-3-one (10.6 g) in tetrahydrofuran (200 mL) cooled to −78° C. The solution is stirred at −78° C. for 1 h, before 2-(N,N-(bistrifluoromethylsulfonyl)amino)-5-chloropyridine (20.8 g) dissolved in tetrahydrofuran (200 mL) is added dropwise. The resulting solution is stirred for another 0.5 h at this temperature and then warmed to room temperature by removing the cooling bath. Then, aqueous NaHCO$_3$ solution is added, the resulting mixture is extracted with ethyl acetate, and the combined extracts are dried (Na$_2$SO$_4$). After removal of the solvent under reduced pressure, the residue is purified by chromatography on silica gel (cyclohexane/ethyl acetate 1:0→1:1).

Yield: 10.5 g (62% of theory)

Mass spectrum (ESI$^+$): m/z=348 [M+H]$^+$

Alternatively, the title compound is obtained analogously to the procedure described above using sodium bis(trimethylsilyl)amide as base and N,N-bis(trifluoromethylsulfonyl)aniline as sulfonylating agent.

The following compound is obtained analogously to Example IV:

(1) Trifluoro-methanesulfonic acid 8-methyl-8-aza-bicyclo[3.2.1]oct-2-en-3-yl ester

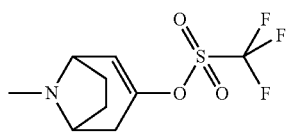 [SMILES: CN1C2C=C(OS(=O)(=O)C(F)(F)F)CC1CC2]

Mass spectrum (ESI$^+$): m/z=272 [M+H]$^+$

Potassium bis(trimethylsilyl)amide and N,N-bis(trifluoromethylsulfonyl)aniline may be used as the base and sulfonylating agent, respectively, instead of the reagents described above.

EXAMPLE V

8-Benzyl-3-(4-methoxy-phenyl)-8-aza-bicyclo[3.2.1]oct-2-ene

4-Methoxyphenyl boronic acid (0.50 g), lithium chloride (0.26 g), Pd(PPh$_3$)$_4$ (0.17 g), and finally 2 M aqueous Na$_2$CO$_3$ solution (3.2 mL) are added in turn to a flask charged with a stir bar, trifluoromethanesulfonic acid 8-benzyl-8-aza-bicyclo[3.2.1]oct-2-en-3-yl ester (1.0 g), water (5 mL), and 1,2-dimethoxyethane (25 mL) under argon atmosphere. The resulting mixture is stirred at reflux temperature for 5 h. After cooling to ambient temperature, brine is added and the mixture is extracted with ethyl acetate. The combined extracts are dried (Na$_2$SO$_4$) and the solvent is removed under reduced pressure. The residue is purified by chromatography on silica gel (cyclohexane/ethyl acetate 1:0→1:1).

Yield: 0.62 g (71% of theory)

The following compounds are obtained analogously to Example V:

(1) 3-(4-Fluoro-phenyl)-8-methyl-8-aza-bicyclo[3.2.1]oct-2-ene

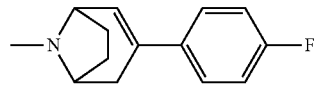 [SMILES: CN1C2C=C(c3ccc(F)cc3)CC1CC2]

Mass spectrum (ESI$^+$): m/z=218 [M+H]$^+$ (2) 8-Benzyl-3-(3,4-difluoro-phenyl)-8-aza-bicyclo[3.2.1]oct-2-ene

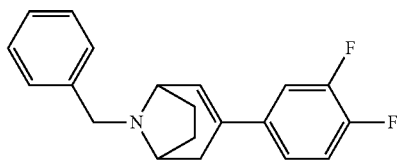 [SMILES: Fc1ccc(C2=CC3CCC(C2)N3Cc2ccccc2)cc1F]

Mass spectrum (ESI$^+$): m/z=312 [M+H]$^+$ (3) 8-Benzyl-3-(3-methoxy-phenyl)-8-aza-bicyclo[3.2.1]oct-2-ene

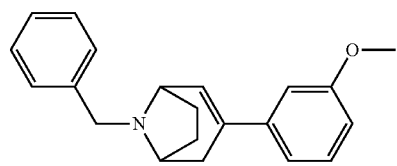 [SMILES: COc1cccc(C2=CC3CCC(C2)N3Cc2ccccc2)c1]

(4) 8-Benzyl-3-p-tolyl-8-aza-bicyclo[3.2.1]oct-2-ene

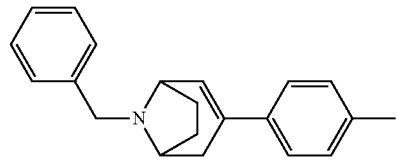 [SMILES: Cc1ccc(C2=CC3CCC(C2)N3Cc2ccccc2)cc1]

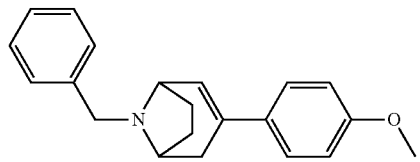

(5) 8-Benzyl-3-(4-isopropyl-phenyl)-8-aza-bicyclo[3.2.1]oct-2-ene

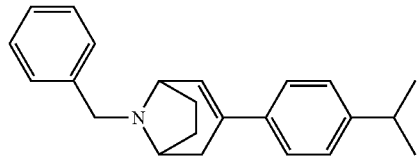 [SMILES: CC(C)c1ccc(C2=CC3CCC(C2)N3Cc2ccccc2)cc1]

Mass spectrum (ESI⁺): m/z=318 [M+H]⁺

(6) 8-Benzyl-3-(4-trifluoromethoxy-phenyl)-8-aza-bicyclo[3.2.1]oct-2-ene

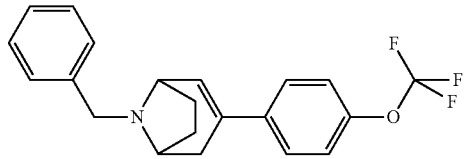 [SMILES: FC(F)(F)Oc1ccc(C2=CC3CCC(C2)N3Cc2ccccc2)cc1]

Mass spectrum (ESI⁺): m/z=360 [M+H]⁺

(7) 8-Benzyl-3-(4-phenoxy-phenyl)-8-aza-bicyclo[3.2.1]oct-2-ene

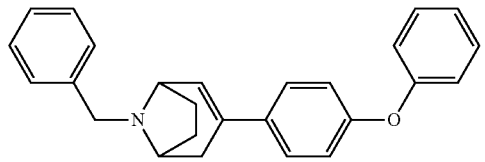 [SMILES: C1=C(c2ccc(Oc3ccccc3)cc2)CC2CCC1N2Cc1ccccc1]

(8) 8-Benzyl-3-(4-trimethylsilanyl-phenyl)-8-aza-bicyclo[3.2.1]oct-2-ene

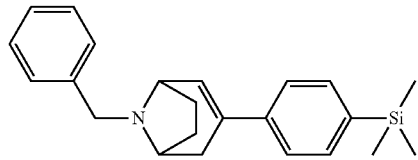 [SMILES: C[Si](C)(C)c1ccc(C2=CC3CCC(C2)N3Cc2ccccc2)cc1]

(9) 4-(8-Benzyl-8-aza-bicyclo[3.2.1]oct-2-en-3-yl)-benzoic acid methyl ester

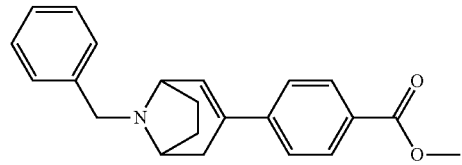 [SMILES: COC(=O)c1ccc(C2=CC3CCC(C2)N3Cc2ccccc2)cc1]

(10) 8-Benzyl-3-(4-methoxymethyl-phenyl)-8-aza-bicyclo[3.2.1]oct-2-ene

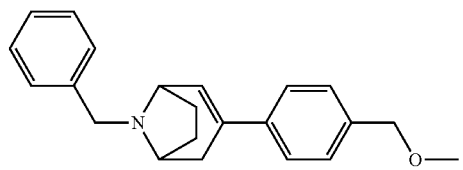 [SMILES: COCc1ccc(C2=CC3CCC(C2)N3Cc2ccccc2)cc1]

(11) 8-Benzyl-3-thiophen-2-yl-8-aza-bicyclo[3.2.1]oct-2-ene

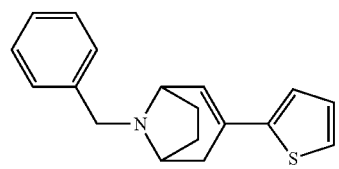 [SMILES: C1=C(c2cccs2)CC2CCC1N2Cc1ccccc1]

(12) 8-Benzyl-3-thiophen-3-yl-8-aza-bicyclo[3.2.1]oct-2-ene

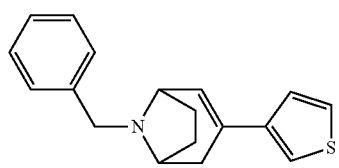 [SMILES: C1=C(c2ccsc2)CC2CCC1N2Cc1ccccc1]

(13) 8-Benzyl-3-pyridin-3-yl-8-aza-bicyclo[3.2.1]oct-2-ene

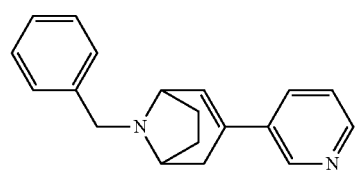 [SMILES: C1=C(c2cccnc2)CC2CCC1N2Cc1ccccc1]

(14) 8-Benzyl-3-pyridin-3-yl-8-aza-bicyclo[3.2.1]oct-2-ene

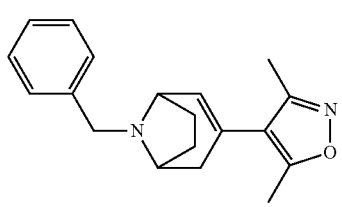 [SMILES: Cc1noc(C)c1C1=CC2CCC(C1)N2Cc1ccccc1]

(15) 8-Benzyl-3-o-tolyl-8-aza-bicyclo[3.2.1]oct-2-ene

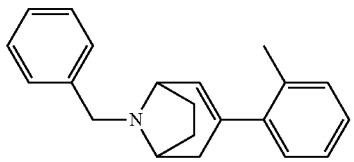 [SMILES: Cc1ccccc1C1=CC2CCC(C1)N2Cc1ccccc1]

Mass spectrum (ESI⁺): m/z=290 [M+H]⁺

(16) 8-Benzyl-3-(2-methoxy-phenyl)-8-aza-bicyclo[3.2.1]oct-2-ene

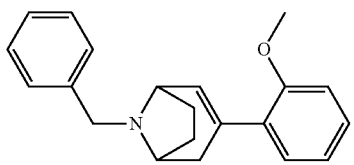

Mass spectrum (ESI⁺): m/z=306 [M+H]⁺

(17) 8-Benzyl-3-(2,6-difluoro-phenyl)-8-aza-bicyclo[3.2.1]oct-2-ene

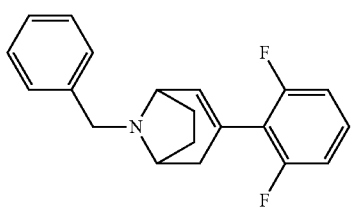 [SMILES: Fc1cccc(F)c1C1=CC2CCC(C1)N2Cc1ccccc1]

Mass spectrum (ESI⁺): m/z=312 [M+H]⁺

(18) 8-Benzyl-3-(2,4-difluoro-phenyl)-8-aza-bicyclo[3.2.1]oct-2-ene

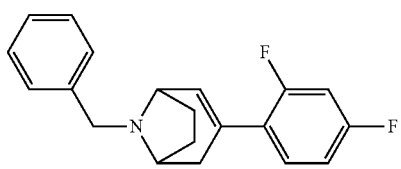

Mass spectrum (ESI⁺): m/z=312 [M+H]⁺

(19) 8-Benzyl-3-(4-naphthalen-2-yl-phenyl)-8-aza-bicyclo[3.2.1]oct-2-ene

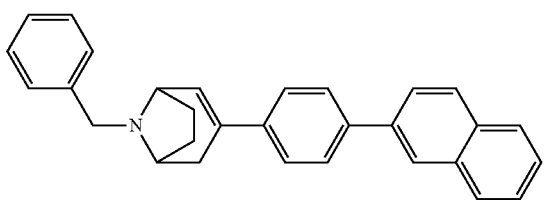 [SMILES: C1=C(c2ccc(-c3ccc4ccccc4c3)cc2)CC2CCC1N2Cc1ccccc1]

Mass spectrum (ESI⁺): m/z=326 [M+H]⁺

(20) 8-Benzyl-3-pyrimidin-5-yl-8-aza-bicyclo[3.2.1]oct-2-ene

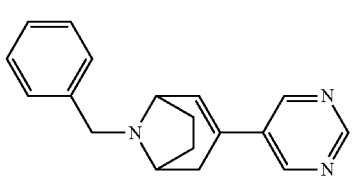 [SMILES: C1=C(c2cncnc2)CC2CCC1N2Cc1ccccc1]

Mass spectrum (ESI⁺): m/z=278 [M+H]⁺

(21) 8-Benzyl-3-furan-3-yl-8-aza-bicyclo[3.2.1]oct-2-ene

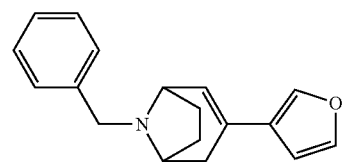 [SMILES: C1=C(c2ccoc2)CC2CCC1N2Cc1ccccc1]

Mass spectrum (ESI⁺): m/z=266 [M+H]⁺

(22) 8-Benzyl-3-pyridin-4-yl-8-aza-bicyclo[3.2.1]oct-2-ene

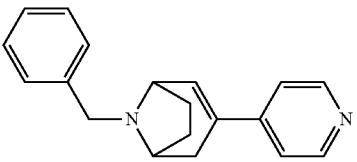 [SMILES: C1=C(c2ccncc2)CC2CCC1N2Cc1ccccc1]

EXAMPLE VI

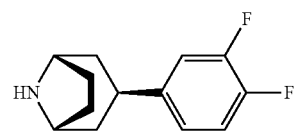

endo-3-(3,4-Difluoro-phenyl)-8-aza-bicyclo[3.2.1]octane

A mixture of 8-benzyl-3-(3,4-difluoro-phenyl)-8-aza-bicyclo[3.2.1]oct-2-ene (0.30 g) and 5% palladium on carbon (40 mg) in ethanol (5 mL) containing acetic acid (0.15 mL) is shaken under hydrogen atmosphere (5 bar) at 60° C. overnight. Then, the catalyst is separated by filtration and the filtrate is concentrated. The residue is purified by chromatography on silica gel (dichloromethane/methanol 99:1→9:1).

Yield: 0.16 g (74% of theory)

Alternatively, the transformation is carried out with no or only 1 equivalent of acid and palladium(II) hydroxide as catalyst.

The following compounds are obtained analogously to Example VI:

(1) endo-3-(4-Methoxy-phenyl)-8-aza-bicyclo[3.2.1]octane

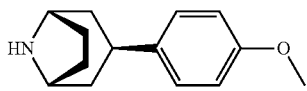

(2) endo-3-p-Tolyl-8-aza-bicyclo[3.2.1]octane

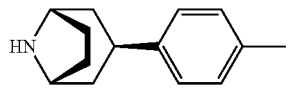

(3) endo-3-(3-Methoxy-phenyl)-8-aza-bicyclo[3.2.1]octane

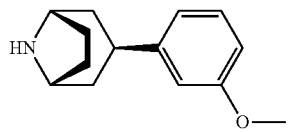

(4) endo-3-(4-Trifluoromethoxy-phenyl)-8-aza-bicyclo[3.2.1]octane

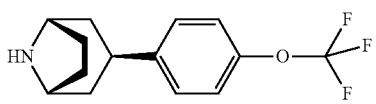

(5) endo-3-(4-Isopropyl-phenyl)-8-aza-bicyclo[3.2.1]octane

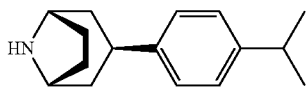

(6) endo-3-(4-Phenoxy-phenyl)-8-aza-bicyclo[3.2.1]octane

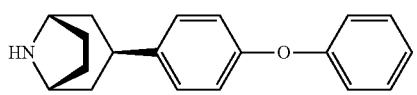

(7) endo-3-(4-Trimethylsilanyl-phenyl)-8-aza-bicyclo[3.2.1]octane

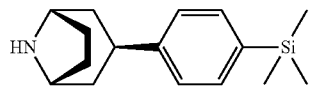

(8) endo-4-(8-Aza-bicyclo[3.2.1]oct-3-yl)-benzoic acid methyl ester

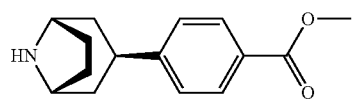

(9) endo-3-(4-Methoxymethyl-phenyl)-8-aza-bicyclo[3.2.1]octane

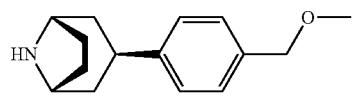

(10) endo-3-Pyridin-3-yl-8-aza-bicyclo[3.2.1]octane

(11) endo-3-(3,5-Dimethyl-isoxazol-4-yl)-8-aza-bicyclo[3.2.1]octane

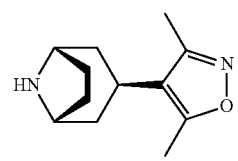

(12) endo-3-(2-Methoxy-phenyl)-8-aza-bicyclo[3.2.1]octane

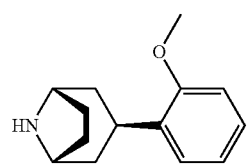

Mass spectrum (ESI$^+$): m/z=218 [M+H]$^+$

(13) endo-3-o-Tolyl-8-aza-bicyclo[3.2.1]octane

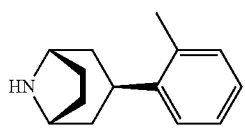

(14) endo-3-(2,6-Difluoro-phenyl)-8-aza-bicyclo[3.2.1]octane

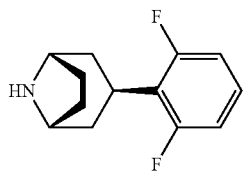

Mass spectrum (ESI$^+$): m/z=224 [M+H]$^+$

(15) endo-3-(2,4-Difluoro-phenyl)-8-aza-bicyclo[3.2.1]octane

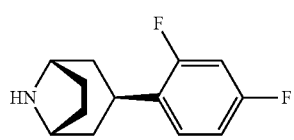

Mass spectrum (ESI$^+$): m/z=224 [M+H]$^+$

(16) endo-3-Naphthalen-2-yl-8-aza-bicyclo[3.2.1]octane

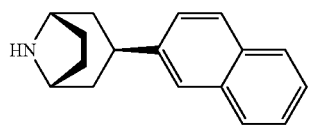

Mass spectrum (ESI$^+$): m/z=238 [M+H]$^+$

Remark: The products obtained in analogy to the procedure described above mostly have high isomeric purity (endo/exo in most cases >9:1).

The following compounds may be obtained analogously to Example VI from the respective precursors described under Example V:

(17) endo-3-Thiophen-2-yl-8-aza-bicyclo[3.2.1]octane

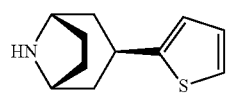

(18) endo-3-Thiophen-3-yl-8-aza-bicyclo[3.2.1]octane

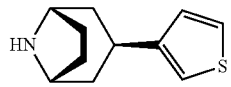

(19) endo-3-Pyrimidin-5-yl-8-aza-bicyclo[3.2.1]octane

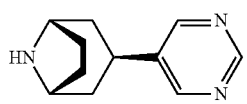

(20) endo-3-Furan-3-yl-8-aza-bicyclo[3.2.1]octane

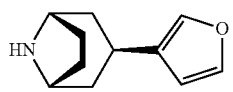

(21) endo-3-Pyridin-4-yl-8-aza-bicyclo[3.2.1]octane

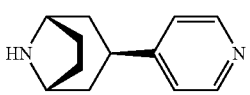

EXAMPLE VII

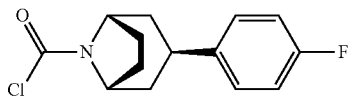

endo-3-(4-Fluoro-phenyl)-8-aza-bicyclo[3.2.1]octane-8-carbonyl chloride

A solution of 3-(4-fluoro-phenyl)-8-aza-bicyclo[3.2.1]octane (2.50 g) and triethylamine (2.0 mL) in anhydrous toluene (30 mL) is added dropwise to a solution of phosgene (20 weight % in toluene, 6.7 mL) in anhydrous toluene (15 mL) chilled to 0° C. The formed suspension is allowed to warm to room temperature and stirred for 2 h. Then, the mixture is cooled to 0° C. and half-saturated aqueous NaHCO$_3$ solution is added slowly. The mixture is extracted with ethyl acetate, the combined extracts are dried (Na$_2$SO$_4$), and the solvent is evaporated to give the product as a pale yellow solid which is used without further purification.

Yield: 3.25 g (99% of theory)

EXAMPLE VIII

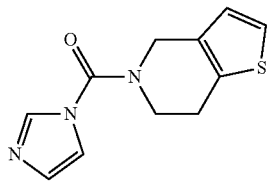 [SMILES: O=C(N1CCc2sccc2C1)n1ccnc1]

(6,7-Dihydro-4H-thieno[3,2-c]pyridin-5-yl)-imidazol-1-yl-methanone

A solution of 4,5,6,7-tetrahydro-thieno[3,2-c]pyridine (0.50 g) and N,N'-carbonyldiimidazole (0.64 g) in tetrahydrofuran (20 mL) is stirred at 60° C. for 24 h. After cooling to room temperature, the solution is concentrated and the residue is chromatographed on silica gel (cyclohexane/ethyl acetate 90:1020:80) to afford the title compound.
Yield: 0.10 g (12% of theory)

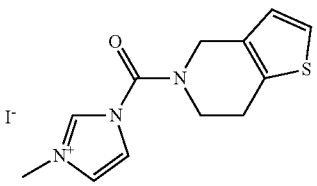 [SMILES: [I-] ; C[n+]1ccn(C(=O)N2CCc3sccc3C2)c1]

EXAMPLE IX 3-(6,7-Dihydro-4H-thieno[3,2-c]pyridine-5-carbonyl)-1-methyl-3H-imidazol-1-ium iodide Methyl iodide (50 μL) is added to a solution of (6,7-dihydro-4H-thieno[3,2-c]pyridin-5-yl)imidazol-1-yl-methanone (100 mg) in acetonitrile (5 mL) at room temperature. The solution is stirred for 5 h, before more methyl iodide (100 μL) is added. After stirring the solution for another 10 h, the solution is concentrated to give the crude title compound that is used without further purification.
Yield: 0.15 g Preparation of the End Compounds Procedure A (Described for Example 1, Table 3)

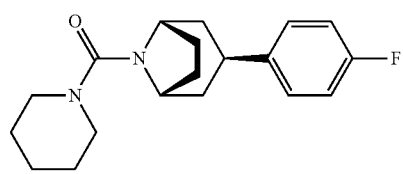

endo-[3-(4-Fluoro-phenyl)-8-aza-bicyclo[3.2.1]oct-8-yl]-piperidin-1-yl-methanone Piperidine-1-carbonyl chloride (80 μL) is added to a solution of 3-(4-fluoro-phenyl)-8-aza-bicyclo[3.2.1]octane (0.10 g) and ethyldiisopropylamine (0.25 mL) in dichloromethane (2 mL). The resulting mixture is stirred at room temperature overnight. Then, aqueous NaHCO$_3$ solution is added and the mixture is extracted with dichloromethane. The combined organic extracts are dried (Na$_2$SO$_4$) and the solvent is evaporated. The residue is purified by flash chromatography on silica gel (hexane/ethyl acetate 2:1) to give the title compound as a white solid.
Yield: 0.14 g (93% of theory)
Mass spectrum (ESI$^+$): m/z=317 [M+H]$^+$ Procedure B (Described for Example 13, Table 3)

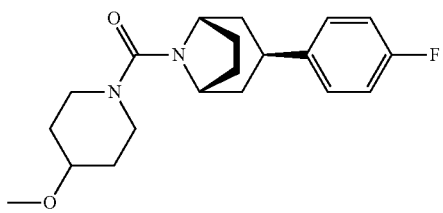

endo-[3-(4-Fluoro-phenyl)-8-aza-bicyclo[3.2.1]oct-8-yl]-(4-methoxy-piperidin-1-yl)-methanone A solution of triethylamine (57 μL) and 3-(4-fluoro-phenyl)-8-aza-bicyclo[3.2.1]octane (60 mg) in dichloromethane (2 mL) is added to a solution of phosgene (20% in toluene, 0.18 mL) in dichloromethane (2 mL) chilled in an ice bath. The resulting solution is stirred for 0.5 h in the cooling bath and 0.5 h at room temperature (conversion to the carbamoyl chloride is monitored by trapping a sample of the intermediate with dimethylamine and detecting the dimethyl urea derivative by TLC or HPLC), prior to the addition of 4-methoxy-piperidine (52 mg). The resulting mixture is stirred at room temperature overnight. Then, dichloromethane is added and the resulting mixture is washed with aqueous NaHCO$_3$ solution and dried (Na$_2$SO$_4$). The solvent is evaporated and the residue is chromatographed on silica gel (dichloromethane/methanol 1:09:1) to afford the title compound.
Yield: 37 mg (37% of theory)
LC (method 1): t$_R$=3.97 min; Mass spectrum (ESI$^+$): m/z=347 [M+H]$^+$
Remark: The order of addition of the two amino compounds to phosgene may be reversed and triphosgene or diphosgene instead of phosgene may be used as well.

Procedure C (Described for Example 4, Table 3)

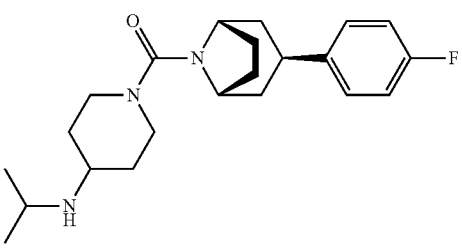

endo-N-{1-[3-(4-Fluoro-phenyl)-8-aza-bicyclo[3.2.1]octane-8-carbonyl]-piperidin-4-yl}-acetamide Ethyldiisopropylamine (0.25 mL) and 4-acetylaminopiperidine (104 mg) are added in turn to a solution of endo-3-(4-fluoro-phenyl)-8-aza-bicyclo[3.2.1]octane-8-carbonyl chloride (135 mg) in anhydrous dichloromethane (3 mL) chilled to 0° C. After stirring the mixture for a few minutes, the cooling bath is removed and the mixture is stirred at room temperature overnight. Aqueous NaHCO$_3$ solution is added and the mixture is extracted with dichloromethane. The combined organic extracts are dried (Na$_2$SO$_4$) and the solvent is evaporated. The residue is purified by flash chromatography on silica gel (ethanol/ethyl acetate 1:10→1:4) to afford the title compound as a white solid.

Yield: 165 mg (91% of theory)

Mass spectrum (ESI$^+$): m/z=374 [M+H]$^+$

Procedure D (Described for Example 11, Table 3)

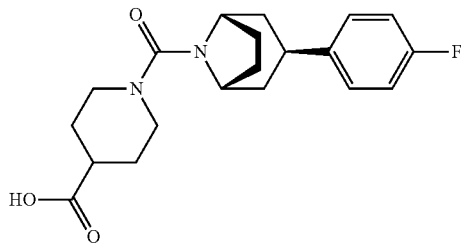

endo-1-[3-(4-Fluoro-phenyl)-8-aza-bicyclo[3.2.1]octane-8-carbonyl]-piperidine-4-carboxylic acid Aqueous 2 N LiOH solution (1.5 mL) is added slowly to a solution of endo-1-[3-(4-fluorophenyl)-8-aza-bicyclo[3.2.1]octane-8-carbonyl]-piperidine-4-carboxylic acid ethyl ester (0.29 g) in a mixture of tetrahydrofuran and water (2:1, 3 mL) chilled in an ice bath. After stirring for 30 min, the cooling bath is removed and the mixture is stirred at room temperature for 2 h. The solution is cooled again to 0° C. and 1 N hydrochloric acid is added slowly to adjust the pH value of the solution to 3. The forming precipitate is separated by filtration and washed consecutively with water and diethyl ether to afford the title compound as a white solid.

Yield: 205 mg (76% of theory)

Mass spectrum (ESI$^+$): m/z=361 [M+H]$^+$

Procedure E (Described for Example 12, Table 3)

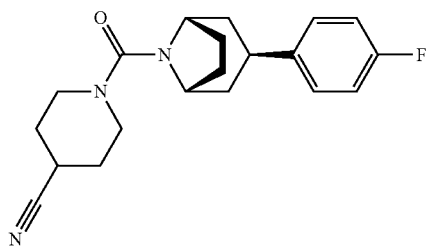

endo-1-[3-(4-Fluoro-phenyl)-8-aza-bicyclo[3.2.1]octane-8-carbonyl]-piperidine-4-carbonitrile Trifluoroacetic anhydride (47 µL) is added to a solution of endo-1-[3-(4-fluoro-phenyl)-8-aza-bicyclo[3.2.1]octane-8-carbonyl]-piperidine-4-carboxylic acid amide (95 mg) and triethylamine (84 µL) in dichloromethane (3 mL) chilled in an ice bath. The cooling bath is removed and the solution is stirred at room temperature overnight. The solution is diluted with dichloromethane and the resulting solution is washed with aqueous NaHCO$_3$ solution and dried (Na$_2$SO$_4$). The solvent is evaporated and the residue is chromatographed on silica gel (cyclohexane/ethyl acetate 1:01:1) to afford the title compound.

Yield: 60 mg (66% of theory)

LC (method 1): t$_R$=3.88 min; Mass spectrum (ESI$^+$): m/z=342 [M+H]$^+$

Procedure F (Described for Example 15, Table 3)

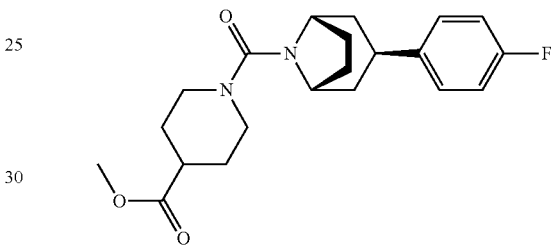

endo-1-[3-(4-Fluoro-phenyl)-8-aza-bicyclo[3.2.1]octane-8-carbonyl]-piperidine-4-carboxylic acid methyl ester Thionyl chloride (83 µL) is added to a solution of endo-1-[3-(4-fluoro-phenyl)-8-aza-bicyclo[3.2.1]octane-8-carbonyl]-piperidine-4-carboxylic acid (200 mg) in methanol (2 mL) chilled in an ice bath. The solution is stirred for 2 h while warming to room temperature in the cooling bath. Then, the solution is concentrated and the residue is taken up in ethyl acetate. The resulting solution is washed with aqueous NaHCO$_3$ solution, dried (Na$_2$SO$_4$), and concentrated under reduced pressure to give the title compound.

Yield: 190 mg (91% of theory)

LC (method 1): t$_R$=4.08 min; Mass spectrum (ESI$^+$): m/z=375 [M+H]$^+$

Procedure G (Described for Example 21, Table 3)

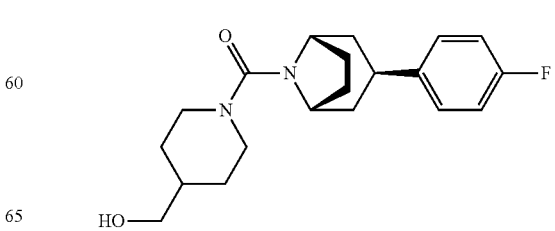

endo-[3-(4-Fluoro-phenyl)-8-aza-bicyclo[3.2.1]oct-8-yl]-(4-hydroxymethyl-piperidin-1-yl)methanone Lithium aluminum hydride (1 mol/L in tetrahydrofuran, 68 µL) is added to a solution of endo-1-[3-(4-fluoro-phenyl)-8-aza-bicyclo[3.2.1]octane-8-carbonyl]-piperidine-4-carboxylic acid methyl ester (50 mg) in tetrahydrofuran (4 mL) chilled to −20° C. After stirring the solution at −20° C. for 1 h, another portion of lithium aluminum hydride (50 µL) is added. The solution is stirred for one more hour and then poured into ice-cold water. 1 M aqueous NaOH solution is added to the mixture that is then extracted with ethyl acetate. The combined extracts are dried ($Na_2SO_4$) and the solvent is evaporated to afford the title compound.

Yield: 30 mg (65% of theory)
LC (method 1): $t_R$=3.48 min; Mass spectrum (ESI$^+$): m/z=347 [M+H]$^+$ Procedure H (Described for Example 21, Table 3)

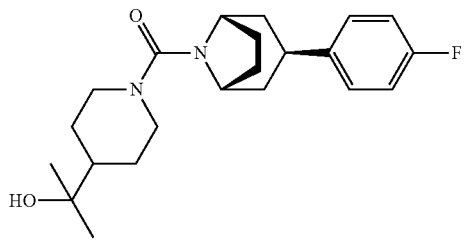

endo-[3-(4-Fluoro-phenyl)-8-aza-bicyclo[3.2.1]oct-8-yl]-[4-(1-hydroxy-1-methyl-ethyl)piperidin-1-yl]-methanone Methyl lithium (1.6 mol/L in diethylether, 106 µL) is added to a solution of endo-1-[3-(4-fluorophenyl)-8-aza-bicyclo[3.2.1]octane-8-carbonyl]-piperidine-4-carboxylic acid methyl ester (30 mg) in tetrahydrofuran (4 mL) cooled to −78° C. The solution is stirred at −78° C. for 1 h prior to the addition of aqueous $NH_4Cl$ solution. The resulting mixture is extracted with ethyl acetate and the combined extracts are dried ($Na_2SO_4$) and concentrated to afford the title compound.

Yield: 30 mg (100% of theory)
LC (method 1): $t_R$=3.80 min; Mass spectrum (ESI$^+$): m/z=375 [M+H]$^+$ Procedure I (Described for Example 7, Table 3)

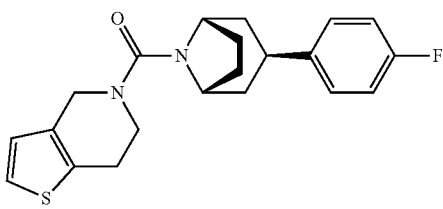

endo-(6,7-Dihydro-4H-thieno[3,2-c]pyridin-5-yl)-[3-(4-fluoro-phenyl)-8-aza-bicyclo[3.2.1]oct-8-yl]-methanone 3-(4-Fluoro-phenyl)-8-aza-bicyclo[3.2.1]octane (88 mg) and triethylamine (65 µL) are added to a solution of 3-(6,7-dihydro-4H-thieno[3,2-c]pyridine-5-carbonyl)-1-methyl-3H-imidazol-1-ium iodide (150 mg, crude from Example IX) in dichloromethane (5 mL) at room temperature. The resulting solution is stirred at room temperature for 16 h. Then dichloromethane is added and the resulting solution is washed with water and brine. The solvent is evaporated and the residue is purified by HPLC on reversed phase (MeCN/water) to afford the title compound.

Yield: 35 mg (22% of theory)
Mass spectrum (ESI$^+$): m/z=371 [M+H]$^+$

TABLE 3

| | Compilation of prepared end compounds | | |
|---|---|---|---|
| Example No. | Chemical Name/Structure/Remark | Prepared in analogy to Procedure | Characterization |
| 1 | endo-[3-(4-Fluoro-phenyl)-8-aza-bicyclo[3.2.1]oct-8-yl]-piperidin-1-yl-methanone | A | Mass spectrum (ESI$^+$): m/z = 317 [M + H]$^+$ |
| 2 | endo-[3-(4-Fluoro-phenyl)-8-aza-bicyclo[3.2.1]oct-8-yl]-pyrrolidin-1-yl-methanone | A | Mass spectrum (ESI$^+$): m/z = 303 [M + H]$^+$ |

TABLE 3-continued

Compilation of prepared end compounds

| Example No. | Chemical Name/Structure/Remark | Prepared in analogy to Procedure | Characterization |
|---|---|---|---|
| 3 | endo-[3-(4-Fluoro-phenyl)-8-aza-bicyclo[3.2.1]oct-8-yl]-morpholin-4-yl-methanone | A | Mass spectrum (ESI+): m/z = 319 [M + H]+ |
| 4 | endo-N-{1-[3-(4-Fluoro-phenyl)-8-aza-bicyclo[3.2.1]octane-8-carbonyl]-piperidin-4-yl}-acetamide | C | Mass spectrum (ESI+): m/z = 374 [M + H]+ |
| 5 | endo-[3-(4-Fluoro-phenyl)-8-aza-bicyclo[3.2.1]oct-8-yl]-(4-hydroxy-piperidin-1-yl)-methanone | C | Mass spectrum (ESI+): m/z = 333 [M + H]+ |
| 6 | endo-[3-(4-Fluoro-phenyl)-8-aza-bicyclo[3.2.1]oct-8-yl]-(3,4,6,7-tetrahydro-imidazo[4,5-c]pyridin-5-yl)-methanone | C | Mass spectrum (ESI+): m/z = 355 [M + H]+ |
| 7 | endo-(6,7-Dihydro-4H-thieno[3,2-c]pyridin-5-yl)-[3-(4-fluoro-phenyl)-8-aza-bicyclo[3.2.1]oct-8-yl]-methanone | I | Mass spectrum (ESI+): m/z = 371 [M + H]+ |

TABLE 3-continued

Compilation of prepared end compounds

| Example No. | Chemical Name/Structure/Remark | Prepared in analogy to Procedure | Characterization |
|---|---|---|---|
| 8 | [endo-3-(4-Fluoro-phenyl)-8-aza-bicyclo[3.2.1]oct-8-yl]-(endo-3-hydroxy-8-aza-bicyclo[3.2.1]oct-8-yl)-methanone | C | Mass spectrum (ESI$^+$): m/z = 359 [M + H]$^+$ |
| 9 | endo-1-[3-(4-Fluoro-phenyl)-8-aza-bicyclo[3.2.1]octane-8-carbonyl]-piperidine-4-carboxylic acid amide | C | Mass spectrum (ESI$^+$): m/z = 360 [M + H]$^+$ |
| 10 | endo-1-[3-(4-Fluoro-phenyl)-8-aza-bicyclo[3.2.1]octane-8-carbonyl]-piperidine-4-carboxylic acid ethyl ester | C | Mass spectrum (ESI$^+$): m/z = 389 [M + H]$^+$ |
| 11 | endo-1-[3-(4-Fluoro-phenyl)-8-aza-bicyclo[3.2.1]octane-8-carbonyl]-piperidine-4-carboxylic acid | D | Mass spectrum (ESI$^+$): m/z = 361 [M + H]$^+$ |

TABLE 3-continued

Compilation of prepared end compounds

| Example No. | Chemical Name/Structure/Remark | Prepared in analogy to Procedure | Characterization |
|---|---|---|---|
| 12 | endo-1-[3-(4-Fluoro-phenyl)-8-aza-bicyclo[3.2.1]octane-8-carbonyl]-piperidine-4-carbonitrile | E | LC (method 1): $t_R$ = 3.88 min; MS (ESI$^+$): m/z = 342 [M + H]$^+$ |
| 13 | endo-[3-(4-Fluoro-phenyl)-8-aza-bicyclo[3.2.1]oct-8-yl]-(4-methoxy-piperidin-1-yl)-methanone | B | LC (method 1): $t_R$ = 3.97 min; MS (ESI$^+$): m/z = 347 [M + H]$^+$ |
| 14 | endo-[3-(4-Fluoro-phenyl)-8-aza-bicyclo[3.2.1]oct-8-yl]-(4-hydroxy-4-trifluoromethyl-piperidin-1-yl)-methanone | B | LC (method 1): $t_R$ = 4.00 min; MS (ESI$^+$): m/z = 401 [M + H]$^+$ |
| 15 | endo-1-[3-(4-Fluoro-phenyl)-8-aza-bicyclo[3.2.1]octane-8-carbonyl]-piperidine-4-carboxylic acid methyl ester | F | LC (method 1): $t_R$ = 4.08 min; MS (ESI$^+$): m/z = 375 [M + H]$^+$ |

TABLE 3-continued

Compilation of prepared end compounds

| Example No. | Chemical Name/Structure/Remark | Prepared in analogy to Procedure | Characterization |
|---|---|---|---|
| 16 | endo-[3-(4-Fluoro-phenyl)-8-aza-bicyclo[3.2.1]oct-8-yl]-(4-hydroxy-4-methyl-piperidin-1-yl)-methanone 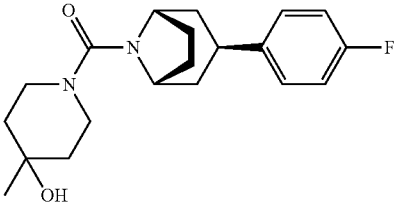 | B | LC (method 1): $t_R$ = 3.55 min; MS (ESI$^+$): m/z = 347 [M + H]$^+$ |
| 17 | endo-[3-(4-Fluoro-phenyl)-8-aza-bicyclo[3.2.1]oct-8-yl]-(3-hydroxy-3-trifluoromethyl-8-aza-bicyclo[3.2.1]oct-8-yl)-methanone 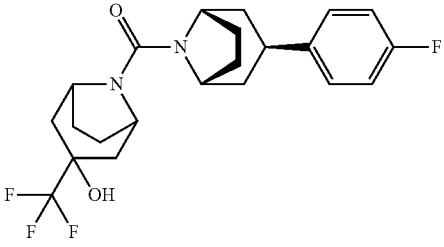 | B | LC (method 1): $t_R$ = 4.18 min; MS (ESI$^+$): m/z = 427 [M + H]$^+$ |
| 18 | endo-8-[3-(4-Fluoro-phenyl)-8-aza-bicyclo[3.2.1]octane-8-carbonyl]-2,8-diaza-spiro[5.5]undecan-1-one 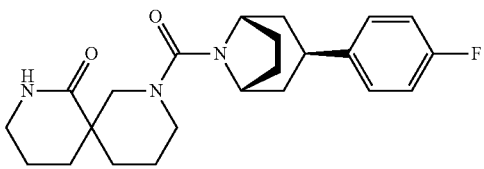 2,8-diaza-spiro[5.5]undecan-1-one, the coupling partner, is obtained by treatment of 7-oxo-2,8-diaza-spiro[5.5]undecane-2-carboxylic acid tert-butyl ester with HCl in 1,4-dioxane | B | LC (method 1): $t_R$ = 3.64 min; MS (ESI$^+$): m/z = 400 [M + H]$^+$ |
| 19 | endo-7-[3-(4-Fluoro-phenyl)-8-aza-bicyclo[3.2.1]octane-8-carbonyl]-2,7-diaza-spiro[4.5]decan-1-one 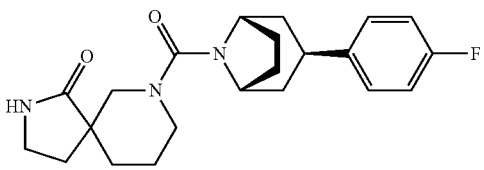 | B | LC (method 1): $t_R$ = 3.49 min; MS (ESI$^+$): m/z = 386 [M + H]$^+$ |

TABLE 3-continued

Compilation of prepared end compounds

| Example No. | Chemical Name/Structure/Remark | Prepared in analogy to Procedure | Characterization |
|---|---|---|---|
| 20 | endo-[3-(4-Fluoro-phenyl)-8-aza-bicyclo[3.2.1]oct-8-yl]-(3-hydroxymethyl-piperidin-1-yl)-methanone | B | LC (method 1): $t_R$ = 3.65 min; MS (ESI$^+$): m/z = 347 [M + H]$^+$ |
| 21 | endo-[3-(4-Fluoro-phenyl)-8-aza-bicyclo[3.2.1]oct-8-yl]-(4-hydroxymethyl-piperidin-1-yl)-methanone | G | LC (method 1): $t_R$ = 3.48 min; MS (ESI$^+$): m/z = 347 [M + H]$^+$ |
| 22 | endo-[3-(4-Fluoro-phenyl)-8-aza-bicyclo[3.2.1]oct-8-yl]-[4-(1-hydroxy-1-methyl-ethyl)-piperidin-1-yl]-methanone | H | LC (method 1): $t_R$ = 3.80 min; MS (ESI$^+$): m/z = 375 [M + H]$^+$ |

The following compounds are also prepared analogously to the above-mentioned Examples and other methods known from the literature starting from the respective precursors described under Example VI:

| Example No- | Chemical Name/Structure | In analogy to Procedure |
|---|---|---|
| 23 | endo-[3-(3,4-Difluoro-phenyl)-8-aza-bicyclo[3.2.1]oct-8-yl]-piperidin-1-yl-methanone | A |
| 24 | endo-[3-(4-Methoxy-phenyl)-8-aza-bicyclo[3.2.1]oct-8-yl]-piperidin-1-yl-methanone | A |

| Example No- | Chemical Name/Structure | In analogy to Procedure |
|---|---|---|
| 25 | endo-Piperidin-1-yl-(3-p-tolyl-8-aza-bicyclo[3.2.1]oct-8-yl)-methanone | A |
| 26 | endo-Piperidin-1-yl-[3-(4-trifluoromethoxy-phenyl)-8-aza-bicyclo[3.2.1]oct-8-yl]-methanone | A |
| 27 | endo-[3-(4-Isopropyl-phenyl)-8-aza-bicyclo[3.2.1]oct-8-yl]-piperidin-1-yl-methanone | A |
| 28 | endo-[3-(4-Phenoxy-phenyl)-8-aza-bicyclo[3.2.1]oct-8-yl]-piperidin-1-yl-methanone | A |
| 29 | endo-Piperidin-1-yl-[3-(4-trimethylsilanyl-phenyl)-8-aza-bicyclo[3.2.1]oct-8-yl]-methanone | A |
| 30 | endo-4-[8-(Piperidine-1-carbonyl)-8-aza-bicyclo[3.2.1]oct-3-yl]-benzoic acid methyl ester | A |
| 31 | endo-[3-(4-Methoxymethyl-phenyl)-8-aza-bicyclo[3.2.1]oct-8-yl]-piperidin-1-yl-methanone | A |
| 32 | endo-Piperidin-1-yl-(3-pyridin-3-yl-8-aza-bicyclo[3.2.1]oct-8-yl)-methanone | A |
| 33 | endo-[3-(3,5-Dimethyl-isoxazol-4-yl)-8-aza-bicyclo[3.2.1]oct-8-yl]-piperidin-1-yl-methanone | A |
| 34 | endo-[3-(2-Methoxy-phenyl)-8-aza-bicyclo[3.2.1]oct-8-yl]-piperidin-1-yl-methanone | A |
| 35 | endo-Piperidin-1-yl-(3-o-tolyl-8-aza-bicyclo[3.2.1]oct-8-yl)-methanone | A |
| 36 | endo-[3-(2,6-Difluoro-phenyl)-8-aza-bicyclo[3.2.1]oct-8-yl]-piperidin-1-yl-methanone | A |

| Example No- | Chemical Name/Structure | In analogy to Procedure |
|---|---|---|
| 37 | endo-[3-(2,4-Difluoro-phenyl)-8-aza-bicyclo[3.2.1]oct-8-yl]-piperidin-1-yl-methanone | A |
| 38 | endo-(3-Naphthalen-2-yl-8-aza-bicyclo[3.2.1]oct-8-yl)-piperidin-1-yl-methanone | A |
| 39 | endo-[3-(3-Methoxy-phenyl)-8-aza-bicyclo[3.2.1]oct-8-yl]-piperidin-1-yl-methanone | A |
| 40 | endo-Piperidin-1-yl-(3-thiophen-2-yl-8-aza-bicyclo[3.2.1]oct-8-yl)-methanone | A |
| 41 | endo-Piperidin-1-yl-(3-thiophen-3-yl-8-aza-bicyclo[3.2.1]oct-8-yl)-methanone | A |
| 42 | endo-Piperidin-1-yl-(3-pyrimidin-5-yl-8-aza-bicyclo[3.2.1]oct-8-yl)-methanone | A |
| 43 | endo-Piperidin-1-yl-(3-pyridin-4-yl-8-aza-bicyclo[3.2.1]oct-8-yl)-methanone | A |
| 44 | endo-(3-Furan-3-yl-8-aza-bicyclo[3.2.1]oct-8-yl)-piperidin-1-yl-methanone | A |

Some examples of formulations will now be described in which the term "active substance" denotes one or more compounds according to the invention, including the salts thereof. In the case of one of the combinations with one or additional active substances as described previously, the term "active substance" also includes the additional active substances.

EXAMPLE A

Tablets Containing 100 mg of Active Substance

Composition:
1 tablet contains:

| | |
|---|---|
| active substance | 100.0 mg |
| lactose | 80.0 mg |
| corn starch | 34.0 mg |
| polyvinylpyrrolidone | 4.0 mg |
| magnesium stearate | 2.0 mg |
| | 220.0 mg |

Method of Preparation:

The active substance, lactose and starch are mixed together and uniformly moistened with an aqueous solution of the polyvinylpyrrolidone. After the moist composition has been screened (2.0 mm mesh size) and dried in a rack-type drier at 50° C. it is screened again (1.5 mm mesh size) and the lubricant is added. The finished mixture is compressed to form tablets.

Weight of tablet: 220 mg

Diameter: 10 mm, biplanar, facetted on both sides and notched on one side.

EXAMPLE B

Tablets Containing 150 Mg of Active Substance

Composition:
1 tablet contains:

| | |
|---|---|
| active substance | 150.0 mg |
| powdered lactose | 89.0 mg |
| corn starch | 40.0 mg |
| colloidal silica | 10.0 mg |
| polyvinylpyrrolidone | 10.0 mg |
| magnesium stearate | 1.0 mg |
| | 300.0 mg |

Preparation:

The active substance mixed with lactose, corn starch and silica is moistened with a 20% aqueous polyvinylpyrrolidone solution and passed through a screen with a mesh size of 1.5 mm. The granules, dried at 45° C., are passed through the same screen again and mixed with the specified amount of magnesium stearate. Tablets are pressed from the mixture.
Weight of tablet: 300 mg
die: 10 mm, flat

EXAMPLE C

Hard Gelatine Capsules Containing 150 Mg of Active Substance

Composition:
1 capsule contains:

| | | |
|---|---|---|
| active substance | | 150.0 mg |
| corn starch (dried) | approx. | 180.0 mg |
| lactose (powdered) | approx. | 87.0 mg |
| magnesium stearate | | 3.0 mg |
| | approx. | 420.0 mg |

Preparation:

The active substance is mixed with the excipients, passed through a screen with a mesh size of 0.75 mm and homogeneously mixed using a suitable apparatus. The finished mixture is packed into size 1 hard gelatine capsules.
Capsule filling: approx. 320 mg
Capsule shell: size 1 hard gelatine capsule.

EXAMPLE D

Suppositories Containing 150 Mg of Active Substance

Composition:
1 suppository contains:

| | |
|---|---|
| active substance | 150.0 mg |
| polyethyleneglycol 1500 | 550.0 mg |
| polyethyleneglycol 6000 | 460.0 mg |
| polyoxyethylene sorbitan monostearate | 840.0 mg |
| | 2,000.0 mg |

Preparation:

After the suppository mass has been melted the active substance is homogeneously distributed therein and the melt is poured into chilled moulds.

EXAMPLE E

Ampoules Containing 10 Mg Active Substance

Composition:

| | |
|---|---|
| active substance | 10.0 mg |
| 0.01N hydrochloric acid q.s. | |
| double-distilled water ad | 2.0 mL |

Preparation:

The active substance is dissolved in the necessary amount of 0.01 N HCl, made isotonic with common salt, filtered sterile and transferred into 2 mL ampoules.

EXAMPLE F

Ampoules Containing 50 Mg of Active Substance

Composition:

| | |
|---|---|
| active substance | 50.0 mg |
| 0.01N hydrochloric acid q.s. | |
| double-distilled water ad | 10.0 mL |

Preparation:

The active substance is dissolved in the necessary amount of 0.01 N HCl, made isotonic with common salt, filtered sterile and transferred into 10 mL ampoules.

The invention claimed is:
1. A compound of formula (I)

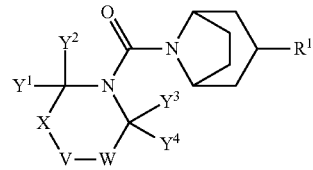

wherein
$R^1$ denotes phenyl
  wherein said phenyl is optionally substituted with one $R^2$ substituent,
$R^2$ denotes fluorine, methyl, isopropyl, methoxy, trifluoromethoxy, phenoxy, methoxycarbonyl, and methoxymethyl,
V is $CY^5Y^6$ or O,
W is $CY^7Y^8$,
X is absent or is $CY^{11}Y^{12}$,
$Y^1$ to $Y^{12}$, which may be identical and/or different, independently of each other denote hydrogen, methyl, trifluoromethyl, hydroxymethyl, 2-hydroxyprop-2-yl, hydroxy, methoxy, cyano, methoxycarbonyl, ethoxycarbonyl, and aminocarbonyl,
or a tautomer thereof, stereoisomer or mixture thereof, or salt thereof.

2. The compound of claim 1 of formula

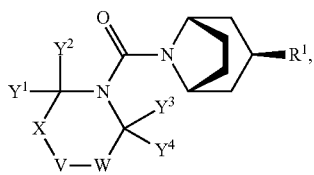

wherein the ethylene bridge and the residue $R^1$ are situated on the same face of the piperidine ring.

3. The compound according to claim 2, selected from the group consisting of:

endo-[3-(4-Fluoro-phenyl)-8-aza-bicyclo[3.2.1]oct-8-yl]-piperidin-1-yl-methanone

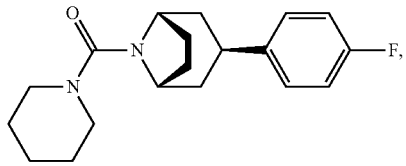

endo-[3-(4-Fluoro-phenyl)-8-aza-bicyclo[3.2.1]oct-8-yl]-pyrrolidin-1-yl-methanone

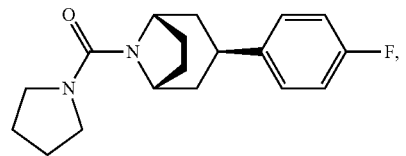

endo-[3-(4-Fluoro-phenyl)-8-aza-bicyclo[3.2.1]oct-8-yl]-morpholin-4-yl-methanone

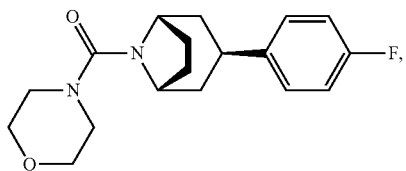

endo-N-{1-[3-(4-Fluoro-phenyl)-8-aza-bicyclo[3.2.1]octane-8-carbonyl]-piperidin-4-yl}-acetamide

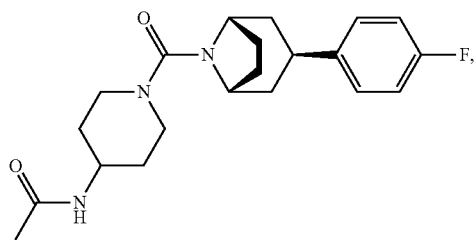

endo-[3-(4-Fluoro-phenyl)-8-aza-bicyclo[3.2.1]oct-8-yl]-(4-hydroxy-piperidin-1-yl)-methanone

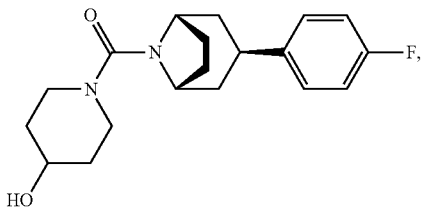

endo-1-[3-(4-Fluoro-phenyl)-8-aza-bicyclo[3.2.1]octane-8-carbonyl]-piperidine-4-carboxylic acid amide

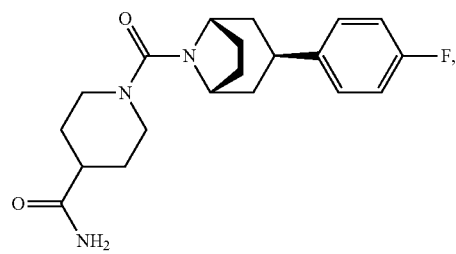

endo-1-[3-(4-Fluoro-phenyl)-8-aza-bicyclo[3.2.1]octane-8-carbonyl]-piperidine-4-carboxylic acid ethyl ester

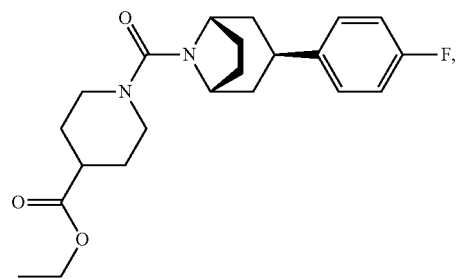

endo-1-[3-(4-Fluoro-phenyl)-8-aza-bicyclo[3.2.1]octane-8-carbonyl]-piperidine-4-carboxylic acid

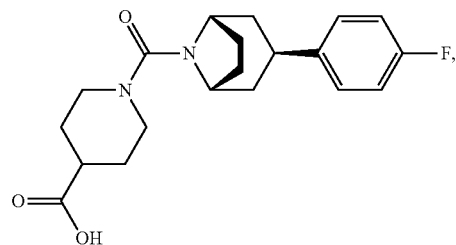

endo-1-[3-(4-Fluoro-phenyl)-8-aza-bicyclo[3.2.1]octane-8-carbonyl]-piperidine-4-carbonitrile

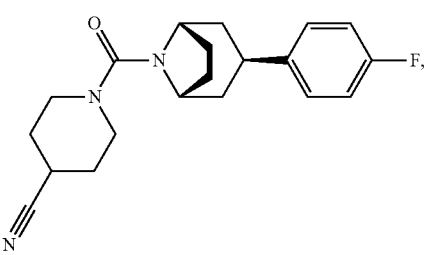

endo-[3-(4-Fluoro-phenyl)-8-aza-bicyclo[3.2.1]oct-8-yl]-(4-methoxy-piperidin-1-yl)-methanone

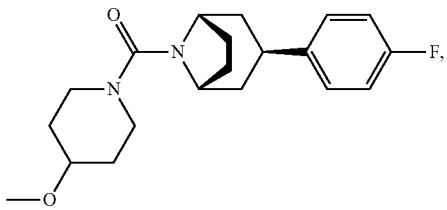

endo-[3-(4-Fluoro-phenyl)-8-aza-bicyclo[3.2.1]oct-8-yl]-(4-hydroxy-4-trifluoromethyl-piperidin-1-yl)-methanone

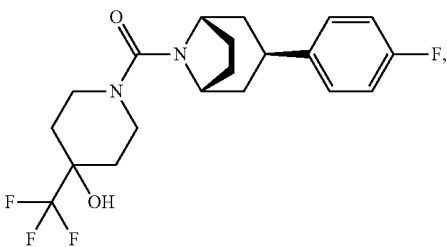

endo-1-[3-(4-Fluoro-phenyl)-8-aza-bicyclo[3.2.1]octane-8-carbonyl]-piperidine-4-carboxylic acid methyl ester

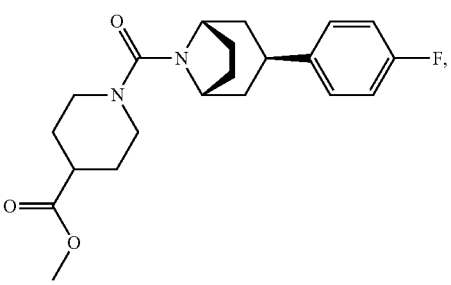

endo-[3-(4-Fluoro-phenyl)-8-aza-bicyclo[3.2.1]oct-8-yl]-(4-hydroxy-4-methyl-piperidin-1-yl)-methanone

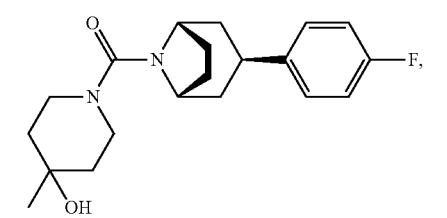

endo-[3-(4-Fluoro-phenyl)-8-aza-bicyclo[3.2.1]oct-8-yl]-(3-hydroxymethyl-piperidin-1-yl)-methanone

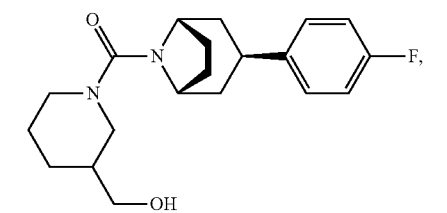

endo-[3-(4-Methoxy-phenyl)-8-aza-bicyclo[3.2.1]oct-8-yl]-piperidin-1-yl-methanone

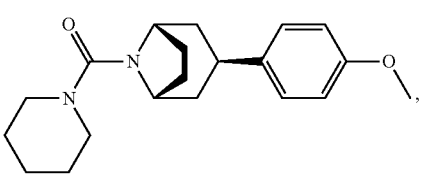

endo-Piperidin-1-yl-(3-p-tolyl-8-aza-bicyclo[3.2.1]oct-8-yl)-methanone

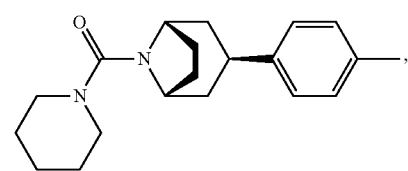

endo-Piperidin-1-yl-[3-(4-trifluoromethoxy-phenyl)-8-aza-bicyclo[3.2.1]oct-8-yl]-methanone

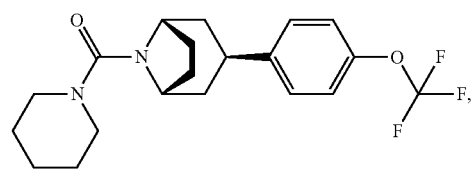

endo-[3-(4-Isopropyl-phenyl)-8-aza-bicyclo[3.2.1]oct-8-yl]-piperidin-1-yl-methanone

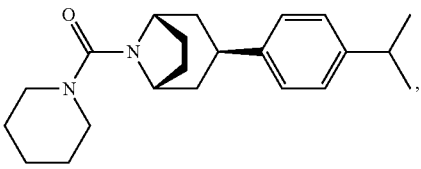

endo-[3-(4-Phenoxy-phenyl)-8-aza-bicyclo[3.2.1]oct-8-yl]-piperidin-1-yl-methanone

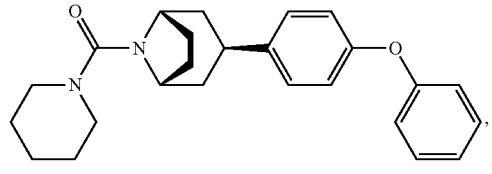

endo-4-[8-(Piperidine-1-carbonyl)-8-aza-bi-cyclo[3.2.1]oct-3-yl]-benzoic acid methyl ester

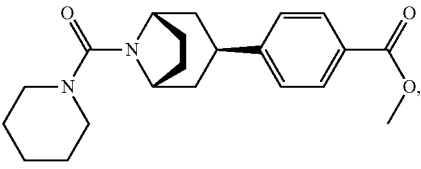

endo-[3-(4-Methoxymethyl-phenyl)-8-aza-bicyclo[3.2.1]
oct-8-yl]-piperidin-1-yl-methanone

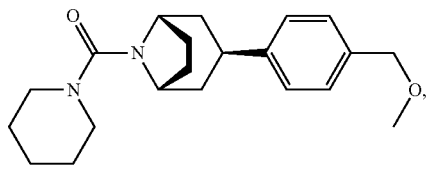

endo-[3-(2-Methoxy-phenyl)-8-aza-bicyclo[3.2.1]oct-8-
yl]-piperidin-1-yl-methanone

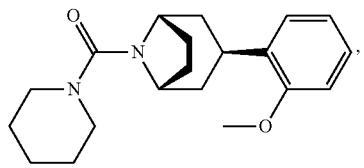

endo-Piperidin-1-yl-(3-o-tolyl-8-aza-bicyclo[3.2.1]oct-8-
yl)-methanone

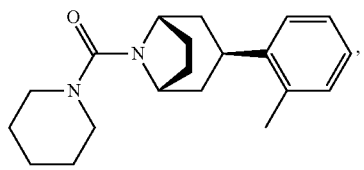

endo-[3-(3-Methoxy-phenyl)-8-aza-bicyclo[3.2.1]oct-8-
yl]-piperidin-1-yl-methanone

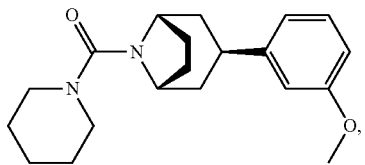

or salt thereof.

4. A physiologically acceptable salt of a compound according to claim 1 with an inorganic or organic acid or base.

5. A pharmaceutical composition containing a therapeutically effective amount of compound according to claim 1, or a physiologically acceptable salt with an inorganic or organic acid or base, optionally together with one or more inert carriers and/or diluents.

6. A method of treating type 2 diabetes mellitus comprising administering a therapeutically effective amount of a compound according to claim 1, or a physiologically acceptable salt with an inorganic or organic acid or base.

7. A method of administering a pharmaceutical composition according to claim 5, for the treatment of type 2 diabetes mellitus.

8. Process for preparing a compound of formula I according to claim 1, or a physiologically acceptable salt with an inorganic or organic acid or base, characterized in that an amine of formula III

wherein the group $R^1$ is defined as hereinbefore and hereinafter,
or an amine of formula IV

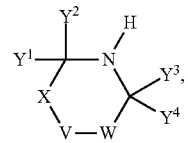

wherein the groups $Y^1$ to $Y^4$, V, W, and X are defined as hereinbefore and hereinafter,
is reacted with a carbonic acid derivative of the formula Y—CO—Y, yielding a compound either of formula V or VI as intermediate

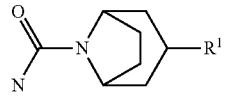

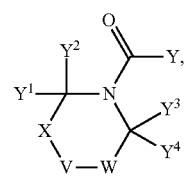

wherein the groups $R^1$, $Y^1$ to $Y^4$, V, W, and X are defined as hereinbefore and hereinafter and
wherein Y is a leaving group and denotes fluorine, chlorine, bromine, cyano, $C_{1-9}$-alkoxy, $C_{2-6}$-alkenyloxy, $C_{2-6}$-alkynyloxy, aryloxy, heteroaryloxy, $C_{1-8}$-alkylsulfanyl, heteroar-N-yl, arylotriazol-1-yloxy, heteroarylotriazol-1-yloxy, 3-methyl-imidazol-1-yl, succinyl-N-oxy, di-($C_{1-4}$-alkyl)aminocarbonyloxy, pyrrol-1-ylcarbonyloxy, piperidin-1-yl-carbonyloxy, morpholin-4-ylcarbonyloxy, arylsulfanyl, or hetero-arylsulfanyl,
while the alkyl, alkenyl, and alkynyl groups mentioned in the definition of the above group are optionally substituted with one or more substituents, preferably with one to five substituents, independently of each other selected from fluorine, chlorine, $C_{1-3}$-alkyl, or $C_{1-3}$-alkoxy,
while the aryl groups mentioned in the definition of the above group denote phenyl or naphthyl and the heteroaryl groups mentioned in the definition of the above group denote pyridinyl, pyrimidinyl, triazinyl, imidazolyl, pyrazolyl, triazolyl, tetrazolyl, whilst both the aryl and heteroaryl groups are optionally substituted with one or more substituents, preferably with one to five, independently of each other selected from fluorine, chlorine, bromine, $C_{1-3}$-alkyl, $C_{1-3}$-alkyloxy, nitro, cyano, or di-($C_{1-3}$-alkyl)-amino,
while the two Y in Y—CO—Y may be identical or different, while the second Y to be replaced may also be transformed into a more reactive Y after the first Y is replaced with one of the two amines, while the intermediates of formula V and VI are optionally isolated and optionally purified, before being subsequently reacted with the other amine of the formula III or IV to yield a compound of the formula I;

the reactions are conducted optionally in the presence of an organic base or an inorganic base, and/or an additive between −10 and 120° C. in solvents selected from tetrahydrofuran, 1,2-dimethoxyethane, ether, 1,4-dioxane, N,N-dimethylformamide, N,N-dimethylacetamide, N-methylpyrrolidinone, acetonitrile, ethyl acetate, dichloromethane, 1,2-dichloroethane, toluene, benzene, and hexanes;

and, if necessary any protective group used in the reactions described above is cleaved concurrently or subsequently;

if desired a compound of formula I thus obtained is resolved into its stereoisomers;

if desired a compound of formula I thus obtained is converted into a physiologically acceptable salt thereof.

* * * * *